US009663573B2

(12) United States Patent
French et al.

(10) Patent No.: US 9,663,573 B2
(45) Date of Patent: May 30, 2017

(54) METHODS OF TREATING LIVER CONDITIONS USING NOTCH2 ANTAGONISTS

(75) Inventors: Dorothy French, San Carlos, CA (US); Christian W. Siebel, Berkeley, CA (US); Erik Huntzicker, Los Altos, CA (US)

(73) Assignee: GENENTECH, INC., South San Francisco, CA (US)

( * ) Notice: Subject to any disclaimer, the term of this patent is extended or adjusted under 35 U.S.C. 154(b) by 195 days.

(21) Appl. No.: 14/349,005

(22) PCT Filed: Apr. 6, 2012

(86) PCT No.: PCT/US2012/032621

§ 371 (c)(1),
(2), (4) Date: Nov. 20, 2014

(87) PCT Pub. No.: WO2013/052155

PCT Pub. Date: Apr. 11, 2013

(65) Prior Publication Data

US 2015/0064186 A1 Mar. 5, 2015

Related U.S. Application Data

(60) Provisional application No. 61/543,483, filed on Oct. 5, 2011.

(51) Int. Cl.

| | |
|---|---|
| ***A61K 39/395*** | (2006.01) |
| ***A61P 1/16*** | (2006.01) |
| ***C07K 16/28*** | (2006.01) |
| *C07K 14/705* | (2006.01) |
| *C07K 14/715* | (2006.01) |
| *C07K 14/71* | (2006.01) |
| *A61K 39/00* | (2006.01) |

(52) U.S. Cl.

CPC ............ *C07K 16/28* (2013.01); *A61K 39/395* (2013.01); *A61K 39/3955* (2013.01); *A61K 2039/505* (2013.01); *C07K 14/705* (2013.01); *C07K 14/71* (2013.01); *C07K 14/715* (2013.01); *C07K 16/2863* (2013.01); *C07K 16/2866* (2013.01); *C07K 2317/31* (2013.01); *C07K 2317/33* (2013.01); *C07K 2317/34* (2013.01); *C07K 2317/76* (2013.01)

(58) Field of Classification Search

CPC .......... A61K 2039/505; A61K 2300/00; A61K 39/3955; A61K 39/00; A61K 39/395; A61K 38/177; A61K 38/179; C07K 14/71; C07K 16/28; C07K 2317/76; C07K 16/18; C07K 14/705; C07K 16/00; C07K 16/2863; C07K 16/2866

See application file for complete search history.

(56) References Cited

U.S. PATENT DOCUMENTS

| | | | | |
|---|---|---|---|---|
| 6,703,489 | B1 | 3/2004 | Lewis et al. | |
| 7,754,206 | B2 | 7/2010 | Clarke et al. | |
| 2004/0101847 | A1* | 5/2004 | Freier ................ | C12N 15/1138 435/6.16 |
| 2008/0131434 | A1* | 6/2008 | Lewicki ................ | C07K 16/28 424/138.1 |
| 2008/0317760 | A1 | 12/2008 | Gurney et al. | |
| 2009/0081238 | A1 | 3/2009 | Siebel et al. | |
| 2010/0080808 | A1* | 4/2010 | Siebel .................... | C07K 16/28 424/143.1 |
| 2010/0111958 | A1* | 5/2010 | Gurney ................ | C07K 16/462 424/139.1 |
| 2010/0196385 | A1 | 8/2010 | Bedian et al. | |
| 2014/0314749 | A1 | 10/2014 | French et al. | |
| 2015/0232568 | A1 | 8/2015 | Siebel et al. | |

FOREIGN PATENT DOCUMENTS

| | | | |
|---|---|---|---|
| WO | 2004/019921 | A2 | 3/2004 |
| WO | 2006/135949 | | 12/2006 |
| WO | WO-2008057144 | A2 * | 5/2008 |
| WO | 2008/140826 | A1 | 11/2008 |
| WO | 2009/124931 | A2 | 10/2009 |
| WO | 2010005566 | | 1/2010 |
| WO | 2010039832 | | 4/2010 |
| WO | 2011/063237 | A1 | 5/2011 |
| WO | 2013/052155 | A1 | 4/2013 |
| WO | 2013/052155 | A9 | 4/2013 |
| WO | 2013/192550 | A2 | 12/2013 |
| WO | 2014/028446 | A1 | 2/2014 |
| WO | 2014/151866 | A1 | 9/2014 |

OTHER PUBLICATIONS

Dill et al. Constitutive Notch2 signaling induces hepatic tumors in mice. Hepatology 57: 1607-1619, 2013.*

Huntzinger et al. Differential effects of targeting Notch receptors in a mouse model of liver cancer. Hepatology 61: 942-952, 2015.*

Jensen et al. Transit-amplifying ductal (oval) cells and their hepatic progeny are characterized by a novel and distinctive expression of delta-like protein/preadipocyte factor 1/fetal antigen 1. Am J Pathol 164(4): 1347-1359, 2005.*

Tanimizu et al. Notch signaling controls hepatoblast differentiation by altering the expression of liver-enriched transcription factors. J Cell Sci 117(15): 3165-3174, 2004.*

Tchorz et al. Notch2 signaling promotes biliary epithelial cell fate specification and tubulogenesis during bile duct development in mice. Hepatology 50: 871-879, 2009.*

Artavanis-Tsakonas et al., "Choosing a cell fate: a view from the Notch locus" Reviews 7(11-12) (1991).

Bork, et al., "Go hunting in sequence databases but watch out for the traps" Trends in Genetics 12(10):425-427 (Oct. 1996).

(Continued)

*Primary Examiner* — Bridget E Bunner

(74) *Attorney, Agent, or Firm* — McNeill Baur PLLC

(57) ABSTRACT

Methods and compositions for the treatment of liver conditions are provided, such methods and compositions comprising Notch2 antagonists, e.g., anti-Notch2 antibodies. Liver conditions include, but are not limited to, chronic liver disease.

12 Claims, 45 Drawing Sheets

(56) References Cited

OTHER PUBLICATIONS

Bork, "Powers and Pitfalls in Sequence Analysis: The 70% hurdle" Genome Research (10):398-400 (2000).
Brenner, "Errors in genome annotation" Trends in Genetics 15(4):132-133 (1999).
Brorson, "Mutational analysis of avidity and fine specificity of anti-levan antibodies" J Immunol (added article title info), 163:6694-6701 (Dec. 1999).
Brummell et al. et al., "Probing the combining site of an anti-carbohydrate antibody by saturation-mutagenesis: role of the heavy-chain CDR3 residues" Biochemistry 32(4):1180-1187 (Feb. 1993).
Burks, E., et al. et al., "In vitro scanning saturation mutagenesis of an antibody binding pocket" P Natl Acad Sci USA 94:412-417 (1997).
Cao et al., "Osteopontin as potential biomarker and therapeutic target in gastric and liver cancers" World J. Gastroenterol. 18(30):3923-3930 (2012).
Chen et al., "An antibody drug conjugate targeting PMEL17" J. Biol. Chem. (Manuscript M112.361485), (May 21, 2012).
Coleman, P.M., "Effects of amino acid sequence changes on anti-body-antigen interactions" Res Immunol 145:33-36 (1994).
Darwiche et al., "Inhibition of Notch signaling affects hepatic oval cell response in rat model of 2AAF-PH" Dove Press 3:89-98 (2011).
Doercks et al., "Protein annotation: detective work for function prediction" Trends in Genetics 14(6):248-250 (1998).
Dooley et al., "Notch Signaling Plays a Critical Role on Experimental and Human Liver Fibrogenesis" J. Hepatol. 52(SUPPL 1): S48 (2010).
Dorothy French, DVM. PhD, DACVP, "Microarray analysis reveals signaling pathways critical for hepatic progenitor cell survival and self-renewal" Slides ASIP Meeting, pp. 53 (Apr. 8, 2011).
Fan B et al., "Cholangiocarcinomas can originate from hepatocytes in mice" The Journal of clinical investigation 122(8):2911-2915 (2012).
Fiorotto, R. et al., "Prgenitor Cell Activation and Liver Repair is Altered in Notch2 and RBP-J kappa-Defective Mice Exposed to Cholestatic Injuries" Journal of Hepatology 52(1):S45 (Apr. 2010).
Gao et al., "Expression of Jagged1 and its association with hepatitus B virus X protein in hepatocellular carcinoma" Biochemical and Biophysical Research Communications 356:341-347 (2007).
Gao et al., "Notch1 activation contributes to tumor cell growth and proliferation in human hepatocellular carcinoma HepG2 and SMMC7721 cells" International journal of oncology 41(5):1773-1781 (2012).
Geisler et al., "Liver-Specific Inactivation of Notch2, but not Notch1, Comprises Intrahepatic Bile Duct Development in Mice" Live Biology/Pathobiology 48(2):607-616 (Aug. 2008).
Gotoh et al., "Overexpression of osteopontin in hepatocellular carcinoma" Pathology International 52:19-24 (2002).
Groth et al., "Therapeutic Approaches to Modulating Notch Signaling: Current challenges and future prospects" Seminars in Cell & Development Biology 23:465-472 (2012).
Hattori et al., "Expression of the RNA-binding protein Musashi1 in adult liver stem-like cells" Hepatology Research 40:432-437.
Ho et al., "Advances in Liver Cancer AntibodyTherapies" Biodrugs 25(5):275-284 (2011).
Ho et al., "AKT (v-Akt Murine Thymoma Viral Oncogene Homolog 1) and N-Ras (Neuroblastoma Ras Viral Oncogene Homolog) Coactivation in the Mouse Liver Promotes Rapid Carcinogenesis by Way of mTOR (Mammalian Target of Rapamycin Complex 1), FOXM1 (Forkhead Box M1)/SKP2, and c-Myc Pathways" Hepatology 55:833-845 (2012).
International Search Report and Written Opinion for International App. No. PCT/US2014/026588, pp. 23 (mailed Aug. 20, 2014).
International Search Report and Written Opinion for PCT Application No. PCT/US2015/015456, filed Feb. 11, 2015, pp. 13 (mailed May 7, 2015)
International Search Report for International Patent Application No. PCT/US2013/054664, pp. 5 (mailed Dec. 3, 2013).
Jang et al., "The structural basis for DNA binding by an anti-DNA autoantibody"Mol Immunol. 35(18):1207-17 (Dec. 1998).
Kobayashi, H., et al. et al., "Tryptophan H33 plays an important role in pyrimidin (6-4) pyrimidone photoproduct binding by a high-affinity antibody" Protein Eng 12(10):879-884 (1994).
Koch et al., "Notch and Cancer: a double-edges sword" Cellular and Molecular Life Sciences 64:2746-2762 (2007).
Litten et al., "Activated NOTCH2 is Overexpressed in Hepatoblastomas: An Immunohistochemical Study" Pediatric Develop. Pathol. 14:378-383 (2011).
Louvi et al., "Notch and disease: A growing field" Seminars in Cell & Development Biology 23:473-480 (2012).
Lozier et al., "Notch signaling regulates bile duct morphogensis in mice" PloS One 3(3):e1851 (2008).
McCright et al., "A mouse model of Alagille syndrome: Notch2 as a genetic modifier of Jag1 haploinsufficiency" Development 129(4):1075-82 (Feb. 2002).
Mullendore et al., "Ligand-dependent Notch Signaling is Involved in Tumor Initiation and Tumor Maintenance in Pancreatic Cancer" Clinical Cancer Research 15:2291-2301 (Apr. 1, 2009).
Ngo et al., "Computational complexity, protein structure prediction, and the Levinthal paradox" The Protein Folding Problem and Tertiary Structure Prediction pp. 492-495 (1994).
Nijjar et al., "Notch receptor expression in adult human liver: a possible role in bile duct formation and hepatic neovascularization" Hepatology 34:1184-1192 (2001).
Nishina et al., "Restored expression of the tumor suppressor gene RUNX3 reduces cancer stem cells in hepatocellular carcinoma by suppressing Jagged1—Notch signaling" Oncology Reports 26:523-531 (2011).
Oda et al., "Mutations in the human Jagged1 gene are responsible for Alagille syndrome" Nat. Genet. 16:235-42 (Jul. 1997).
Orr et al., "Mechanism of Action of the Antifibrogenic Compound Gliotoxin in Rat Liver Cells" Hepatology 40:232-242 (2004).
Piccoli et al., "Alagille syndrome and the Jagged1 gene" Semin Liver Dis. 21(4):525-34 (2001).
Pikarsky et al., "NF-kb functions as a tumor promoter in inflammation-associated cancer" Nature 43:461-469 (Sep. 23, 2004).
Qi et al., "Notch1 signalinf inhibits growth of human hepatocellular carcinoma through induction of cell cycle arrest and apoptosis" Cancer Research (63):8323-8329 (Dec. 1, 2003).
Ryan et al., "Bile duct proliferation in Jag1/fringe heterozygous mice indentifies candidate modifiers of the Alagille syndrome hepatic phenotype" Hepatology 48(6):1989-97 (2008).
Sakurai et al., "Loss of hepatic NF-kb activity enhances chemical hepatocarcinogenesis through sustained c-Jun N-terminal kinase 1 activation" PNAS 103(28):10544-10551 (Jul. 11, 2006).
Sekiya et al., "Intrahepatic cholangiocarcinoma can arise from Notch-mediated conversion of hepatocytes" The Journal of Clinical Investigation 122(11):3914-3918 (2012).
Shen et al., "GSI—has a better effect in inhibiting hepatocellular carcinoma cell growth than GSI-X, or GSI-XXI" Anticancer Drugs 23:683-690 (2012).
Shin et al., "SPP1 polymorphisms associated with HBV clearance and HCC occurence" Intl. J. Epidemiology 36:1001-1008 (2007).
Skolnick et al., "From genes to protein structure and function: novel applications of computational approaches in the genomic era" Trends in Biotech. 18(1):34-39 (2000).
Smith et al., "The challenges of genome sequence annotation of 'the devil is in the details'" Nature Biotech (15):1222-1223 (1997).
Sparks et al., "Notch signaling regulaes formation of the three-dimensional architechture of intrahepatic bile ducts in mice" Hepatology 51(4):1391-400 (2010).
Spee et al., "Characterization of the activated liver progenitor cell niche, potential involvement of Wnt and Notch signaling" Gut (abstract only (2 pages)), 59:247-257 (2010).
Tokuriki, et al., "Stability effects of mutations and protein evolvability" Current Opinion in Structural Biology 19:596-604 (2009).
Viatour et al., "Notch signaling inhibits hepatocellular carcinoma following inactiviation of the RB pathway" The Journal of Experimental Medicine 208(10):1963-1976 (Aug. 29, 2011).

(56) References Cited

OTHER PUBLICATIONS

Villanueva et al., "Notch Signaling is Activated in Human Hepatocellular Carcinoma and Induces Tumor Formation in Mice" Gastroenterology 143:1660-1669 (2012).
Wakabayashi et al., "Regulation of Notch1 Signaling by Nrf2: Implications for Tissue Regeneration" Science Signaling 3(130):1-11 (Jul. 13, 2010).
Wang et al., "Hepatitus B Virus X protein promotes the growth of hepatocellular carcinoma by modulation of the Notch signaling pathway" Oncology Reports 27:1170-1176 (2012).
Wang et al., "Notch1 signaling contributes to the oncogenic effect of HBx on human hepatic cells"Biotechnol. Lett 35:29-37 (2012).
Wang et al., "Notch1 signaling sensitizing tumor necrosis factor-related apoptosis-inducing ligand-induced apoptosis in human hepatocellular carcinoma cells by inhibiting Akt/Hdm2-mediated p53 degradation and up-regulating p53-dependent DR5 expression"Journal of Biological Chemistry 284(24):16183-16190 (2009).
Wells, "Addivity of Mutational Effects in Proteins"Biochemistry 29:8509-8517 (1990).
Written Opinion for International Patent Application No. PCT/US2013/054664., pp. 5 (mailed Dec. 3, 2013).
Wu et al. et al., "Therapeutic Antibody targeting of individual Notch receptors" Nature 464:1052-1057 (2010).
Wu et al., "Notch Signaling and its role in breast cancer" Frontiers in Bioscience 12:4370-4383 (2007).
Xu et al., "Yes—Associated Protein is an Independent Prognostic Marker in Hepatocellular Carcinoma" Cancer (115):4576-85 (Oct. 1, 2009).
Yuen et al., "Serological markers of liver cancer" Best Practice & Research Clinical Gastroenterology 19(1):91-99 (2005).
Zender et al., "Identification and Validation of Oncogenes in Liver Cancer Using an Integrative Oncogenomic Approach" Cell (125):1253-1267 (Jun. 30, 2006).
Zeuner et al., "The Notch2-Jagged1 interaction mediates stem cell factor signaling in erythropoiesis" Cell Death Differ. 18(2):371-80 (2011).
Zhou et al., "Downregulation of the Notch signaling pathway inhibits hepatocellular carcinoma cell invasion by inactivation of matrix metalloproteinase-2 and-9 and vascular endothelial growth factor" Oncology reports 28(3):874-882 (2012).
Zhou et al., "The Down-Regulation of Notch1 Inhibits the Invasion and Migration of Hepatocellular Carcinoma Cells by Inactivating the Cyclooxygenase-2/Snail/E-cadherin Pathway In Vitro" Dig. Dis Sci (2012).
Written Opinion for International Patent Application No. PCT/US2013/032621, pp. 8 (mailed Apr. 5, 2014).

* cited by examiner

Isotype | anti-Notch2
H&E
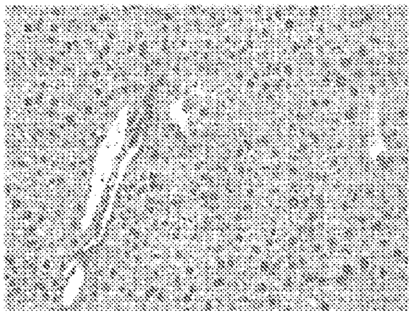
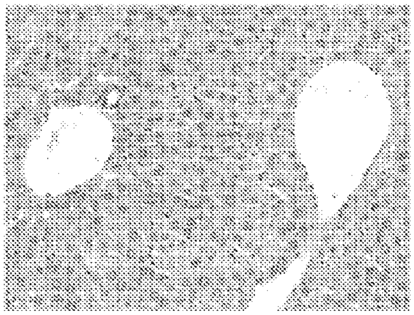
2 Weeks Post phx
FIG. 3A-1 FIG. 3A-2
BrdU
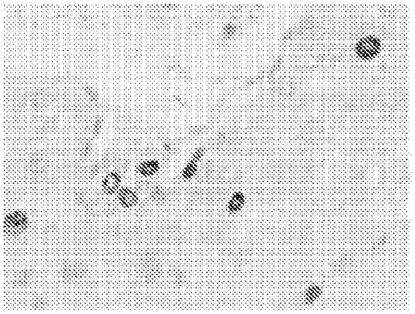
40 Hrs after 2/3 phx
FIG. 3B-1 FIG. 3B-2
Hes1
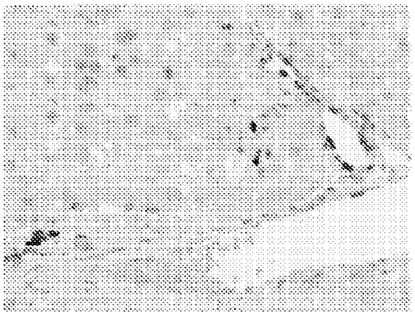
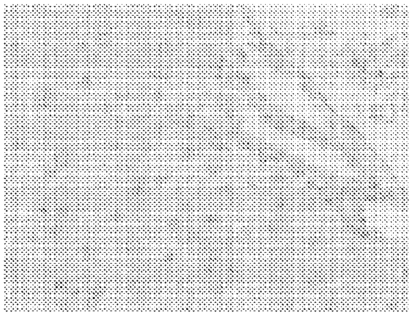
40 Hrs after 2/3 phx
FIG. 3C-1 FIG. 3C-2
pan-CK
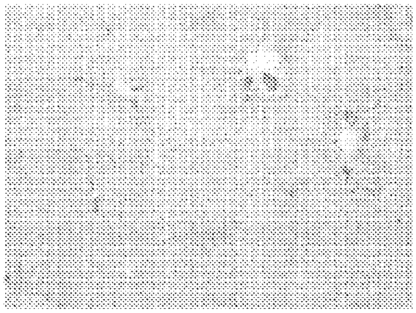
DDC Diet 4 Weeks
FIG. 3D-1 FIG. 3D-2

HVR-H1 Sequences - Antibody D and Affinity Matured Antibodies Derived from Antibody D

| | | Kabat Number | | | | | | | | | |
|---|---|---|---|---|---|---|---|---|---|---|---|
| Antibody # | SEQ ID NO: | 26 | 27 | 28 | 29 | 30 | 31 | 32 | 33 | 34 | 35 |
| D | 1 | G | Y | S | F | T | S | Y | G | M | S |
| D-1, D-2, D-3 | 2 | G | Y | T | F | S | S | Y | G | M | S |
| Consensus | 3 | G | Y | S/T | F | S/T | S | Y | G | M | S |

HVR-H2 Sequence - Antibody D and Affinity Matured Antibodies Derived from Antibody D

| | | Kabat Number | | | | | | | | | | | | | | | | | |
|---|---|---|---|---|---|---|---|---|---|---|---|---|---|---|---|---|---|---|---|
| Antibody # | SEQ ID NO: | 49 | 50 | 51 | 52 | 52a | 53 | 54 | 55 | 56 | 57 | 58 | 59 | 60 | 61 | 62 | 63 | 64 | 65 |
| D, D-1, D-2, D-3 | 4 | S | Y | I | Y | P | Y | S | G | A | T | Y | Y | A | D | S | V | K | G |

HVR-H3 Sequence - Antibody D and Affinity Matured Antibodies Derived from Antibody D

| | | Kabat Number | | | | | | | | | | | | |
|---|---|---|---|---|---|---|---|---|---|---|---|---|---|---|
| Antibody # | SEQ ID NO: | 95 | 96 | 97 | 98 | 99 | 100 | 100A | 100B | 100C | 100D | 100K | 101 | 102 |
| D, D-1, D-2, D-3 | 5 | H | S | G | Y | Y | R | I | S | S | A | M | D | V |

FIG. 12

HVR-L1 Sequences - Antibody D and Affinity Matured Antibodies Derived from Antibody D

| | | Kabat Number | | | | | | | | | | |
|---|---|---|---|---|---|---|---|---|---|---|---|---|
| Antibody # | SEQ ID NO: | 24 | 25 | 26 | 27 | 28 | 29 | 30 | 31 | 32 | 33 | 34 |
| D | 6 | R | A | S | Q | S | I | S | S | Y | L | A |
| D-1 | 7 | R | A | S | Q | S | N | R | R | F | L | A |
| D-2 | 8 | R | A | S | Q | S | V | R | S | F | L | A |
| D-3 | 9 | R | A | S | Q | N | I | K | R | F | L | A |
| Consensus | 10 | R | A | S | Q | S/N | I/N/V | S/R/K | S/R | Y/F | L | A |

HVR-L2 Sequences - Antibody D and Affinity Matured Antibodies Derived from Antibody D

| | | Kabat Number | | | | | | |
|---|---|---|---|---|---|---|---|---|
| Antibody # | SEQ ID NO: | 50 | 51 | 52 | 53 | 54 | 55 | 56 |
| D, D-1 | 11 | G | A | S | S | R | A | S |
| D-2 | 12 | R | A | S | I | R | A | S |
| D-3 | 13 | G | A | S | T | R | E | S |
| Consensus | 14 | G/R | A | S | S/I/T | R | A/E | S |

HVR-L3 Sequences - Antibody D and Affinity Matured Antibodies Derived from Antibody D

| | | Kabat Number | | | | | | | | |
|---|---|---|---|---|---|---|---|---|---|---|
| Clone # | SEQ ID NO: | 89 | 90 | 91 | 92 | 93 | 94 | 95 | 96 | 97 |
| D | 15 | Q | Q | Y | Y | S | S | P | L | T |
| D-1 | 16 | Q | Q | Y | Y | I | S | P | L | T |
| D-2 | 17 | Q | Q | Y | Y | I | S | P | W | T |
| D-3 | 18 | Q | Q | Y | Y | R | S | P | H | T |
| Consensus | 19 | Q | Q | Y | Y | S/I/R | S | P | L/W/H | T |

FIG. 13

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35A | 35B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Antibody D | E | V | Q | L | V | E | S | G | G | G | L | V | Q | P | G | G | S | L | R | L | S | C | A | A | S | G | Y | S | F | T | S | Y | G | M | S | | | W | V | R | Q | A | P | G | K |
| Antibody D-1 | E | V | Q | L | V | E | S | G | G | G | L | V | Q | P | G | G | S | L | R | L | S | C | A | A | S | G | Y | T | F | S | S | Y | G | M | S | | | W | V | R | Q | A | P | G | K |
| Antibody D-2 | E | V | Q | L | V | E | S | G | G | G | L | V | Q | P | G | G | S | L | R | L | S | C | A | A | S | G | Y | T | F | S | S | Y | G | M | S | | | W | V | R | Q | A | P | G | K |
| Antibody D-3 | E | V | Q | L | V | E | S | G | G | G | L | V | Q | P | G | G | S | L | R | L | S | C | A | A | S | G | Y | T | F | S | S | Y | G | M | S | | | W | V | R | Q | A | P | G | K |

| Kabat# | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Antibody D | G | L | E | W | V | S | Y | I | Y | P | | | Y | S | G | A | T | Y | Y | A | D | S | V | K | G | R | F | T | I | S | A | D | T | S | K | N | T | A | Y | L | Q | M | N |
| Antibody D-1 | G | L | E | W | V | S | Y | I | Y | P | | | Y | S | G | A | T | Y | Y | A | D | S | V | K | G | R | F | T | I | S | A | D | T | S | K | N | T | A | Y | L | Q | M | N |
| Antibody D-2 | G | L | E | W | V | S | Y | I | Y | P | | | Y | S | G | A | T | Y | Y | A | D | S | V | K | G | R | F | T | I | S | A | D | T | S | K | N | T | A | Y | L | Q | M | N |
| Antibody D-3 | G | L | E | W | V | S | Y | I | Y | P | | | Y | S | G | A | T | Y | Y | A | D | S | V | K | G | R | F | T | I | S | A | D | T | S | K | N | T | A | Y | L | Q | M | N |

| Kabat# | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Antibody D | S | L | R | A | E | D | T | A | V | Y | Y | C | A | R | H | S | G | Y | Y | R | I | S | S | A | | | | | | | | M | D | V | W | G | Q | G | T | L | V | T | V | S | A | SEQ ID NO: 20 |
| Antibody D-1 | S | L | R | A | E | D | T | A | V | Y | Y | C | A | R | H | S | G | Y | Y | R | I | S | S | A | | | | | | | | M | D | V | W | G | Q | G | T | L | V | T | V | S | A | SEQ ID NO: 21 |
| Antibody D-2 | S | L | R | A | E | D | T | A | V | Y | Y | C | A | R | H | S | G | Y | Y | R | I | S | S | A | | | | | | | | M | D | V | W | G | Q | G | T | L | V | T | V | S | A | SEQ ID NO: 21 |
| Antibody D-3 | S | L | R | A | E | D | T | A | V | Y | Y | C | A | R | H | S | G | Y | Y | R | I | S | S | A | | | | | | | | M | D | V | W | G | Q | G | T | L | V | T | V | S | A | SEQ ID NO: 21 |

FIG. 14

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Antibody D | D | I | Q | M | T | Q | S | P | S | S | L | S | A | S | V | G | D | R | V | T | I | T | C | R | A | S | Q | | | | | | | S | I | S | S | Y | L | A | W | Y | Q |
| Antibody D-1 | D | I | Q | M | T | Q | S | P | S | S | L | S | A | S | V | G | D | R | V | T | I | T | C | R | A | S | Q | | | | | | | S | N | R | R | F | L | A | W | Y | Q |
| Antibody D-2 | D | I | Q | M | T | Q | S | P | S | S | L | S | A | S | V | G | D | R | V | T | I | T | C | R | A | S | Q | | | | | | | S | V | R | S | F | L | A | W | Y | Q |
| Antibody D-3 | D | I | Q | M | T | Q | S | P | S | S | L | S | A | S | V | G | D | R | V | T | I | T | C | R | A | S | Q | | | | | | | N | I | K | R | F | L | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Antibody D | Q | K | P | G | K | A | P | K | L | L | I | Y | G | A | S | S | R | A | S | G | V | P | S | R | F | S | G | S | G | S | G | T | D | F | T | L | T | I | S | S | L | Q | P |
| Antibody D-1 | Q | K | P | G | K | A | P | K | L | L | I | Y | G | A | S | S | R | A | S | G | V | P | S | R | F | S | G | S | G | S | G | T | D | F | T | L | T | I | S | S | L | Q | P |
| Antibody D-2 | Q | K | P | G | K | A | P | K | L | L | I | Y | R | A | S | I | R | A | S | G | V | P | S | R | F | S | G | S | G | S | G | T | D | F | T | L | T | I | S | S | L | Q | P |
| Antibody D-3 | Q | K | P | G | K | A | P | K | L | L | I | Y | G | A | S | T | R | E | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 | |
|---|---|---|---|---|---|---|---|---|---|---|---|---|---|---|---|---|---|---|---|---|---|---|---|---|---|---|---|---|---|---|---|---|---|---|---|
| Antibody D | E | D | F | A | T | Y | Y | C | Q | Q | Y | Y | S | S | P | | | | | | | L | T | F | G | Q | G | T | K | V | E | I | K | R | SEQ ID NO: 22 |
| Antibody D-1 | E | D | F | A | T | Y | Y | C | Q | Q | Y | Y | I | S | P | | | | | | | L | T | F | G | Q | G | T | K | V | E | I | K | R | SEQ ID NO: 23 |
| Antibody D-2 | E | D | F | A | T | Y | Y | C | Q | Q | Y | Y | I | S | P | | | | | | | W | T | F | G | Q | G | T | K | V | E | I | K | R | SEQ ID NO: 24 |
| Antibody D-3 | E | D | F | A | T | Y | Y | C | Q | Q | Y | Y | R | S | P | | | | | | | H | T | F | G | Q | G | T | K | V | E | I | K | R | SEQ ID NO: 25 |

*FIG. 15*

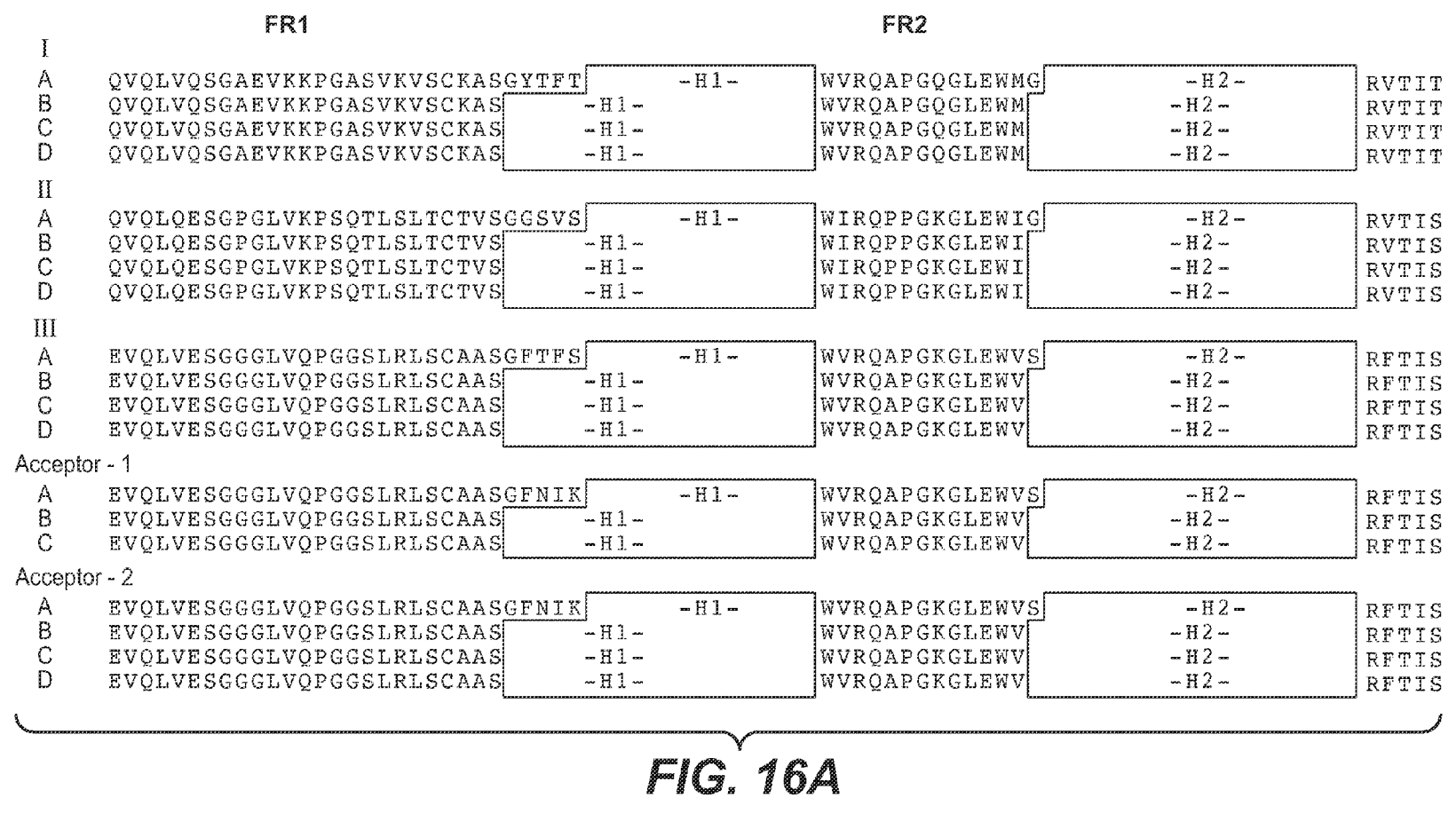

| | FR1 | | FR2 | | |
|---|---|---|---|---|---|
| I | | | | | |
| A | QVQLVQSGAEVKKPGASVKVSCKASGYTFT | -H1- | WVRQAPGQGLEWMG | -H2- | RVTIT |
| B | QVQLVQSGAEVKKPGASVKVSCKAS | -H1- | WVRQAPGQGLEWM | -H2- | RVTIT |
| C | QVQLVQSGAEVKKPGASVKVSCKAS | -H1- | WVRQAPGQGLEWM | -H2- | RVTIT |
| D | QVQLVQSGAEVKKPGASVKVSCKAS | -H1- | WVRQAPGQGLEWM | -H2- | RVTIT |
| II | | | | | |
| A | QVQLQESGPGLVKPSQTLSLTCTVSGGSVS | -H1- | WIRQPPGKGLEWIG | -H2- | RVTIS |
| B | QVQLQESGPGLVKPSQTLSLTCTVS | -H1- | WIRQPPGKGLEWI | -H2- | RVTIS |
| C | QVQLQESGPGLVKPSQTLSLTCTVS | -H1- | WIRQPPGKGLEWI | -H2- | RVTIS |
| D | QVQLQESGPGLVKPSQTLSLTCTVS | -H1- | WIRQPPGKGLEWI | -H2- | RVTIS |
| III | | | | | |
| A | EVQLVESGGGLVQPGGSLRLSCAASGFTFS | -H1- | WVRQAPGKGLEWVS | -H2- | RFTIS |
| B | EVQLVESGGGLVQPGGSLRLSCAAS | -H1- | WVRQAPGKGLEWV | -H2- | RFTIS |
| C | EVQLVESGGGLVQPGGSLRLSCAAS | -H1- | WVRQAPGKGLEWV | -H2- | RFTIS |
| D | EVQLVESGGGLVQPGGSLRLSCAAS | -H1- | WVRQAPGKGLEWV | -H2- | RFTIS |
| Acceptor - 1 | | | | | |
| A | EVQLVESGGGLVQPGGSLRLSCAASGFNIK | -H1- | WVRQAPGKGLEWVS | -H2- | RFTIS |
| B | EVQLVESGGGLVQPGGSLRLSCAAS | -H1- | WVRQAPGKGLEWV | -H2- | RFTIS |
| C | EVQLVESGGGLVQPGGSLRLSCAAS | -H1- | WVRQAPGKGLEWV | -H2- | RFTIS |
| Acceptor - 2 | | | | | |
| A | EVQLVESGGGLVQPGGSLRLSCAASGFNIK | -H1- | WVRQAPGKGLEWVS | -H2- | RFTIS |
| B | EVQLVESGGGLVQPGGSLRLSCAAS | -H1- | WVRQAPGKGLEWV | -H2- | RFTIS |
| C | EVQLVESGGGLVQPGGSLRLSCAAS | -H1- | WVRQAPGKGLEWV | -H2- | RFTIS |
| D | EVQLVESGGGLVQPGGSLRLSCAAS | -H1- | WVRQAPGKGLEWV | -H2- | RFTIS |

FIG. 16A

| | FR3 | | FR4 | SEQ ID NOs of FR1, FR2, FR3, FR4 |
|---|---|---|---|---|
| I | | | | |
| A | ADTSTSTAYMELSSLRSEDTAVYYCAR | -H3- | WGQGTLVTVSS | SEQ ID NO.: 32, 33, 34, 35 |
| B | ADTSTSTAYMELSSLRSEDTAVYYCAR | -H3- | WGQGTLVTVSS | SEQ ID NO.: 36, 37, 34, 35 |
| C | ADTSTSTAYMELSSLRSEDTAVYYCA | -H3- | WGQGTLVTVSS | SEQ ID NO.: 36, 37, 38, 35 |
| D | ADTSTSTAYMELSSLRSEDTAVYYC | -H3- | WGQGTLVTVSS | SEQ ID NO.: 36, 37, 39, 35 |
| II | | | | |
| A | VDTSKNQFSLKLSSVTAADTAVYYCAR | -H3- | WGQGTLVTVSS | SEQ ID NO.: 40, 41, 42, 35 |
| B | VDTSKNQFSLKLSSVTAADTAVYYCAR | -H3- | WGQGTLVTVSS | SEQ ID NO.: 43, 44, 42, 35 |
| C | VDTSKNQFSLKLSSVTAADTAVYYCA | -H3- | WGQGTLVTVSS | SEQ ID NO.: 43, 44, 45, 35 |
| D | VDTSKNQFSLKLSSVTAADTAVYYC | -H3- | WGQGTLVTVSS | SEQ ID NO.: 43, 44, 46, 35 |
| III | | | | |
| A | RDNSKNTLYLQMNSLRAEDTAVYYCAR | -H3- | WGQGTLVTVSS | SEQ ID NO.: 47, 48, 49, 35 |
| B | RDNSKNTLYLQMNSLRAEDTAVYYCAR | -H3- | WGQGTLVTVSS | SEQ ID NO.: 50, 51, 49, 35 |
| C | RDNSKNTLYLQMNSLRAEDTAVYYCA | -H3- | WGQGTLVTVSS | SEQ ID NO.: 50, 51, 52, 35 |
| D | RDNSKNTLYLQMNSLRAEDTAVYYC | -H3- | WGQGTLVTVSS | SEQ ID NO.: 50, 51, 53, 35 |
| Acceptor - 1 | | | | |
| A | ADTSKNTAYLQMNSLRAEDTAVYYCSR | -H3- | WGQGTLVTVSS | SEQ ID NO.: 54, 48, 55, 35 |
| B | ADTSKNTAYLQMNSLRAEDTAVYYCSR | -H3- | WGQGTLVTVSS | SEQ ID NO.: 50, 51, 55, 35 |
| C | ADTSKNTAYLQMNSLRAEDTAVYYCS | -H3- | WGQGTLVTVSS | SEQ ID NO.: 50, 51, 56, 35 |
| Acceptor - 2 | | | | |
| A | ADTSKNTAYLQMNSLRAEDTAVYYCAR | -H3- | WGQGTLVTVSS | SEQ ID NO.: 54, 48, 57, 35 |
| B | ADTSKNTAYLQMNSLRAEDTAVYYCAR | -H3- | WGQGTLVTVSS | SEQ ID NO.: 50, 51, 57, 35 |
| C | ADTSKNTAYLQMNSLRAEDTAVYYCA | -H3- | WGQGTLVTVSS | SEQ ID NO.: 50, 51, 58, 35 |
| D | ADTSKNTAYLQMNSLRAEDTAVYYC | -H3- | WGQGTLVTVSS | SEQ ID NO.: 50, 51, 59, 35 |

FIG. 16B

| | FR1 | | FR2 | | FR3 |
|---|---|---|---|---|---|
| kv1 | DIQMTQSPSSLSASVGDRVTITC | -L1- | WYQQKPGKAPKLLIY | -L2- | GVPSRFSGSGSGTDFTLTISSLQP |
| kv2 | DIVMTQSPLSLPVTPGEPASISC | -L1- | WYLQKPGQSPQLLIY | -L2- | GVPDRFSGSGSGTDFTLKISRVEA |
| kv3 | EIVLTQSPGTLSLSPGERATLSC | -L1- | WYQQKPGQAPRLLIY | -L2- | GIPDRFSGSGSGTDFTLTISRLEP |
| kv4 | DIVMTQSPDSLAVSLGERATINC | -L1- | WYQQKPGQPPKLLIY | -L2- | GVPDRFSGSGSGTDFTLTISSLQA |

| | | FR4 | SEQ ID NOs of FR1, FR2, FR3, FR4 |
|---|---|---|---|
| EDFATYYC | -L3- | FGQGTKVEIK | SEQ ID NO.: 60, 61, 62, 63 |
| EDVGVYYC | -L3- | FGQGTKVEIK | SEQ ID NO.: 64, 65, 66, 63 |
| EDFAVYYC | -L3- | FGQGTKVEIK | SEQ ID NO.: 67, 68, 69, 63 |
| EDVAVYYC | -L3- | FGQGTKVEIK | SEQ ID NO.: 70, 71, 72, 63 |

*FIG. 17*

Framework Sequences of huMAb4D5-8 Light Chain Variable Domain

LC-FR1 $^{1}$Asp Ile Gln Met Thr Gln Ser Pro Ser Ser Leu Ser Ala Ser Val Gly Asp Arg Val Thr Ile Thr Cys$^{23}$ (SEQ ID NO: 60)

LC-FR2 $^{35}$Trp Tyr Gln Gln Lys Pro Gly Lys Ala Pro Lys Leu Leu Ile Tyr$^{49}$ (SEQ ID NO: 61)

LC-FR3 $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO: 30)

LC-FR4 $^{98}$Phe Gly Gln Gly Thr Lys Val Glu Ile Lys$^{107}$ (SEQ ID NO: 63)

Framework Sequences of huMAb4D5-8 Heavy Chain Variable Domain

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 50)

HC-FR2 $^{36}$Trp Val Arg Gln Ala Pro Gly Lys Gly Leu Glu Trp Val$^{48}$ (SEQ ID NO: 51)

HC-FR3 $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$ (SEQ ID NO: 59)

HC-FR4 $^{103}$Trp Gly Gln Gly Thr Leu Val Thr Val Ser Ser$^{113}$ (SEQ ID NO: 35)

FIG. 18

Framework Sequences of huMAb4D5-8 Light Chain Variable Domain Modified at Positions 66 and 99 (Underlined)

LC-FR1 $^{1}$Asp Ile Gln Met Thr Gln Ser Pro Ser Ser Leu Ser Ala Ser Val Gly Asp Arg Val Thr Ile Thr Cys$^{23}$ (SEQ ID NO: 60)

LC-FR2 $^{35}$Trp Tyr Gln Gln Lys Pro Gly Lys Ala Pro Lys Leu Leu Ile Tyr$^{49}$ (SEQ ID NO: 61)

LC-FR3 $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$ (SEQ ID NO: 62)

LC-FR4 $^{98}$Phe <u>Arg</u> Gln Gly Thr Lys Val Glu Ile Lys$^{107}$ (SEQ ID NO: 31)

Framework Sequences of huMAb4D5-8 Heavy Chain Variable Domain Modified at Postions 71, 73 and 78 (Underlined)

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 50)

HC-FR2 $^{36}$Trp Val Arg Gln Ala Pro Gly Lys Gly Leu Glu Trp Val$^{48}$ (SEQ ID NO: 51)

HC-FR3 $^{66}$Arg Phe Thr Ile Ser <u>Arg</u> Asp <u>Asn</u> Ser Lys Asn Thr <u>Leu</u> Tyr Leu Gln Met Asn83 Ser83a Leu83b Arg83c Ala Glu Asp Thr Ala Val Tyr Tyr Cys$^{92}$ (SEQ ID NO: 53)

HC-FR4 $^{103}$Trp Gly Gln Gly Thr Leu Val Thr Val Ser Ser$^{113}$ (SEQ ID NO: 35)

FIG. 19

METHODS OF TREATING LIVER CONDITIONS USING NOTCH2 ANTAGONISTS

CROSS-REFERENCE TO RELATED APPLICATIONS

This application claims the benefit of U.S. Provisional Application No. 61/543,483, filed Oct. 5, 2011, the disclosure of which is incorporated herein by reference as if set forth in its entirety.

SEQUENCE LISTING

This application contains a Sequence Listing, which has been submitted in ASCII format via EFS-Web and is hereby incorporated by reference in its entirety. Said ASCII copy, created on Apr. 26, 2016, is named "GENENLAW-_416567-v1-P4760R1WO_-_Sequence_Listing.TXT" and is 55,095 bytes in size.

FIELD OF THE INVENTION

The present invention relates to methods of treating liver conditions using Notch2 antagonists. Compositions for the treatment of such conditions are also provided.

BACKGROUND

The Notch receptor family is a class of evolutionarily conserved transmembrane receptors that transmit signals affecting development in organisms as diverse as sea urchins and humans. Notch receptors and their ligands Delta and Serrate (known as Jagged in mammals) are transmembrane proteins with large extracellular domains that contain epidermal growth factor (EGF)-like repeats. The number of Notch paralogues differs between species. For example, there are four Notch receptors in mammals (Notch1-Notch4), two in *Caenorhabditis elegans* (LIN-12 and GLP-1) and one in *Drosophila melanogaster* (Notch). Notch receptors are proteolytically processed during transport to the cell surface by a furin-like protease at a site S1, which is N-terminal to the transmembrane domain, producing an extracellular Notch (ECN) subunit and a Notch transmembrane subunit (NTM). These two subunits remain non-covalently associated and constitute the mature heterodimeric cell-surface receptor.

Notch2 ECN subunits contain 36 N-terminal EGF-like repeats followed by three tandemly repeated Lin 12/Notch Repeat (LNR) modules that precede the S1 site. Each LNR module contains three disulfide bonds and a group of conserved acidic and polar residues predicted to coordinate a calcium ion. Within the EGF repeat region lie binding sites for the activating ligands.

The Notch2 NTM comprises an extracellular region (which harbors the S2 cleavage site), a transmembrane segment (which harbors the S3 cleavage site), and a large intracellular portion that includes a RAM23 domain, six ankyrin repeats, a transactivation domain and a carboxy-terminal PEST sequence. Stable association of the ECN and NTM subunits is dependent on a heterodimerization domain (HD) comprising the carboxy-terminal end of the ECN (termed HD-N) and the extracellular amino-terminal end of NTM (termed HD-C). Before ligand-induced activation, Notch is maintained in a resting conformation by a negative regulatory region (NRR), which comprises the three LNRs and the HD domain. The crystal structure of the Notch2 NRR is reported in Gordon et al., (2007) *Nature Structural & Molecular Biology* 14:295-300, 2007.

Binding of a Notch ligand to the ECN subunit initiates two successive proteolytic cleavages that occur through regulated intramembrane proteolysis. The first cleavage by a metalloprotease (ADAM17) at site S2 renders the Notch transmembrane subunit susceptible to a second cleavage at site S3 close to the inner leaflet of the plasma membrane. Site S3 cleavage, which is catalyzed by a multiprotein complex containing presenilin and nicastrin and promoting γ-secretase activity, liberates the intracellular portion of the Notch transmembrane subunit, allowing it to translocate to the nucleus and activate transcription of target genes. (For review of the proteolytic cleavage of Notch, see, e.g., Sisodia et al., *Nat. Rev. Neurosci.* 3:281-290, 2002.)

Five Notch ligands of the Jagged and Delta-like classes have been identified in humans (Jagged1 (also termed Serrate1), Jagged2 (also termed Serrate2), Delta-like1 (also termed DLL1), Delta-like3 (also termed DLL3), and Delta-like4 (also termed DLL4)). Each of the ligands is a single-pass transmembrane protein with a conserved N-terminal Delta, Serrate, LAG-2 (DSL) motif essential for binding Notch. A series of EGF-like modules C-terminal to the DSL motif precede the membrane-spanning segment. Unlike the Notch receptors, the ligands have short cytoplasmic tails of 70-215 amino acids at the C-terminus. In addition, other types of ligands have been reported (e.g., DNER, NB3, and F3/Contactin). (For review of Notch ligands and ligand-mediated Notch activation, see, e.g., D'Souza et al., *Oncogene* 27:5148-5167, 2008.)

The Notch pathway functions during diverse developmental and physiological processes including those affecting neurogenesis in flies and vertebrates. In general, Notch signaling is involved in lateral inhibition, lineage decisions, and the establishment of boundaries between groups of cells. (See, e.g., Bray, *Mol. Cell Biol.* 7:678-679, 2006.) A variety of human diseases, including cancers and neurodegenerative disorders have been shown to result from mutations in genes encoding Notch receptors or their ligands. (See, e.g., Nam et al., *Curr. Opin. Chem. Biol.* 6:501-509, 2002.)

Certain anti-Notch2 antagonist antibodies having therapeutic efficacy have been described. (See U.S. Patent Application Publication No. US 2009/0081238 A1, expressly incorporated by reference in its entirety herein.) For example, such antibodies bind to the negative regulatory region (NRR) of Notch2, block Notch2 signaling, and inhibit the growth of melanoma cell lines, diffuse large B-cell lymphoma (DLBCL) cell lines, and marginal zone B cells. Certain anti-Notch2 antibodies described therein bind to the LNR-A domain (the first of the three LIN12/Notch Repeats) and the HD-C domain of Notch2 NRR.

Adult liver has the capacity to regenerate after injury. It has been speculated that biliary-hepatocyte progenitor cells (oval cells) in or near intrahepatic bile ducts can differentiate into adult hepatocytes (Brues and Marble, J. Exp. Med., 65(1):15 (1937); Zajicek et al., Liver, 5(6):293 (1985)), which subsequently mature as they move toward the central vein and eventually undergo apoptosis and elimination (Benedetti et al., J. Hepatol., 7(3):319 (1988)). Recent lineage-tracing studies have supported a role of progenitor cells in liver homeostasis and repair, but the signals that govern precursor differentiation into hepatocytes are poorly understood. While Notch signaling is known to be critical for the proper formation of the intrahepatic biliary system during development (Lozier et al., PLoS One 3(3):e1851 (2008); McCright et al., Development 129(4):1075 (2002)), it was not known what role, if any, Notch signaling plays in adult hepatocyte formation and in adult hepatobiliary disease.

Chronic liver disease is marked by gradual destruction of liver tissue, especially of hepatocytes and the functional lobular unit, leading to fibrosis (replacement of liver tissue with scar tissue) and cirrhosis (fibrosis with ineffective nodular regeneration and associated loss of liver function). Moreover, chronic liver disease often includes pathological biliary hyperplasia and may increase the risk of liver cancer.

There is a need in the art for further therapeutic methods of treating liver conditions. The invention described herein meets the above-described needs and provides other benefits.

SUMMARY

The present invention relates to the treatment of liver conditions using Notch2 antagonists. The present invention is based, in part, on the observation that anti-Notch2 NRR antibodies (a) improve liver histologic appearance and hepatocyte function in an acute liver damage model in vivo and (b) reduce biliary damage and improve hepatocyte function in a chronic liver damage model in vivo.

In one aspect, a method of treating a liver condition characterized by liver damage is provided, the method comprising administering to a patient having such condition an effective amount of a Notch2-specific antagonist. In certain embodiments, the liver condition is chronic liver disease. In certain embodiments, the liver condition is liver fibrosis.

In any of the above embodiments, the Notch2-specific antagonist may be an anti-Notch2 antagonist antibody. In certain embodiments, the anti-Notch2 antagonist antibody is an anti-Notch2 NRR antibody. In one such embodiment, the anti-Notch2 NRR antibody binds to the LNR-A and HD-C domains of Notch2 NRR. In another such embodiment, the anti-Notch2 NRR antibody is Antibody D, Antibody D-1, Antibody D-2, or Antibody D-3. In another such embodiment, the anti-Notch2 NRR antibody comprises the heavy and light chain variable region CDRs of Antibody D, Antibody D-1, Antibody D-2, or Antibody D-3. In certain embodiments, the anti-Notch2 antagonist antibody is an anti-Notch2 antibody that binds to one or more EGF-like repeats of Notch2.

The above and further aspects and embodiments of the invention are provided herein.

BRIEF DESCRIPTION OF THE FIGURES

FIGS. 3A-J show that inhibition of Notch2 signaling in vivo promotes hepatocyte differentiation and improved liver function in chronic and acute liver damage models.

FIG. 12 shows the H1, H2, and H3 heavy chain hypervariable region (HVR) sequences of anti-Notch2 NRR monoclonal antibodies designated Antibody D, Antibody D-1, Antibody D-2, and Antibody D-3. Amino acid positions are numbered according to the Kabat numbering system as described below.

FIG. 13 shows the L1, L2, and L3 light chain HVR sequences of anti-Notch2 NRR monoclonal antibodies designated Antibody D, Antibody D-1, Antibody D-2, and Antibody D-3. Amino acid positions are numbered according to the Kabat numbering system as described below.

FIG. 14 shows an alignment of the heavy chain variable region sequences of Antibody D, Antibody D-1, Antibody D-2, and Antibody D-3. HVRs are enclosed in boxes.

FIG. 15 shows an alignment of the light chain variable region sequences of Antibody D, Antibody D-1, Antibody D-2, and Antibody D-3. HVRs are enclosed in boxes.

FIGS. 16A-B show exemplary acceptor human variable heavy (VH) consensus framework sequences for use in practicing the instant invention. Sequence identifiers are as follows:

Figure 1A:
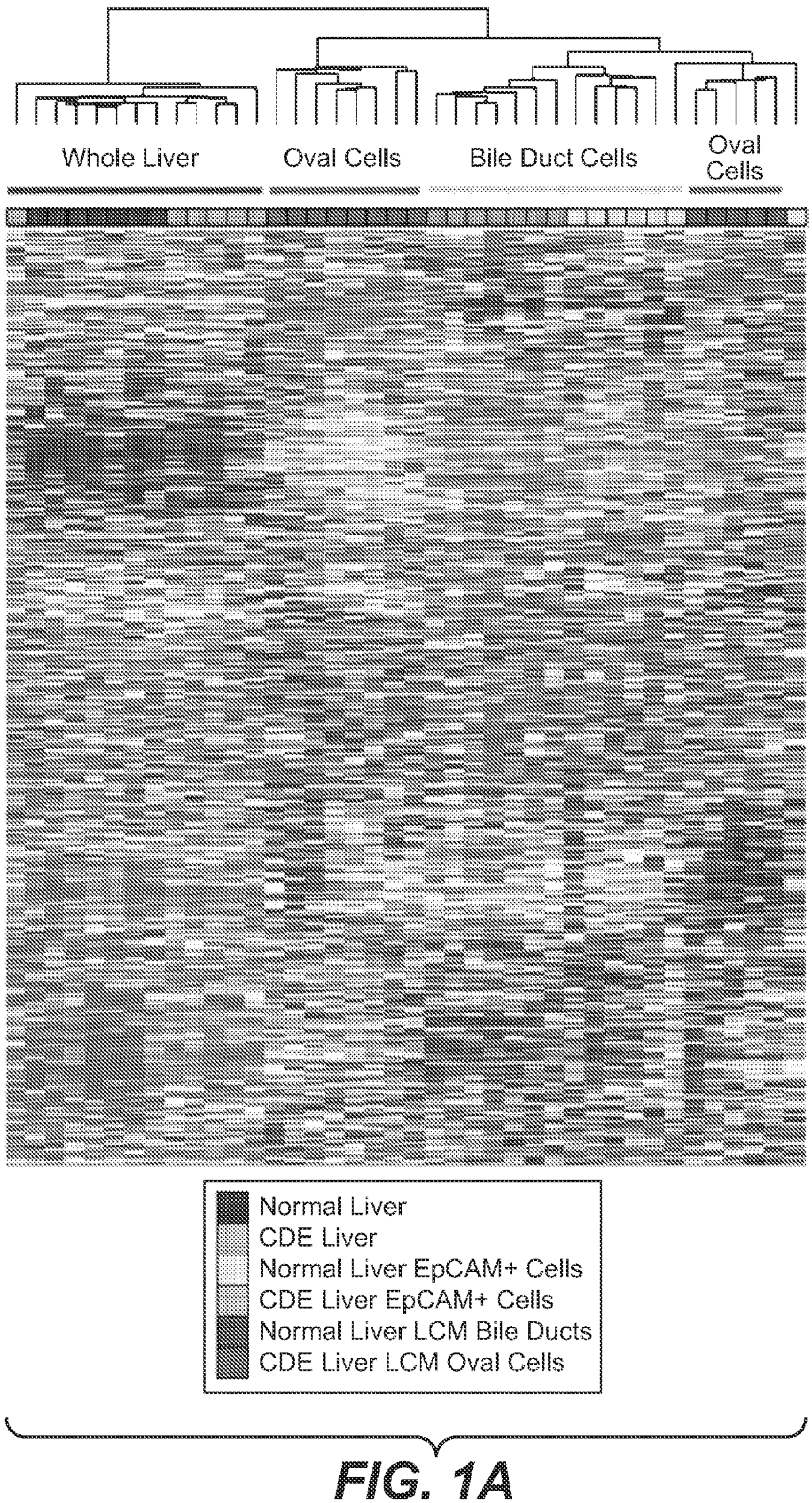
FIGS. 1A-G show transcriptional profiling of hepatic progenitor cells and Identification of active Notch signaling in hepatic progenitors in vivo.

- human VH subgroup I consensus framework "A" minus Kabat CDRs (SEQ ID NOs:32, 33, 34, 35).
- human VH subgroup I consensus frameworks "B," "C," and "D" minus extended hypervariable regions (SEQ ID NOs:36, 37, 34, 35; SEQ ID NOs:36, 37, 38, 35; and SEQ ID NOs:36, 37, 39, 35).
- human VH subgroup II consensus framework "A" minus Kabat CDRs (SEQ ID NOs:40, 41, 42, 35).
- human VH subgroup II consensus frameworks "B," "C," and "D" minus extended hypervariable regions (SEQ ID NOs:43, 44, 42, 35; SEQ ID NOs:43, 44, 45, 35; and SEQ ID NOs:43, 44, 46, and 35).
- human VH subgroup III consensus framework "A" minus Kabat CDRs (SEQ ID NOs:47, 48, 49, 35).
- human VH subgroup III consensus frameworks "B," "C," and "D" minus extended hypervariable regions (SEQ ID NOs:50, 51, 49, 35; SEQ ID NOs:50, 51, 52, 35; and SEQ ID NOs:50, 51, 53, 35).
- human VH acceptor framework "A" minus Kabat CDRs (SEQ ID NOs:54, 48, 55, 35).
- human VH acceptor frameworks "B" and "C" minus extended hypervariable regions (SEQ ID NOs:50, 51, 55, 35; and SEQ ID NOs:50, 51, 56, 35).
- human VH acceptor 2 framework "A" minus Kabat CDRs (SEQ ID NOs:54, 48, 57, 35).
- human VH acceptor 2 framework "B," "C," and "D" minus extended hypervariable regions (SEQ ID NOs: 50, 51, 57, 35; SEQ ID NOs:50, 51, 58, 35; and SEQ ID NOs:50, 51, 59, 35).

FIG. 17 shows exemplary acceptor human variable light (VL) consensus framework sequences for use in practicing the instant invention. Sequence identifiers are as follows:

human VL kappa subgroup I consensus framework (κv1): SEQ ID NOs:60, 61, 62, 63 human VL kappa subgroup II consensus framework (κv2): SEQ ID NOs:64, 65, 66, 63 human VL kappa subgroup III consensus framework (κv3): SEQ ID NOs:67, 68, 69, 63 human VL kappa subgroup IV consensus framework (κv4): SEQ ID NOs:70, 71, 72, 63

FIG. 18 shows framework sequences of huMAb4D5-8 light and heavy chains. Numbers in superscript/bold indicate amino acid positions according to Kabat.

FIG. 19 shows framework sequences of huMAb4D5-8 light and heavy chains with the indicated modifications. Numbers in superscript/bold indicate amino acid positions according to Kabat.

DETAILED DESCRIPTION OF EMBODIMENTS

I. Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

The term "Notch," as used herein, refers, unless specifically or contextually indicated otherwise, to any native or variant (whether native or synthetic) Notch polypeptide (Notch1-4). The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type Notch" generally refers to a polypeptide comprising an amino acid sequence of a naturally occurring, non-mutated Notch protein. The term "wild-type Notch sequence" generally refers to an amino acid sequence found in a naturally occurring, non-mutated Notch.

The term "Notch2," as used herein, refers, unless specifically or contextually indicated otherwise, to any native or variant (whether native or synthetic) Notch2 polypeptide. The term "native sequence" specifically encompasses naturally occurring truncated forms (e.g., an extracellular domain sequence or a transmembrane subunit sequence), naturally occurring variant forms (e.g., alternatively spliced forms) and naturally occurring allelic variants. The term "wild-type Notch2" generally refers to a polypeptide comprising an amino acid sequence of a naturally occurring, non-mutated Notch2 protein. The term "wild type Notch2 sequence" generally refers to an amino acid sequence found in a naturally occurring, non-mutated Notch2.

The term "Notch2 ligand," as used herein, refers, unless specifically or contextually indicated otherwise, to any native or variant (whether native or synthetic) Notch2 ligand (for example, Jagged1, Jagged2, Delta-like1, Delta-like3, and/or Delta-like4) polypeptide. The term "native sequence" specifically encompasses naturally occurring truncated forms (e.g., an extracellular domain sequence or a transmembrane subunit sequence), naturally occurring variant forms (e.g., alternatively spliced forms) and naturally occurring allelic variants. The term "wild-type Notch2 ligand" generally refers to a polypeptide comprising an amino acid sequence of a naturally occurring, non-mutated Notch2 ligand. The term "wild type Notch2 ligand sequence" generally refers to an amino acid sequence found in a naturally occurring, non-mutated Notch2 ligand.

The term "Notch2 NRR," as used herein, refers, unless specifically or contextually indicated otherwise, to any native or variant (whether native or synthetic) polypeptide region of Notch2 consisting of the 3 LNR modules and the amino acid sequences extending from the carboxy-terminus of the LNR modules to the transmembrane domain, such sequences including the HD domain (HD-N and HD-C). An exemplary Notch2 NRR consists of the region from about amino acid 1422-1677 of human Notch2 (SEQ ID NO:73). An exemplary human Notch2 NRR is also shown in SEQ ID NO:74. The term "native sequence Notch2 NRR" specifically encompasses naturally occurring truncated forms, naturally occurring variant forms (e.g., alternatively spliced forms) and naturally-occurring allelic variants of a Notch2 NRR. The term "wild-type Notch2 NRR" generally refers to a naturally occurring, non-mutated Notch2 NRR. In some embodiments, a Notch2 NRR is contained in a Notch2, such as, for example, a Notch2 processed at the 51, S2 and/or S3 site(s), or an unprocessed Notch2. In some embodiments, a Notch2 NRR contains two or more non-covalently linked fragments of a Notch2 NRR amino acid sequence, e.g., a fragment containing amino acids 1422 to 1608 of SEQ ID NO:73 non-covalently linked to a fragment containing amino acids 1609 to 1677 of SEQ ID NO:73.

The term "increased Notch2 signaling," as used herein, refers to an increase in Notch2 signaling that is significantly above the level of Notch2 signaling observed in a control under substantially identical conditions. In certain embodiments, the increase in Notch2 signaling is at least two fold, three fold, four fold, five fold, or ten fold above the level observed in the control.

The term "decreased Notch1 signaling," as used herein, refers to a decrease in Notch2 signaling that is significantly below the level of Notch2 signaling observed in a control under substantially identical conditions. In certain embodiments, the decrease in Notch2 signaling is at least two fold, three fold, four fold, five fold, or ten fold below the level observed in the control.

In certain embodiments, Notch2 signaling (i.e., increased or decreased Notch2 signaling) is assessed using a suitable reporter assay, e.g, as described in U.S. Patent Application Publication No. US 2010/0080808 A1.

The term "anti-Notch2 antibody" or "an antibody that binds to Notch2" refers to an antibody that is capable of binding Notch2 with sufficient affinity such that the antibody is useful as a diagnostic and/or therapeutic agent in targeting Notch2. Preferably, the extent of binding of an anti-Notch2 antibody to an unrelated, non-Notch protein is less than about 10% of the binding of the antibody to Notch2 as measured, e.g., by a radioimmunoassay (RIA). In certain embodiments, an antibody that binds to Notch2 has a dissociation constant (Kd) of ≤1 μM, ≤0.5 μM, ≤100 nM, ≤50 nM, ≤10 nM, ≤5 nM, ≤1 nM, ≤0.5 nM, or ≤0.1 nM. In certain embodiments, an anti-Notch2 antibody binds to an epitope of Notch2 that is conserved among Notch2 from different species, e.g., rodents (mice, rats) and primates.

The term "anti-Notch2 NRR antibody" or "an antibody that binds to Notch2 NRR" refers to an antibody that is capable of binding Notch2 NRR with sufficient affinity such that the antibody is useful as a diagnostic and/or therapeutic agent in targeting Notch2. Preferably, the extent of binding of an anti-Notch2 NRR antibody to an unrelated, non-Notch protein is less than about 10% of the binding of the antibody to Notch2 NRR as measured, e.g., by a radioimmunoassay (RIA). In certain embodiments, an antibody that binds to Notch2 NRR has a dissociation constant (Kd) of ≤1 μM, ≤0.5 μM, ≤100 nM, ≤50 nM, ≤10 nM, ≤5 nM, ≤1 nM, ≤0.5 nM, or ≤0.1 nM. In certain embodiments, an anti-Notch2 NRR antibody binds to an epitope of Notch that is conserved among Notch from different species, e.g., rodents (mice, rats) and primates.

The term "Notch2-specific antagonist" refers to an agent that effects decreased Notch2 signaling, as defined above, and does not significantly affect signaling by another Notch receptor (Notch1, 3, or 4 in mammals).

An "anti-Notch2 antagonist antibody" is an anti-Notch2 antibody (including an anti-Notch2 NRR antibody) that effects decreased Notch2 signaling, as defined above.

The term "antagonist" refers to an agent that significantly inhibits (either partially or completely) the biological activity of a target molecule.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and U.S. Pat. No. 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147(1):86-95 (1991). See also van Dijk and van de Winkel, *Curr. Opin. Pharmacol.,* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see United States Patent Application Publication US 2008/0181888 A1, Figures for EU numbering).

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. *Bio/Technology* 10:779-783 (1992) describe affinity maturation by VH and VL domain shuffling. Random mutagenesis of HVR and/or framework residues is described by, for example, in Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, the Kd or Kd value is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN-20™ surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6\ M^{-1}\ s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

An "on-rate," "rate of association," "association rate," or "$k_{on}$" according to this invention can also be determined as described above using a BIACORE®-2000 or a BIACORE®-3000 system (BIAcore, Inc., Piscataway, N.J.).

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

An "acceptor human framework" or a "human acceptor framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferably those changes occur at only three, two, or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., supra. In one embodiment, for the VL, the subgroup is subgroup kappa I as in Kabat et al., supra. In one embodiment, for the VH, the subgroup is subgroup III as in Kabat et al., supra.

A "VH subgroup III consensus framework" comprises the consensus sequence obtained from the amino acid sequences in variable heavy subgroup III of Kabat et al., supra. In one embodiment, a human acceptor framework is derived from the VH subgroup III consensus framework and comprises an amino acid sequence comprising at least a portion or all of each of the following sequences: (SEQ ID NO:50)-H1-(SEQ ID NO:51)-H2-(SEQ ID NO:57 or 59)-H3-(SEQ ID NO: 35). In some embodiments, the last residue (S11) of SEQ ID NO:35 is substituted with an alanine A "VL subgroup I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: (SEQ ID NO:60)-L1-(SEQ ID NO:61)-L2-(SEQ ID NO:62)-L3-(SEQ ID NO:63).

A "disorder" is any condition or disease that would benefit from treatment with a composition or method of the invention. This includes chronic and acute disorders including those pathological conditions which predispose the mammal to the disorder in question. Non-limiting examples of disorders to be treated herein include conditions such as cancer.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

A cancer that "responds" to a therapeutic agent is one that shows a significant decrease in cancer or tumor progression, including but not limited to, (1) inhibition, to some extent, of tumor growth, including slowing down and complete growth arrest; (2) reduction in the number of cancer or tumor cells; (3) reduction in tumor size; (4) inhibition (i.e., reduction, slowing down or complete stopping) of cancer cell infiltration into adjacent peripheral organs and/or tissues; and/or (5) inhibition (i.e. reduction, slowing down or complete stopping) of metastasis.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, Notch2 antagonists of the invention are used to delay development of a disease or disorder or to slow the progression of a disease or disorder.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

The term "pharmaceutical formulation" refers to a preparation which is in such form as to permit the biological activity of the active ingredient to be effective, and which contains no additional components which are unacceptably toxic to a subject to which the formulation would be administered. Such formulations may be sterile.

An "effective amount" refers to an amount effective, at dosages and for periods of time necessary, to achieve the desired therapeutic or prophylactic result.

The term "progenitor," "hepatic progenitor," "liver progenitor" or "oval cell" refers to small epithelial cells that can differentiate into both hepatocytes and intra-hepatic bile duct cells.

II. Embodiments of the Invention

The present invention relates to the treatment of liver conditions using Notch2 antagonists. The present invention is based, in part, on the observation that anti-Notch2 NRR antibodies (a) improve liver appearance and hepatocyte function in an acute liver damage model in vivo and (b) reduce biliary damage and improve hepatocyte function in a chronic liver damage model in vivo. Without being bound by any particular theory or operation, the Notch2 antagonist might improve liver conditions by promoting hepatocyte differentiation and/or by decreasing aberrant bile duct proliferation.

In various aspects of the invention, a method of treating a liver condition characterized by liver damage is provided, the method comprising administering to a patient having such condition an effective amount of a Notch2-specific antagonist. In certain embodiments, the liver condition is chronic liver disease, including but not limited to fibrosis, cirrhosis, viral hepatitis (e.g., hepatitis A, B, C, D, E, or G), autoimmune liver diseases (e.g., autoimmune hepatitis, primary biliary cirrhosis, or primary sclerosing cholangitis), genetic liver diseases (e.g., alpha-1 antitrypsin deficiency, Crigler-Najjar syndrome, familial amyloidosis, Gilbert's syndrome, Dubin-Johnson syndrome, hereditary hemchromatosis, primary oxalosis, or Wilson's disease), alcoholic hepatitis or nonalcoholic fatty liver disease. In certain embodiments, the liver condition is an acute liver condition, such as acute liver failure, acute liver injury, or acute liver toxicity, e.g., acetaminophen toxicity. In certain embodiments, the liver condition is liver cancer, e.g., hepatocellular carcinoma (HCC), intrahepatic cholangiocarcinoma (bile duct cancer), or hepatoblastoma.

In some embodiments, treatment results in improved liver histological appearance, including but not limited to, e.g., larger cell size, lower nuclear-to-cytoplasmic ratio, two nuclei, as compared to cell size, nuclear-to-cytoplasmic ration and nuclei number in cultured adult oval cells. In some embodiments, treatment results in a more differentiated morphology, e.g., as compared to morphology of cultured adult oval cells.

In some embodiments, treatment results in decreased expression of Keratin-19 biomarker in liver cells, e.g., decreased expression relative to expression of Keratin-19 biomarker in cultured adult oval cells. Methods for detecting keratin-19 biomarker (e.g., Keratin-19 gene expression, e.g., mRNA expression) are well known in the art and are also exemplified herein.

In some embodiments, treatment results in increased expression of albumin and AFP e.g., increased expression relative to expression of albumin and/or AFP biomarkers in cultured adult oval cells. Methods for detecting albumin and/or AFP biomarkers (e.g., gene expression, e.g., mRNA expression) are well known in the art and are also exemplified herein.

In some embodiments, treatment results in a reduced number of Hes1 positive intrahepatic bile duct cells.

In some embodiment, treatment results in reduced liver progenitor cells (e.g., adult liver oval cell) proliferation within the bile ducts. Reduced proliferation may be determined, e.g., by determining average cross-sectional area of K19-positive tissue as compared to the total liver cross sectional area.

In some embodiments, treatment results in improved hepatocyte function. Hepatocyte function may be measured by methods known in the art, including but not limited to: no significant elevation of biomarkers associated with biliary dysfunction, such as those biomarkers described in FIG. 11. In some embodiments, a biomarker associated with biliary dysfunction is total and/or direct serum bilirubin level. In some embodiments, a biomarker associated with biliary dysfunction is the differentiation quotient, as further described and exemplified herein.

Figure 5A:
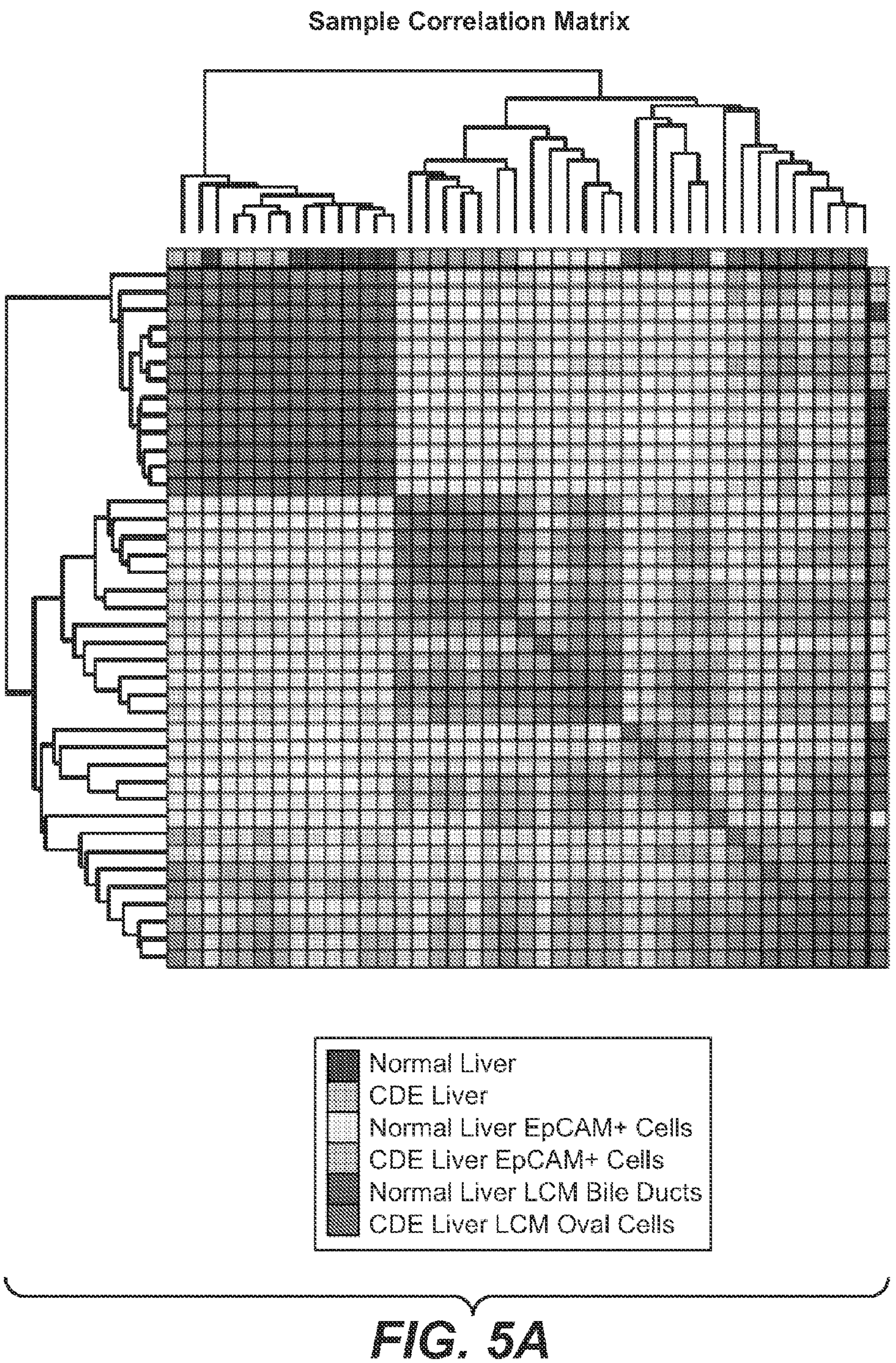
FIGS. 5A-H show an analysis of oval cell-specific gene expression signature.
Figure 5B:
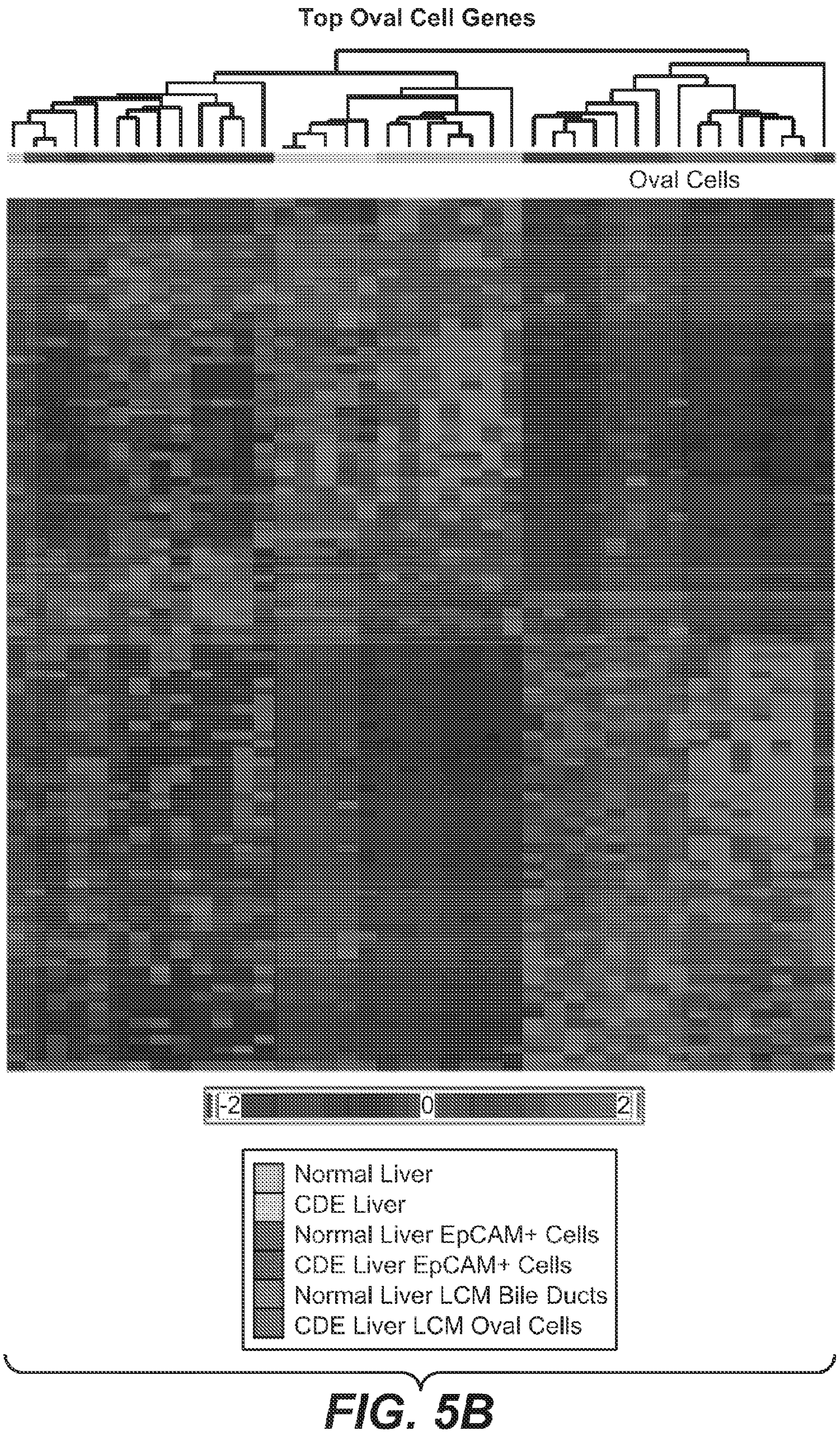
Figure 5C:
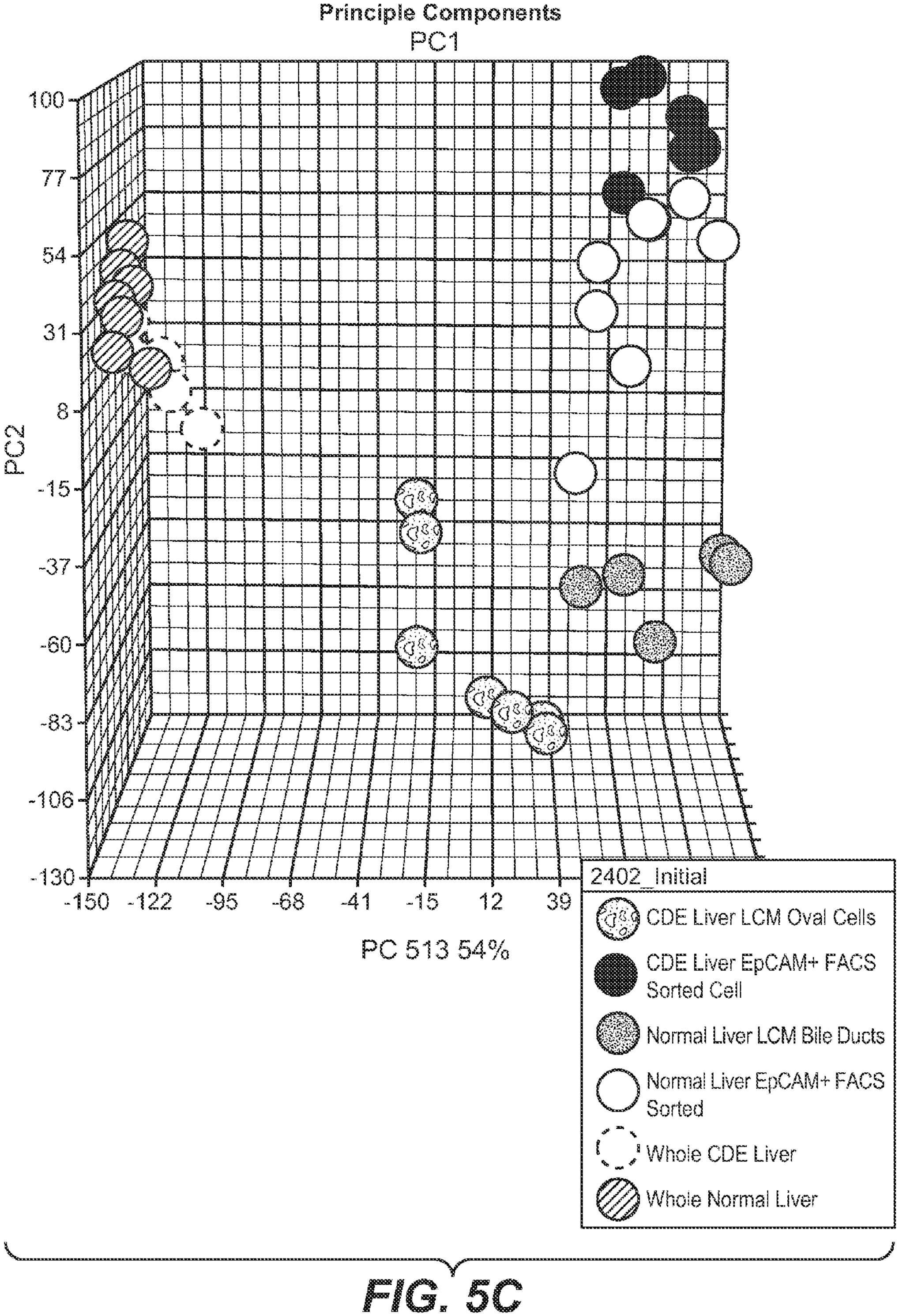
Figure 5D:
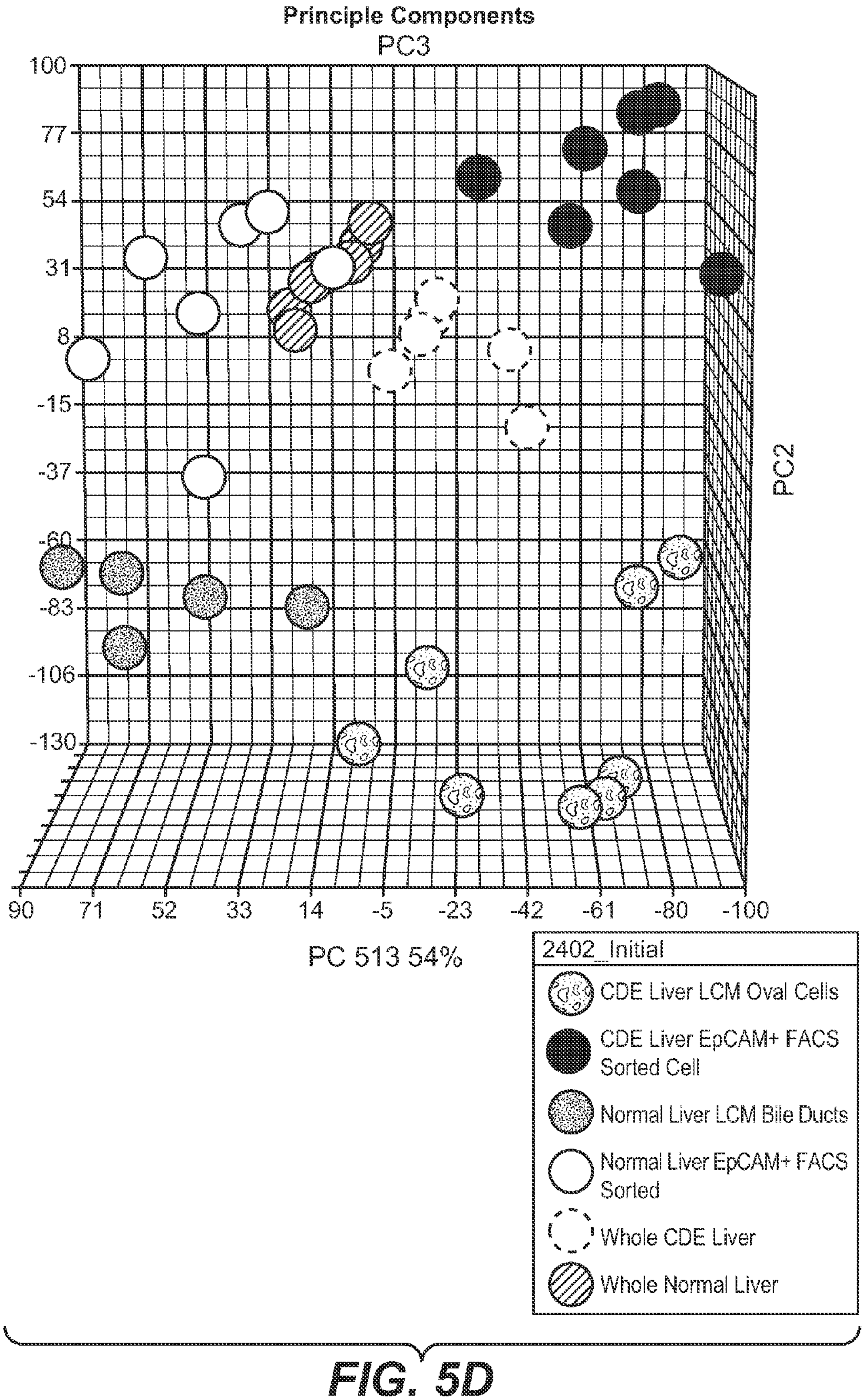
Figure 5E:
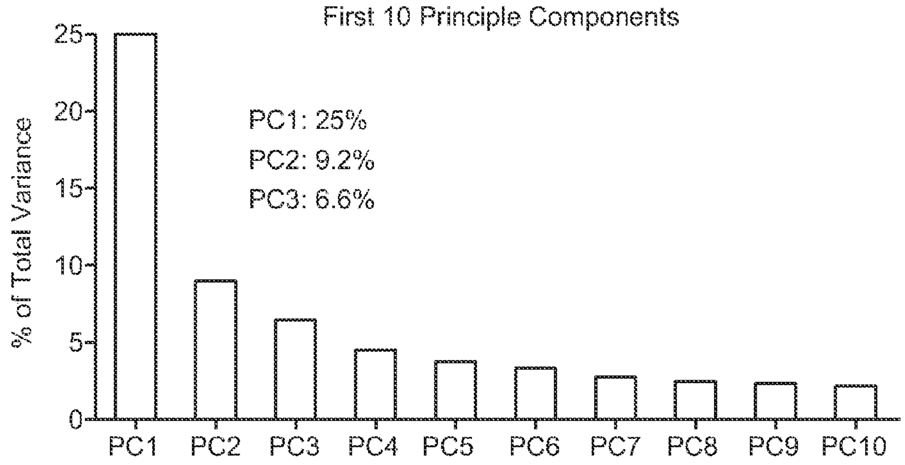
Figure 5F:
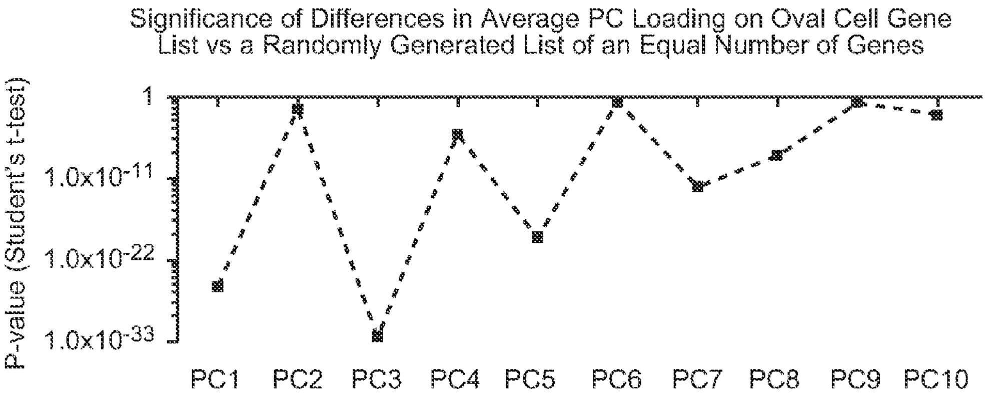
Figure 5G:
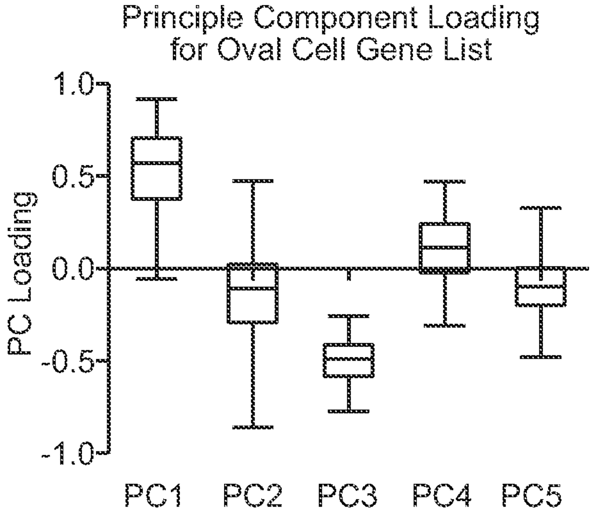
Figure 5H:
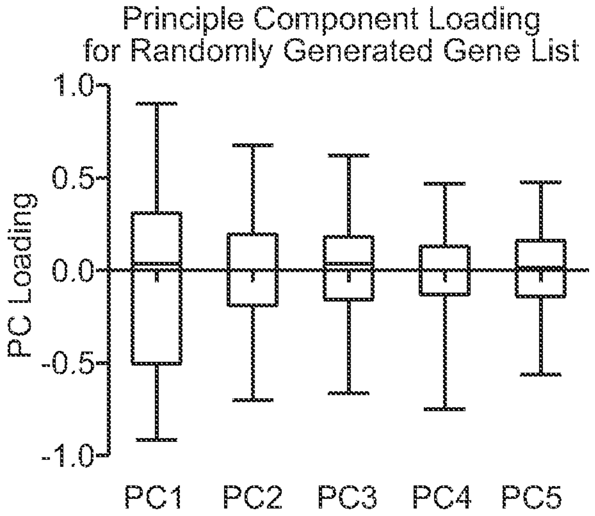
Figures 1, 6A:
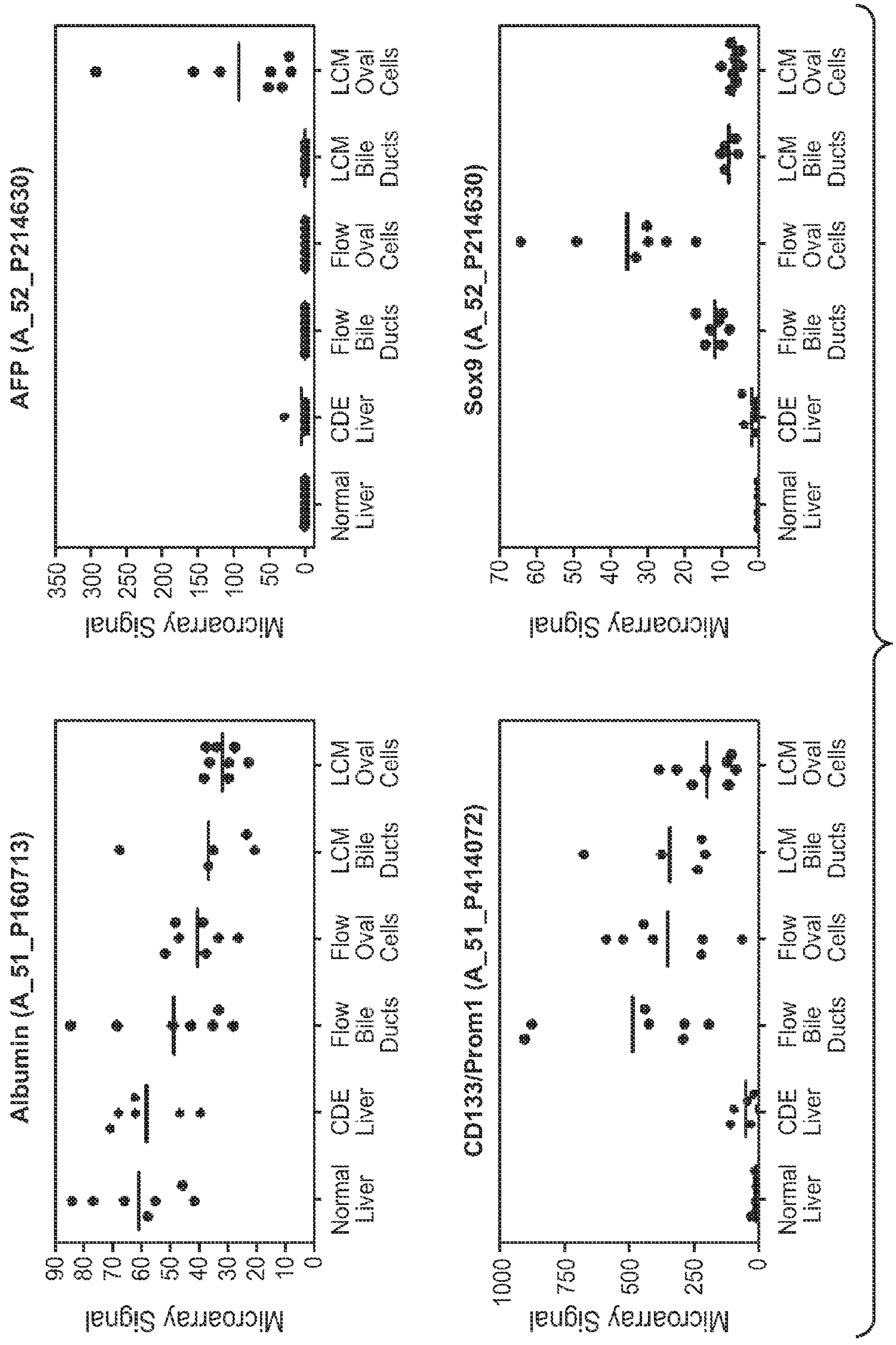
FIGS. 6A-E show a validation of oval cell gene signature and expression pattern of putative hepatic stem cell markers.
Figures 2, 6A:
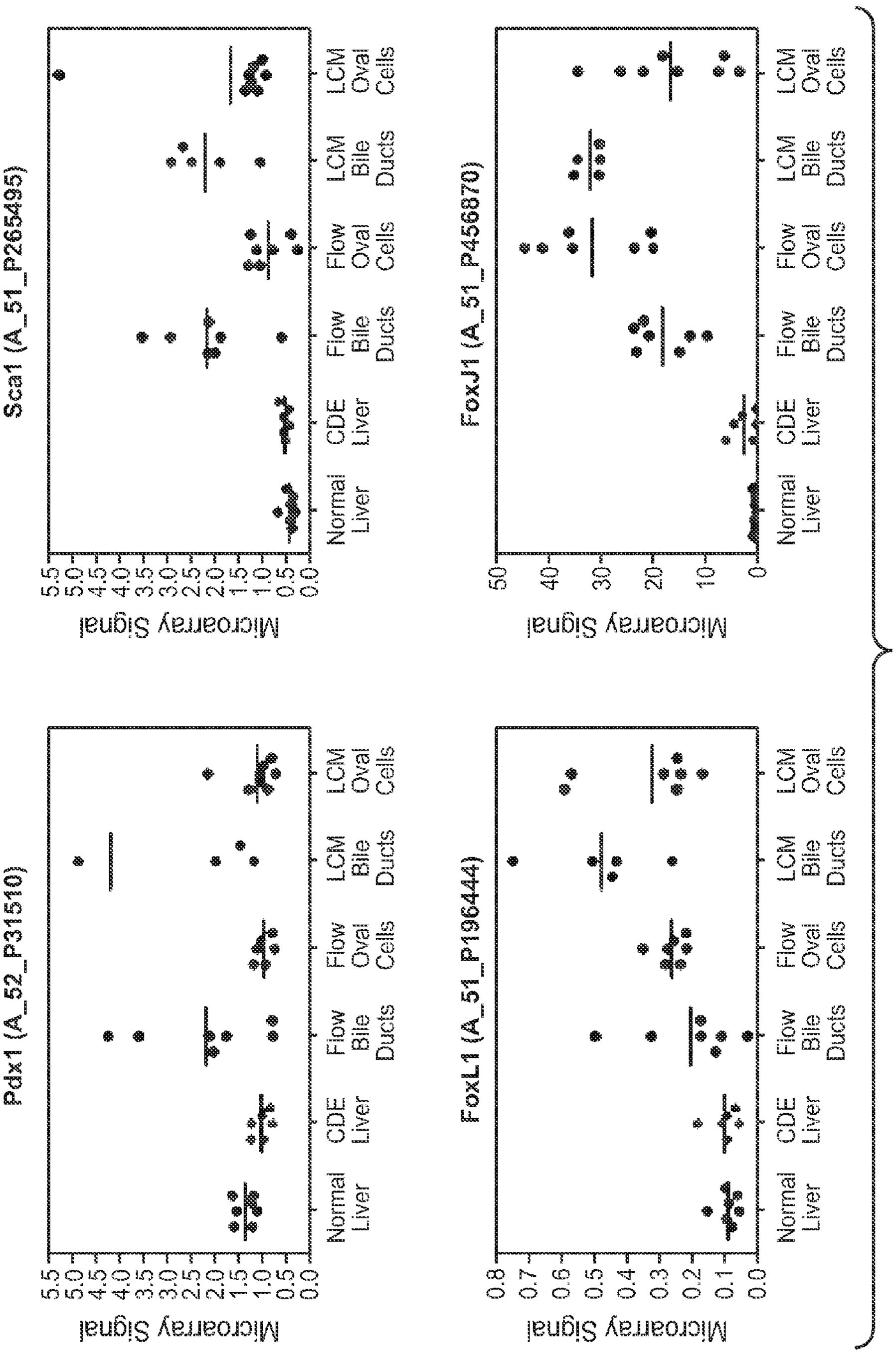

In some embodiments, improved hepatocyte function is determined, e.g., by assessment of heptobiliary function biomarkers, including but not limited to the serum heptobiliary function biomarker described in FIGS. 2 and 5. In some embodiments, serum heptobiliary function biomarker is serum albumin level.

In some embodiments, improved hepatocyte function is increased rate of recovery of liver function.

The invention also provides methods for promoting hepatocyte differentiation and/or by decreasing aberrant bile duct proliferation, the method comprising administering to a patient in need of such treatment an effective amount of a Notch2-specific antagonist. In some embodiments, the patient has a liver condition characterized by liver damage. In certain embodiments, the liver condition is chronic liver disease, including but not limited to fibrosis, cirrhosis, viral hepatitis (e.g., hepatitis A, B, C, D, E, or G), autoimmune liver diseases (e.g., autoimmune hepatitis, primary biliary cirrhosis, or primary sclerosing cholangitis), genetic liver diseases (e.g., alpha-1 antitrypsin deficiency, Crigler-Najjar syndrome, familial amyloidosis, Gilbert's syndrome, Dubin-Johnson syndrome, hereditary hemchromatosis, primary oxalosis, or Wilson's disease), alcoholic hepatitis or nonalcoholic fatty liver disease. In certain embodiments, the liver condition is an acute liver condition, such as acute liver failure, acute liver injury, or acute liver toxicity, e.g., acetaminophen toxicity. In certain embodiments, the liver condition is liver cancer, e.g., hepatocellular carcinoma (HCC), intrahepatic cholangiocarcinoma (bile duct cancer), or hepatoblastoma. In some embodiment, treatment results in reduced liver progenitor cell (e.g., adult liver oval cell) proliferation. Reduced proliferation may be determined, e.g., by determining average cross-sectional area of K19 positive tissue as compared to the total liver cross sectional area.

The invention also provides methods for improving liver histological appearance, the method comprising administering to a patient in need of such treatment an effective amount of a Notch2-specific antagonist. In some embodiments, treatment results in improved liver histological appearance, including but not limited to: larger cell size, lower nuclear-to-cytoplasmic ratio, two nucleic, e.g., as compared to cell size, nuclear-to-cytoplasmic ratio and nuclei number in cultured adult oval cells. In some embodiments, treatment results in a more differentiated morphology, e.g., as compared to morphology of cultured adult oval cells.

In some embodiments, treatment results in decreased expression of Keratin-19 biomarker in liver cells, e.g., decreased expression relative to expression of Keratin-19 biomarker in cultured adult oval cells. Methods for detecting keratin-19 biomarker (e.g., Keratin-19 gene expression, e.g., mRNA expression) are well known in the art and are also exemplified herein.

In some embodiments, treatment results in increased expression of albumin and AFP e.g., increased expression relative to expression of albumin and/or AFP biomarkers in cultured adult oval cells. Methods for detecting albumin and/or AFP biomarkers (e.g., gene expression, e.g., mRNA expression) are well known in the art and are also exemplified herein.

In some embodiments, treatment results in reduced number of Hes1 positive intrahepatic bile duct cells.

The invention also provides methods for reducing serum bile acids, serum bilirubin, serum alkaline phosphatase, serum ALT, and/or serum AST following hepatic injury, the method comprising administering to a patient in need thereof an effective amount of a Notch2-specific antagonist.

The invention also provides methods for reducing the number of CK19-positive cells in cell population that comprises an oval cell, the method comprising the step of contacting the oval cell with a Notch2-specific antagonist.

The invention also provides methods for reducing the expression or secretion of bile acids, bilirubin, alkaline phosphatase, ALT, and/or AST, the method comprising contacting an oval cell with an effective amount of a Notch2-specific antagonist.

The invention provides methods for identifying a patient eligible for receiving treatment of a liver condition characterized by liver damage by administering to a patient having such condition an effective amount of a Notch2-specific antagonist, the method comprising determining expression of one or more of the genes listed in Table 2 in a sample obtained from the patient. In some embodiments, the genes belong to the Notch pathway, e.g., JAG1. In some embodiments, a sample or biopsy from the patient is analyzed for mRNA expression of one of the genes listed in Table 1 using methods well known in the art, such as, e.g., quantitative PCR analysis, and compared to expression of the same gene or genes in a biopsy obtained from a control individual or compared to a reference value. In some embodiments, elevated expression of one or more genes listed in Table 1 in the biopsy obtained from the patient, relative to the control, identifies the patient as suitable for receiving treatment with a Notch2-specific antagonist, as described herein. In some embodiments, additional parameters, such as, e.g., examination by a physician, histologic evaluation of a biopsy, determination of serum levels indicative of liver damage, etc. are employed to identify the patient for receiving the treatment. Also, elevated hepatic expression by a patient of one or more of the genes identified in Table 2 is specifically contemplated as one possible embodiment of any of the methods provided herein.

In some embodiments patients are selected for treatment with a Notch2-specific antagonist as described herein by measuring other known markers of oval cells or aggressive HCC (see, e.g., Woo et al 2011 Mol Carcinog. 2011 April; 50(4):235-43). In some embodiments, patients are selected for treatment by analyzing hepatic Notch2 activation, for example by detection of the activated form of Notch2 as described herein.

Examples of Notch2-specific antagonists include, but are not limited to, soluble Notch receptors, soluble Notch ligand variants, e.g., dominant negative ligand variants, aptamers or oligopeptides that bind Notch2 or Notch2 ligands, organic or inorganic molecules that interfere specifically with Notch2 signaling, anti-Notch2 antagonist antibodies and anti-Notch2 ligand antagonist antibodies. Examples of Notch2-specific antagonists include those described in U.S. Patent Application Publication No. US 2010/0111958.

In certain embodiments, the Notch2-specific antagonist is an anti-Notch2 antagonist antibody. In one such embodiment, the anti-Notch2 antagonist antibody is an antibody that binds to the extracellular domain of Notch2 and effects decreased Notch2 signaling. In one such embodiment, the anti-Notch2 antagonist antibody is an anti-Notch2 NRR antibody. Anti-Notch2 NRR antibodies include, but are not limited to, any of the anti-Notch2 NRR antibodies disclosed in U.S. Patent Application Publication No. US 2010/0080808 A1, which is expressly incorporated by reference herein in its entirety. Such antibodies include, but are not limited to anti-Notch2 NRR antibodies that bind to the LNR-A and HD-C domains of Notch2 NRR. Exemplary anti-Notch2 NRR antibodies are monoclonal antibodies designated Antibody D, Antibody D-1, Antibody D-2, or Antibody D-3 that were derived from a phage library, as disclosed in US 2010/0080808. Antibody D that binds to Notch2 NRR was isolated. That antibody was affinity matured to generate Antibody D-1, Antibody D-2, and Antibody D-3. The sequences of the heavy chain and light chain hypervariable regions (HVRs) of Antibody D, Antibody D-1, Antibody D-2, and Antibody D-3 are shown in FIGS. 12 and 13. The sequences of the heavy and light chain variable domains of Antibody D, Antibody D-1, Antibody D-2, and Antibody D-3 are shown in FIGS. 14 and 15. Further embodiments of anti-Notch2 NRR antibodies are provided as follows.

In one aspect, an antagonist antibody that specifically binds to Notch2 NRR is provided, wherein the antibody comprises at least one, two, three, four, five, or six HVRs selected from:

(a) an HVR-H1 comprising an amino acid sequence that conforms to the consensus sequence of SEQ ID NO:3;

(b) an HVR-H2 comprising the amino acid sequence of SEQ ID NO:4;

(c) an HVR-H3 comprising the amino acid sequence of SEQ ID NO:5;

(d) an HVR-L1 comprising an amino acid sequence that conforms to the consensus sequence of SEQ ID NO:10;

(e) an HVR-L2 comprising an amino acid sequence that conforms to the consensus sequence of SEQ ID NO:14; and (f) an HVR-L3 comprising an amino acid sequence that conforms to the consensus sequence of SEQ ID NO:19.

In a further aspect, the antibody comprises an HVR-H3 comprising the amino acid sequence of SEQ ID NO:5 and at least one, two, three, four, or five HVRs selected from (a), (b), (d), (e), and (f) above. In a further aspect, the antibody comprises (a), (b), (c), (d), (e), and (f) above. With respect to (a), (d), (e), and (f), any one or more of the following embodiments are contemplated: HVR-H1 comprises an amino acid sequence selected from SEQ ID NOs:1-2; HVR-L1 comprises an amino acid sequence selected from SEQ ID NOs:6-9; HVR-L2 comprises an amino acid sequence selected from SEQ ID NOs:11-13; and HVR-L3 comprises an amino acid sequence selected from SEQ ID NOs:15-18.

In another aspect, an antibody that specifically binds to Notch2 NRR is provided, wherein the antibody comprises an HVR-H1 comprising an amino acid sequence that conforms to the consensus sequence of SEQ ID NO:3, an HVR-H2 comprising the amino acid sequence of SEQ ID NO:4, and an HVR-H3 comprising the amino acid sequence of SEQ ID NO:5. In one embodiment, HVR-H1 comprises an amino acid sequence selected from SEQ ID NOs:1-2.

In another aspect, an antibody that specifically binds to Notch2 NRR is provided, wherein the antibody comprises an HVR-L1 comprising an amino acid sequence that conforms to the consensus sequence of SEQ ID NO:10, an HVR-L2 comprising an amino acid sequence that conforms to the consensus sequence of SEQ ID NO:14, and an HVR-L3 comprising an amino acid sequence that conforms to the consensus sequence of SEQ ID NO:19. The following embodiments are contemplated in any combination: HVR-L1 comprises an amino acid sequence selected from SEQ ID NOs:6-9; HVR-L2 comprises an amino acid sequence selected from SEQ ID NOs:11-13; and HVR-L3 comprises an amino acid sequence selected from SEQ ID NOs:15-18. In one embodiment, an antibody that binds to Notch2 NRR comprises an HVR-L1 comprising the amino acid sequence of SEQ ID NO:6; an HVR-L2 comprising the amino acid sequence of SEQ ID NO:11; and an HVR-L3 comprising the amino acid sequence of SEQ ID NO:15. In another embodiment, an antibody that binds to Notch2 NRR comprises an HVR-L1 comprising the amino acid sequence of SEQ ID NO:7; an HVR-L2 comprising the amino acid sequence of SEQ ID NO:11; and an HVR-L3 comprising the amino acid sequence of SEQ ID NO:16. In another embodiment, an antibody that binds to Notch2 NRR comprises an HVR-L1 comprising the amino acid sequence of SEQ ID NO:8; an HVR-L2 comprising the amino acid sequence of SEQ ID NO:12; and an HVR-L3 comprising the amino acid sequence of SEQ ID NO:17. In another embodiment, an antibody that binds to Notch2 NRR comprises an HVR-L1 comprising the amino acid sequence of SEQ ID NO:9; an HVR-L2 comprising the amino acid sequence of SEQ ID NO:13; and an HVR-L3 comprising the amino acid sequence of SEQ ID NO:18.

In one embodiment, an antibody that specifically binds to Notch2 NRR is provided, wherein the antibody comprises:

(a) an HVR-H1 comprising the amino acid sequence of SEQ ID NO:1;

(b) an HVR-H2 comprising the amino acid sequence of SEQ ID NO:4;

(c) an HVR-H3 comprising the amino acid sequence of SEQ ID NO:5;

(d) an HVR-L1 comprising the amino acid sequence of SEQ ID NO:6;

(e) an HVR-L2 comprising the amino acid sequence of SEQ ID NO:11; and (f) an HVR-L3 comprising the amino acid sequence of SEQ ID NO:15.

In another embodiment, an antibody that specifically binds to Notch2 NRR is provided, wherein the antibody comprises:

(a) an HVR-H1 comprising the amino acid sequence of SEQ ID NO:2;

(b) an HVR-H2 comprising the amino acid sequence of SEQ ID NO:4;

(c) an HVR-H3 comprising the amino acid sequence of SEQ ID NO:5;

(d) an HVR-L1 comprising the amino acid sequence of SEQ ID NO:7;

(e) an HVR-L2 comprising the amino acid sequence of SEQ ID NO:11; and (f) an HVR-L3 comprising the amino acid sequence of SEQ ID NO:16.

In another embodiment, an antibody that specifically binds to Notch2 NRR is provided, wherein the antibody comprises:

(a) an HVR-H1 comprising the amino acid sequence of SEQ ID NO:2;

(b) an HVR-H2 comprising the amino acid sequence of SEQ ID NO:4;

(c) an HVR-H3 comprising the amino acid sequence of SEQ ID NO:5;

(d) an HVR-L1 comprising the amino acid sequence of SEQ ID NO:8;

(e) an HVR-L2 comprising the amino acid sequence of SEQ ID NO:12; and (f) an HVR-L3 comprising the amino acid sequence of SEQ ID NO:17.

In another embodiment, an antibody that specifically binds to Notch2 NRR is provided, wherein the antibody comprises:

(a) an HVR-H1 comprising the amino acid sequence of SEQ ID NO:2;

(b) an HVR-H2 comprising the amino acid sequence of SEQ ID NO:4;

(c) an HVR-H3 comprising the amino acid sequence of SEQ ID NO:5;

(d) an HVR-L1 comprising the amino acid sequence of SEQ ID NO:9;

(e) an HVR-L2 comprising the amino acid sequence of SEQ ID NO:13; and (f) an HVR-L3 comprising the amino acid sequence of SEQ ID NO:18.

In certain embodiments, any of the above antibodies further comprises at least one framework selected from a VH subgroup III consensus framework and a VL subgroup I consensus framework.

In certain embodiments, an anti-Notch2 NRR antibody is affinity matured. For example, any one or more of the following substitutions in the indicated HVR positions (Kabat numbered) may be made in any combination:

in HVR-H1 (SEQ ID NO:1): S28T; T30S;

in HVR-L1 (SEQ ID NO:6): S28N; I29N or V; S30R or K; S31R; Y32F in HVR-L2 (SEQ ID NO:11): G50R; S53I or T; A55E in HVR-L3 (SEQ ID NO:15): S93I or R; L96W or H

The specific antibodies disclosed herein, i.e., Antibody D as well as affinity matured forms of Antibody D (D-1, D-2, and D-3), may undergo further affinity maturation. Accordingly, affinity matured forms of any of the antibodies described herein are provided.

In certain embodiments, an anti-Notch2 NRR antibody having any of the above HVR sequences can further comprise any suitable framework variable domain sequence, provided binding activity to Notch2 NRR is substantially retained. In certain embodiments, an anti-Notch2 NRR antibody comprises a human variable heavy (VH) consensus framework sequence, as in any of the VH consensus framework sequences shown in FIGS. 16A and 16B. In one embodiment, the VH consensus framework sequence comprises a human subgroup III heavy chain framework consensus sequence, e.g., as shown in FIGS. 16A and 16B. In another embodiment, the VH consensus framework sequence comprises an “Acceptor 2” framework sequence, e.g., as shown in FIGS. 16A and 16B. In a particular embodiment, the VH framework consensus sequence comprises FR1-FR4 of Acceptor 2B or Acceptor 2D, wherein the FR4 comprises SEQ ID NO:35 (FIGS. 16A and 16B), with the last residue of SEQ ID NO:35 (S11) optionally being substituted with alanine. In a further particular embodiment, the VH framework consensus sequence comprises the sequences of SEQ ID NOs:50; 51; 57 or 59; and 35, wherein S11 of SEQ ID NO:35 is optionally substituted with alanine In certain embodiments, an anti-Notch2 NRR antibody having any of the above HVR sequences can further comprise a human variable light (VL) consensus framework sequence as shown in FIG. 17. In one embodiment, the VL consensus framework sequence comprises a human VL kappa subgroup I consensus framework (κv1) sequence, e.g., as shown in FIG. 17. In another embodiment, the VL framework consensus sequence comprises FR1-FR4 of huMAb4D5-8 as shown in FIG. 18 or 19. In a particular embodiment, the VL framework consensus sequence comprises the sequences of SEQ ID NOs:60, 61, 62, and 63.

In another aspect, an anti-Notch2 NRR antibody comprises a heavy chain variable domain (VH) sequence having at least 90%, 91%, 92%, 93%, 94%, 95%, 96%, 97%, 98%, 99%, or 100% sequence identity to an amino acid sequence selected from SEQ ID NOs:20-21. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Notch2 NRR antibody comprising that sequence retains the ability to bind to Notch2 NRR. In certain embodiments, a total of 1 to 10 amino acids have been substituted, inserted and/or deleted in an amino acid sequence selected from SEQ ID NOs:20-21. In certain embodiments, substitutions, insertions, or deletions occur in regions outside the HVRs (i.e., in the FRs). In a particular embodiment, the VH comprises one, two or three HVRs selected from: (a) an HVR-H1 comprising an amino acid sequence that conforms to the consensus sequence of SEQ ID NO:3, (b) an HVR-H2 comprising the amino acid sequence of SEQ ID NO:4, and (c) an HVR-H3 comprising the amino acid sequence of SEQ ID NO:5. In one such embodiment, HVR-H1 comprises an amino acid sequence selected from SEQ ID NOs:1-2.

In another aspect, an antibody that specifically binds to Notch2 NRR is provided, wherein the antibody comprises a light chain variable domain (VL) having at least 90%, 91%, 92%, 93%, 94%, 95%, 96%, 97%, 98%, 99%, or 100% sequence identity to an amino acid sequence selected from SEQ ID NOs:22-25. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Notch2 NRR antibody comprising that sequence retains the ability to bind to Notch2 NRR. In certain embodiments, a total of 1 to 10 amino acids have been substituted, inserted and/or deleted in an amino acid sequence selected from SEQ ID NOs:22-25. In certain embodiments, the substitutions, insertions, or deletions occur in regions outside the HVRs (i.e., in the FRs). In a particular embodiment, the VL comprises one, two or three HVRs selected from (a) an HVR-L1 comprising an amino acid sequence that conforms to the consensus sequence of SEQ ID NO:10; (b) an HVR-L2 comprising an amino acid sequence that conforms to the consensus sequence of SEQ ID NO:14; and (c) an HVR-L3 comprising an amino acid sequence that conforms to the consensus sequence of SEQ ID NO:19. In one such embodiment, the VL comprises one, two or three HVRs selected from (a) an HVR-L1 comprising an amino acid sequence selected from SEQ ID NOs:6-9; (b) an HVR-L2 comprising an amino acid sequence selected from SEQ ID NOs:11-13; and (c) an HVR-L3 comprising an amino acid sequence selected from SEQ ID NOs:15-18. In one such embodiment, the VL comprises one, two or three HVRs selected from (a) an HVR-L1 comprising the amino acid sequence of SEQ ID NO:6; (b) an HVR-L2 comprising the amino acid sequence of SEQ ID NO:11; and (c) an HVR-L3 comprising the amino acid sequence of SEQ ID NO:15. In another such embodiment, the VL comprises one, two or three HVRs selected from (a) an HVR-L1 comprising the amino acid sequence of SEQ ID NO:7; (b) an HVR-L2 comprising the amino acid sequence of SEQ ID NO:11; and (c) an HVR-L3 comprising the amino acid sequence of SEQ ID NO:16. In another such embodiment, the VL comprises one, two or three HVRs selected from (a) an HVR-L1 comprising the amino acid sequence of SEQ ID NO:8; (b) an HVR-L2 comprising the amino acid sequence of SEQ ID NO:12; and (c) an HVR-L3 comprising the amino acid sequence of SEQ ID NO:17. In another such embodiment, the VL comprises one, two or three HVRs selected from (a) an HVR-L1 comprising the amino acid sequence of SEQ ID NO:9; (b) an HVR-L2 comprising the amino acid sequence of SEQ ID NO:13; and (c) an HVR-L3 comprising the amino acid sequence of SEQ ID NO:18.

In certain embodiments of the variant VH and VL sequences provided above, substitutions, insertions, or deletions may occur within the HVRs. In such embodiments, substitutions, insertions, or deletions may occur within one or more HVRs so long as such alterations do not substantially reduce the ability of the antibody to bind antigen. For example, conservative alterations that do not substantially reduce binding affinity may be made in HVRs. In certain instances, alterations in HVRs may actually improve antibody affinity. Such alterations may be made in HVR "hotspots" (i.e., residues encoded by codons that undergo mutation at high frequency during the somatic maturation process) in order to increase antibody affinity. (See, e.g., Chowdhury, *Methods Mol. Biol.* 207:179-196, 2008.) In certain embodiments of the variant VH and VL sequences provided above, each HVR either is conserved (unaltered), or contains no more than a single amino acid substitution, insertion or deletion.

In another aspect, an antibody that specifically binds Notch2 NRR is provided, wherein the antibody comprises a VH as in any of the embodiments provided above, and a VL as in any of the embodiments provided above. In one embodiment, the antibody comprises a VH having at least 90%, 91%, 92%, 93%, 94%, 95%, 96%, 97%, 98%, 99%, or 100% sequence identity to the amino acid sequence of SEQ ID NO:20, and a VL having at least 90%, 91%, 92%, 93%, 94%, 95%, 96%, 97%, 98%, 99%, or 100% sequence identity to the amino acid sequence of SEQ ID NO:22. In one such embodiment, the VH comprises one, two or three HVRs selected from: (a) an HVR-H1 comprising the amino acid sequence of SEQ ID NO:1, (b) an HVR-H2 comprising the amino acid sequence of SEQ ID NO:4, and (c) an HVR-H3 comprising the amino acid sequence of SEQ ID NO:5, and the VL comprises one, two or three HVRs selected from (a) an HVR-L1 comprising the amino acid sequence of SEQ ID NO:6; (b) an HVR-L2 comprising the amino acid sequence of SEQ ID NO:11; and (c) an HVR-L3 comprising the amino acid sequence of SEQ ID NO:15. In a particular embodiment, the antibody comprises a VH comprising the amino acid sequence of SEQ ID NO:20, and a VL comprising the amino acid sequence of SEQ ID NO:22.

In another embodiment, an anti-Notch2 NRR antibody that specifically binds Notch2 NRR comprises a VH having at least 90%, 91%, 92%, 93%, 94%, 95%, 96%, 97%, 98%, 99%, or 100% sequence identity to the amino acid sequence of SEQ ID NO:21, and a VL having at least 90%, 91%, 92%, 93%, 94%, 95%, 96%, 97%, 98%, 99%, or 100% sequence identity to an amino acid sequence selected from SEQ ID NOs:23-25. In one such embodiment, the VH comprises one, two or three HVRs selected from: (a) an HVR-H1 comprising the amino acid sequence of SEQ ID NO:2, (b) an HVR-H2 comprising the amino acid sequence of SEQ ID NO:4, and (c) an HVR-H3 comprising the amino acid sequence of SEQ ID NO:5, and the VL comprises one, two or three HVRs selected from (a) an HVR-L1 comprising an amino acid sequence selected from SEQ ID NOs:7-9; (b) an HVR-L2 comprising an amino acid sequence selected from SEQ ID NOs:11-13; and (c) an HVR-L3 comprising an amino acid sequence selected from SEQ ID NOs:16-18. In particular embodiments, the antibody comprises a VH comprising the amino acid sequence of SEQ ID NO:21 and a VL comprising an amino acid sequence selected from SEQ ID NOs:23-25.

In certain embodiments, an affinity-matured form of any of the above antibodies is provided. In further embodiments, a recombinant protein that specifically binds Notch2 NRR is provided, wherein the recombinant protein comprises an antigen binding site(s) of any of the above antibodies. In one such embodiment, a recombinant protein comprises any one or more of the HVRs provided above.

In certain embodiments, a polynucleotide encoding any of the above antibodies is provided. In one embodiment, a vector comprising the polynucleotide is provided. In one embodiment, a host cell comprising the vector is provided. In one embodiment, the host cell is eukaryotic. In one embodiment, the host cell is a CHO cell. In one embodiment, a method of making an anti-Notch2 NRR antibody is provided, wherein the method comprises culturing the host cell under conditions suitable for expression of the polynucleotide encoding the antibody, and isolating the antibody.

In another embodiment, an isolated antibody is provided that binds to the same epitope as an antibody provided herein. In one embodiment, an isolated anti-Notch2 NRR antibody is provided that binds to the same epitope as an antibody selected from Antibody D, Antibody D-1, Antibody D-2, and Antibody D-3. In another embodiment, the invention provides an anti-Notch2 NRR antibody that competes for binding with an antibody selected from Antibody D, Antibody D-1, Antibody D-2, and Antibody D-3. In another embodiment, an isolated antibody is provided that binds to at least one domain selected from the LNR-A domain and the HD-C domain of Notch2. In one such embodiment, the antibody binds to both the LNR-A domain and the HD-C domain. In another such embodiment, the antibody further binds to the LNR-B and/or HD-N domains.

Any of the Notch2-specific antagonists provided herein may be used in therapeutic methods. In one aspect, a Notch2-specific antagonist for use as a medicament is provided. In further aspects, a Notch2-specific antagonist for use in treating a liver condition characterized by liver damage is provided. In certain embodiments, a Notch2-specific antagonist for use in a method of treatment is provided. In certain embodiments, the invention provides a Notch2-specific antagonist for use in a method of treating an individual having a liver condition characterized by liver damage comprising administering to the individual an effective amount of the Notch2-specific antagonist. In one such embodiment, the method further comprises administering to the individual an effective amount of at least one additional therapeutic agent, e.g., as described below. An "individual" according to any of the above embodiments is preferably a human.

In a further aspect, the invention provides for the use of a Notch2-specific antagonist in the manufacture or preparation of a medicament. In one embodiment, the medicament is for treatment of a liver condition characterized by liver damage. In a further embodiment, the medicament is for use in a method of treating a liver condition characterized by liver damage comprising administering to an individual having a liver condition characterized by liver damage an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides pharmaceutical formulations comprising any of the Notch2-specific antagonists provided herein, e.g., for use in any of the above therapeutic methods. In one embodiment, a pharmaceutical formulation comprises any of the Notch2-specific antagonists provided herein and a pharmaceutically acceptable carrier. In another embodiment, a pharmaceutical formulation comprises any of the Notch2-specific antagonists provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antagonist of the invention can occur prior to, simultaneously, and/or following, administration of the additional therapeutic agent and/or adjuvant. Antagonists of the invention can also be used in combination with radiation therapy.

The antagonist can be administered to a human patient by any known method, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The Notch2-specific antagonist might be administered as a protein or as a nucleic acid encoding a protein (see, for example, WO96/07321). Other therapeutic regimens may be combined with the administration of the Notch2-specific antagonist. The combined administration includes co-administration, using separate formulations or a single pharmaceutical formulation, and consecutive administration in either order, wherein preferably there is a time period while both (or all) active agents simultaneously exert their biological activities. In some embodiments, such combined therapy results in a synergistic therapeutic effect.

The dosage and mode of administration will be chosen by the physician according to known criteria. The appropriate dosage of antibody, oligopeptide or organic molecule will depend on the type of disease to be treated, the severity and course of the disease, whether the antibody, oligopeptide or organic molecule is administered for preventive or therapeutic purposes, previous therapy, the patient's clinical history and response to the Notch2-specific antagonist, and the discretion of the attending physician. The Notch2-specific antagonist can be administered to the patient at one time or over a series of treatments.

Success of treatment of liver disease can be monitored by assessing parameters of liver function and recovery. Such parameters include, but are not limited to, improved liver function tests, (e.g., assessing serum albumin, bilirubin, bile acids, total protein, clotting times), liver enzymes (e.g., alanine transaminase, aspartate transaminase, alkaline phosphatase, gamma glutamyl transpeptidase), histologic appearance (e.g., needle biopsy showing improved hepatic architecture), and imaging modalities (e.g., ultrasound, magnetic resonance imaging for fibrosis and liver size).

In a further aspect, an anti-Notch2 antibody used in any of the above embodiments may incorporate any of the features, singly or in combination, as described in Sections 1-7 below.

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g., $10^{-8}$ M or less, e.g. from $10^{-8}$M to $10^{-13}$M, e.g., from $10^{-9}$M to $10^{-13}$ M). For example, the exemplary phage Antibody D-3 binds to Notch2 with a Kd of 5 nM.

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6\ M^{-1}\ 5^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage).

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Notch2 and the other is for any other antigen. In certain embodiments, bispecific antibodies may bind to two different epitopes of Notch2. Bispecific antibodies may also be used to localize cytotoxic agents to cells which express Notch2. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Notch2 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, *FUT*8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). Clq binding assays may also be carried out to confirm that the antibody is unable to bind Clq and hence lacks CDC activity. See, e.g., Clq and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) Clq binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-Notch2 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-Notch2 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Notch2 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-Notch2 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with Antibody D, Antibody D-1, Antibody D-2, or Antibody D-3 for binding to Notch2. In certain embodiments, such a competing antibody binds to the same epitope (e.g., a linear or a conformational epitope) that is bound by Antibody D, Antibody D-1, Antibody D-2, or Antibody D-3. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized Notch2 is incubated in a solution comprising a first labeled antibody that binds to Notch2 (e.g., Antibody D, Antibody D-1, Antibody D-2, or Antibody D-3) and a second unlabeled antibody that is being tested for its ability to compete with the first antibody for binding to Notch2. The second antibody may be present in a hybridoma supernatant. As a control, immobilized Notch2 is incubated in a solution comprising the first labeled antibody but not the second unlabeled antibody. After incubation under conditions permissive for binding of the first antibody to Notch2, excess unbound antibody is removed, and the amount of label associated with immobilized Notch2 is measured. If the amount of label associated with immobilized Notch2 is substantially reduced in the test sample relative to the control sample, then that indicates that the second antibody is competing with the first antibody for binding to Notch2. See Harlow and Lane (1988) Antibodies: *A Laboratory Manual* ch.14 (Cold Spring Harbor Laboratory, Cold Spring Harbor, N.Y.).

2. Activity Assays

In one aspect, assays are provided for identifying anti-Notch2 antibodies thereof having biological activity. Biological activity may include, e.g., inhibition or reduction of Notch2 activity, e.g., Notch2 signaling. Antibodies having such biological activity in vivo and/or in vitro are also provided.

In certain embodiments, an anti-Notch2 NRR antibody of the invention is tested for its ability to inhibit generation of marginal zone B cells. An exemplary assay is provided in the Examples. In certain other embodiments, an antibody of the invention is tested for its ability to inhibit expression of a reporter gene that is responsive to Notch2 signaling.

D. Immunoconjugates

The invention also provides immunoconjugates comprising an anti-Notch2 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

III. Examples

Example 1: Isolation and Transcriptional Profiling of Liver Progenitor Cells To identify the signals that regulate hepatocyte differentiation from liver progenitor cells, transcriptional profiling was performed on adult liver progenitors (oval cells) from mice fed a choline deficient, ethionine supplemented (CDE) diet (FIG. 1A; FIG. 5A). This CDE model is known in the art as a model of chronic liver disease. CDE is also a steatohepatitis model (NASH). Chronic CDE can also lead to hepatocellular carcinoma (HCC), thereby also serving as a model for HCC. To induce an oval cell response, 8-12 week-old female C57BL/6N mice (Charles River) were fed a choline deficient diet (20% Lard; Teklad TD.04523) supplemented with 0.15% (w/v) Ethionine in the drinking water (Akhurst et al., Hepatology 34(3):519 (2001)). Liver non-parenchymal cells were isolated according to the protocol of del Castillo (del Castillo et al., Am. J. Pathol., 172(5):1238 (2008)) with the addition of 0.04% Hyaluronidase (Sigma) to the in vitro dissociation step.

Figure 4A:
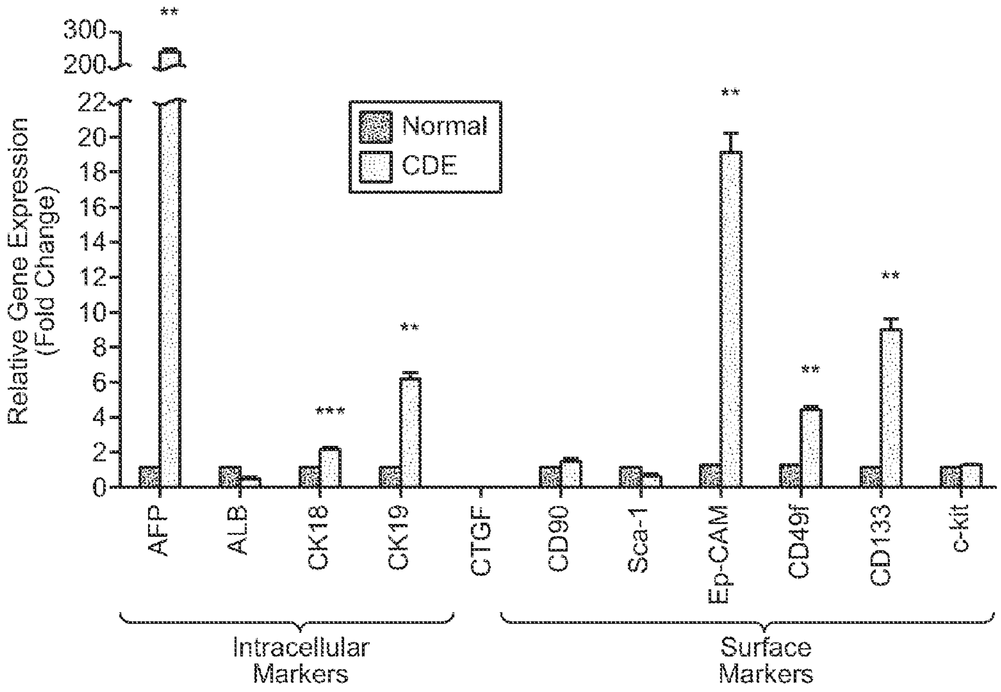
FIGS. 4A-E illustrate a liver progenitor cell isolation strategy.
Figure 4B:
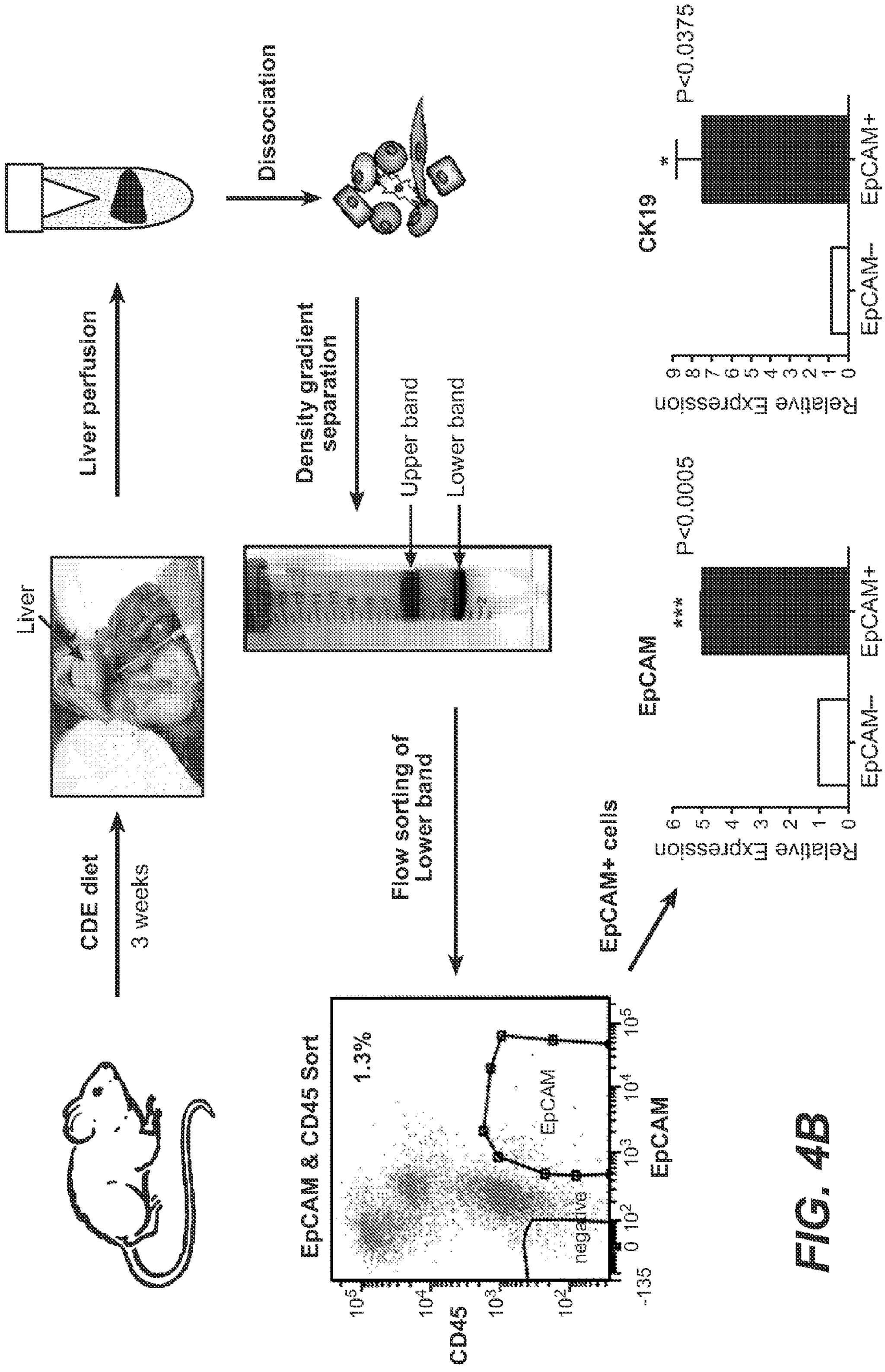
Figure 4C:
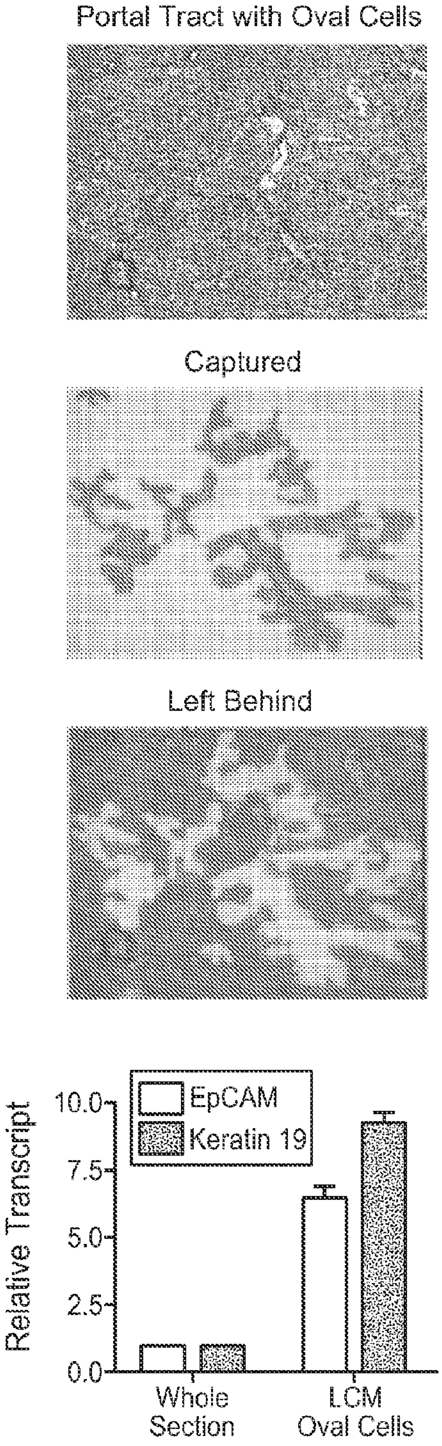
Figure 4D:
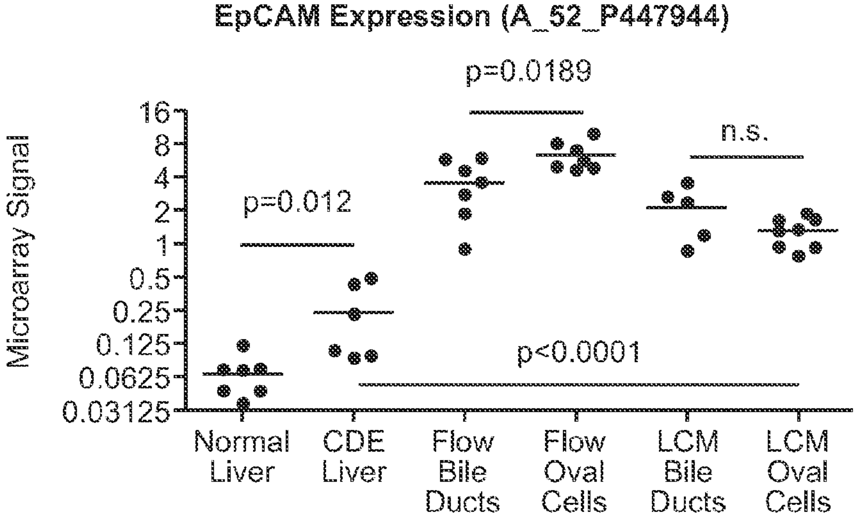
Figure 4E:
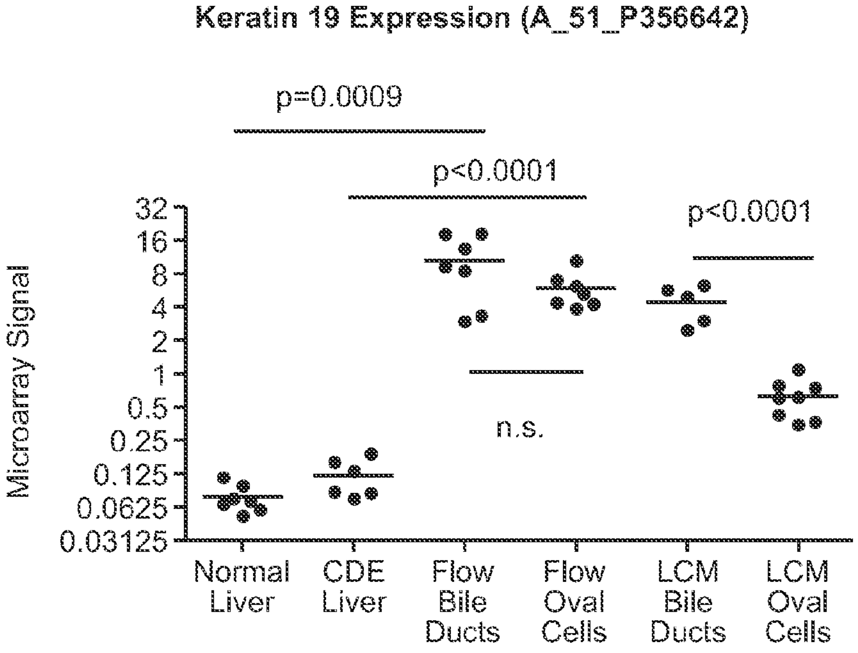

Epithelial Cell Adhesion Molecule (EpCAM)-expressing progenitor cells and normal bile duct cells from livers of CDE-fed and control mice were isolated by fluorescence activated cell sorting (FACS; FIG. 4A-B). C57BL/6 mouse livers were perfused with a Collagenase/Pronase solution and the liver was dissociated and further incubated in the presence of DNase and Hyaluronidase (FIG. 4B). The resulting cell suspension was passed over a 30%/70% Percoll density gradient by centrifugation at 2500 RPM for 30 minutes. Cells from the 30%/70% Percoll interface, consisting mostly of non-parenchymal cells, were stained with fluorescently labeled antibodies to EpCAM (BioLegend) and CD45 (BD Pharmingen). Flow cytometry was used to isolate $EpCAM^+/VCD45^-$ cells from mice fed CDE or standard rodent diet. The majority of $EpCAM^+/VCD45^-$ cells from CDE-fed mice were oval cells, while the majority of $EpCAM^+/VCD45^-$ cells from standard diet-fed mice were bile duct cells. QRT-PCR analysis on RNA from FACS sorted cells confirmed that $EpCAM^+/VCD45^-$-sorted cells were greatly enriched for EpCAM as well as CK19 (FIG. 4B), indicating a successful positive selection of $EpCAM^+$ progenitor and bile duct cells.

In addition to isolating progenitor cells by FACS sorting, progenitor and normal bile duct cells were isolated by laser capture microdissection (LCM) from hematoxylin and eosin (H&E) stained liver sections. Livers from C57BL/6N 8-12 week-old female mice fed normal chow or CDE diet were removed and immediately flash frozen in liquid Nitrogen. Flash frozen liver pieces were placed in prechilled plastic molds, embedded in TISSUE-TEK OCT Compound (Sakura, The Netherlands) and immediately placed on a dry ice/2-methylbutane bath until frozen. The embedded frozen liver pieces were cut into 7-8 μm sections at −14° C., adhered to metal frame membrane slides (MMI, Eching, Germany), fixed, stained with hematoxylin and eosin, and dried. Laser microdissection was used to isolate 1-2 $mm^2$ of oval cell or normal bile duct tissue per sample.

RNA from flow-sorted and laser microdissected tissue was isolated using the RNEASY Micro Kit (Qiagen). For microarray analysis RNA from flow-sorted and laser microdissected tissue, as well as whole liver controls, spiked with Agilent RNA Spike-In RNA (Agilent), was submitted to two rounds of amplification with Message AmpII (Ambion) and hybridized to Whole Mouse Genome Oligo 44 k microarrays. Log expression ratios were exported and analyzed using Partek Genomic Suite (Partek). Quantitative real-time PCR (QRTPCR) was performed using the TAQMAN One-Step RT-PCR Kit for one step reactions using the 7900 HT RT-PCR system (Applied Biosystems) with TAQMAN probes (Applied Biosystems) or High Capacity cDNA RT kit with TAQMAN Fast Advanced Master Mix using the Viia7 RT-PCR system (Applied Biosystems) with custom designed low density arrays.

Figure 1B:
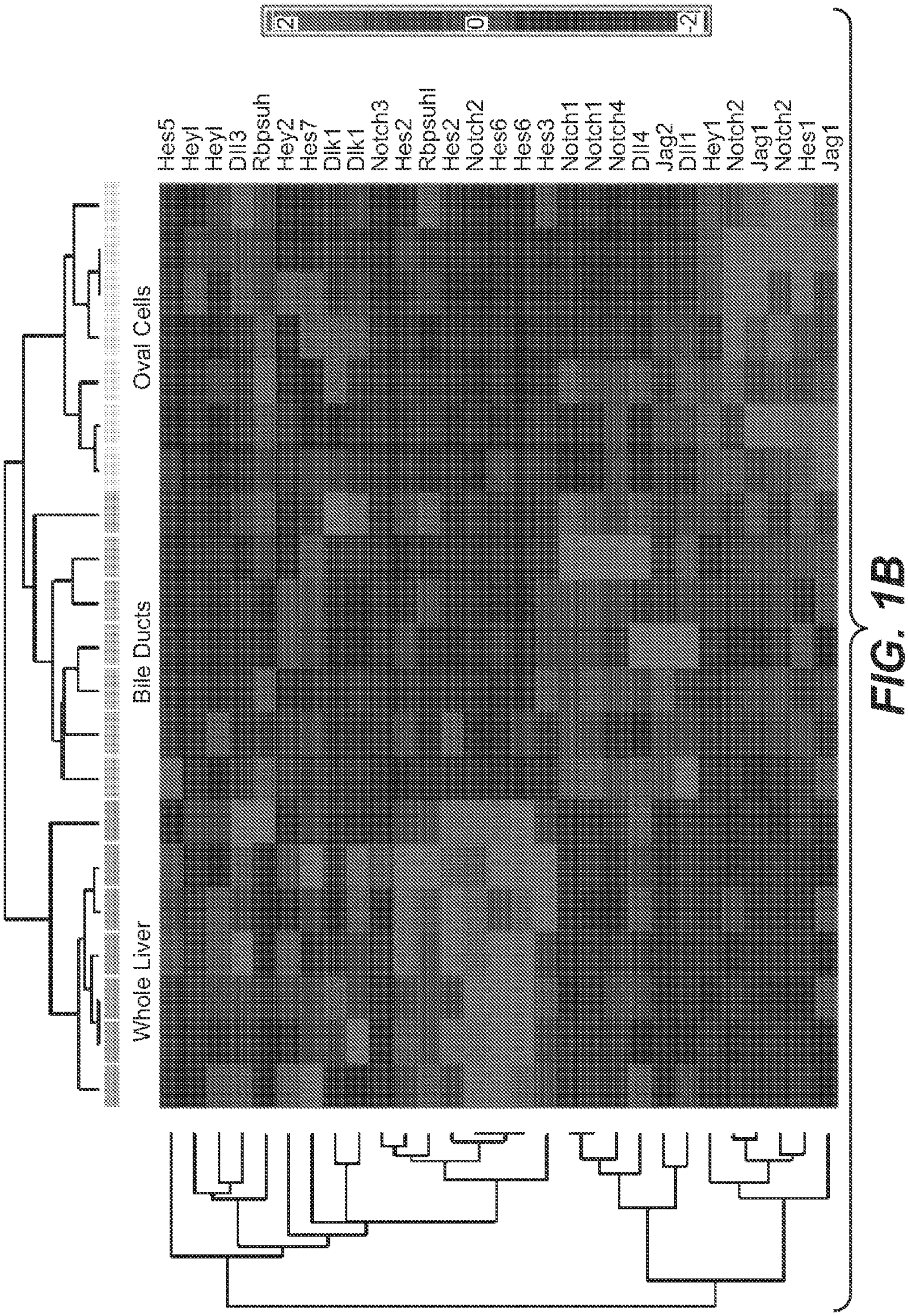
Figure 1C:
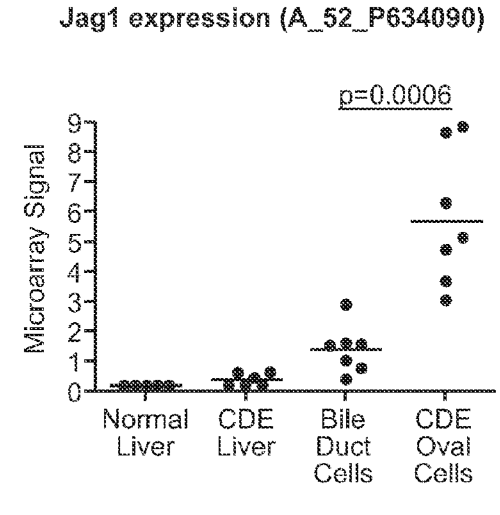
Figure 1D:
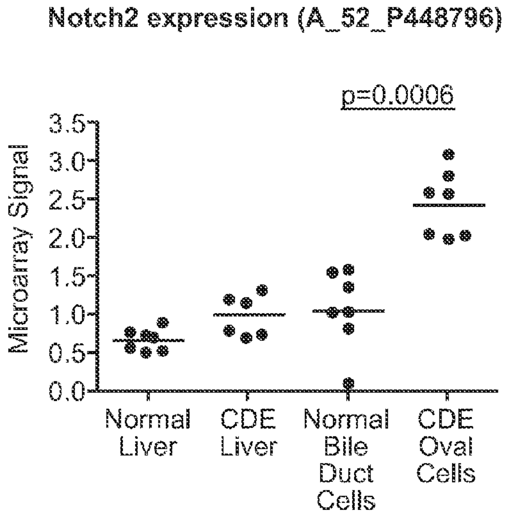
Figure 1E:
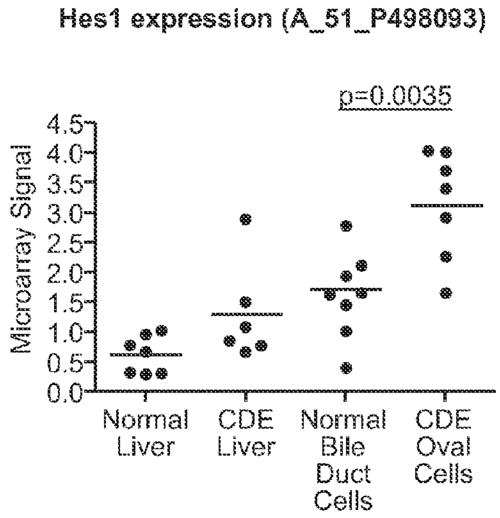
Figure 1F:
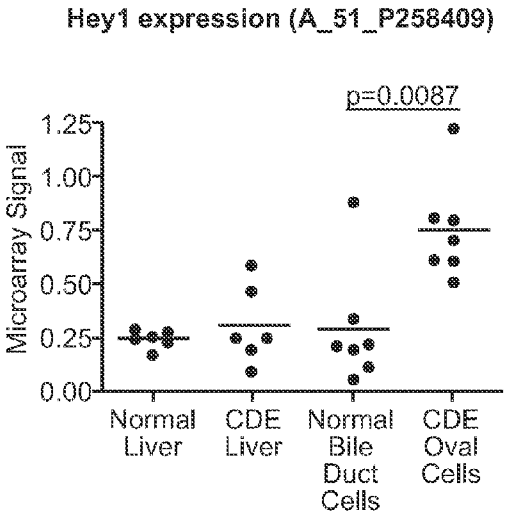
Figure 1G:
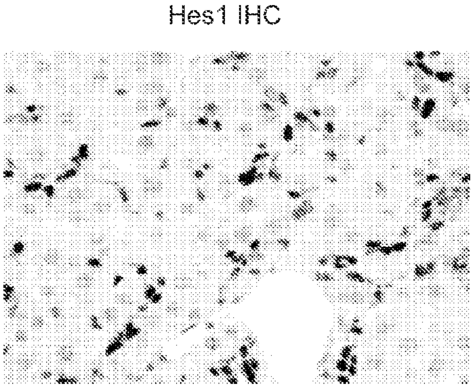

Enrichment of bile duct and progenitor cell-associated transcripts, such as EpCAM and Keratin19, confirmed effective isolation of bile duct and progenitor cells (FIG. 1E). Using supervised analysis (FIG. 5B), genes expressed more highly in liver progenitor cells than in closely related normal bile duct cells were identified (Table 2). This supervised analysis correlated highly with progenitor cell associated transcripts identified by unbiased principle components analysis (FIG. 5C-H). The expression pattern of these genes was validated on independent samples by QRT-PCR (FIG. 6) and immunofluorescence, which confirmed that members of the Notch signaling pathway, including Jag1 and Notch2, as well as Hes1 and Hey1, among other target genes, were upregulated in liver progenitor cells compared to bile duct cells (FIG. 1C-G). A selection of microarray probes for Notch pathway-associated transcripts distinguished flow-sorted oval cells from flow-sorted biliary cells and whole liver by supervised clustering (FIG. 1B). Supervised hierarchical clustering of 29 Notch pathway-associated genes, including receptors, ligands, transcription factors, and select target genes, differentiated whole liver, bile ducts, and oval cells into separate clusters (Rand index=1, 3 clusters; Rand index=0.7607, 3 clusters, for randomly generated list of 29 genes) and revealed differences between normal bile duct cells and progenitors. The data showed significant upregulation of Jag1 (p=0.0006; FIG. 1C), Notch2 (p=0.0006; FIG. 1D), Hes1 (p=0.0035; FIG. 1E), and Hey1 (p=0.0087; FIG. 1F) in liver progenitor cells. Immunofluorescence staining confirmed that Jag1 was more highly expressed in $EpCAM^+$ oval cells radiating out from the portal vein in a CDE liver than in adjacent normal bile duct cells. Immunhistochemistry for Hes1 confirmed that Hes1 positive cells were largely confined to the oval cell and bile duct compartments, with some staining in other non-parenchymal cells of the liver (FIG. 1G).

TABLE 2

Oval Cell Associated Genes

| UNQ_Short_Name | ProbeID | t-statistic | pvalue | log2 (Fold Change) |
|---|---|---|---|---|
| ADAMTS9 | A_52_P49321 | 5.272 | 0 | 2.132 |
| ANXA9 | A_51_P451482 | 6.839 | 0 | 2.578 |
| APP | A_52_P381311 | 5.045 | 0 | 2.531 |
| BMP8B | A_51_P411926 | 6.273 | 0 | 3.562 |
| CHRNB1 | A_51_P475342 | 5.32 | 0 | 1.912 |
| CTGF | A_51_P157042 | 7.146 | 0 | 3.336 |
| DTNA | A_52_P108607 | 5.585 | 0 | 3.558 |
| Embigin | A_51_P382849 | 6.196 | 0 | 3.246 |
| Epdr2 | A_52_P577388 | 5.703 | 0 | 2.431 |
| EPHA7 | A_52_P504787 | 5.855 | 0 | 2.255 |
| FADS3 | A_52_P451796 | 5.809 | 0 | 2.163 |
| Foxc1 | A_51_P107686 | 5.098 | 0 | 2.77 |
| GSPT1 | A_52_P354785 | 5.672 | 0 | 2.726 |
| Hig2I | A_52_P321150 | 5.522 | 0 | 1.696 |
| ID2 | A_52_P240542 | 5.054 | 0 | 1.504 |
| Ifrd1 | A_51_P367060 | 5.888 | 0 | 1.609 |
| JAG1 | A_52_P634090 | 5.368 | 0 | 2.377 |
| LTB | A_51_P302358 | 6.15 | 0 | 2.428 |
| MAL | A_52_P562661 | 5.619 | 0 | 3.02 |
| Mex3a | A_52_P706060 | 5.228 | 0 | 3.582 |
| MFI2 | A_51_P324351 | 7.735 | 0 | 3.397 |
| MYC | A_51_P102096 | 5.498 | 0 | 1.522 |
| NFAM1 | A_52_P686701 | 5.472 | 0 | 2.09 |
| NFKB1 | A_52_P32733 | 5.348 | 0 | 2.398 |
| Nrarp | A_51_P504354 | 5.261 | 0 | 2.585 |
| peg 3 | A_51_P206037 | 6.329 | 0 | 2.84 |
| RASL11A | A_51_P340699 | 5.425 | 0 | 2.303 |
| SLIT2 | A_51_P496569 | 5.964 | 0 | 3.261 |
| SPATA7 | A_52_P134680 | 5.187 | 0 | 1.926 |
| SPRR1A | A_51_P139678 | 7.825 | 0 | 2.8 |
| TNFAIP8 | A_51_P435968 | 6.322 | 0 | 2.403 |
| TNFRSF12A | A_51_P131408 | 6.641 | 0 | 2.397 |
| tp53 | A_52_P957260 | 5.399 | 0 | 2.388 |
| TRIM47 | A_51_P437176 | 5.633 | 0 | 1.592 |
| Trio | A_51_P319662 | 6.257 | 0 | 2.81 |
| TTYH1 | A_52_P475052 | 5.668 | 0 | 2.442 |
| USP47 | A_52_P610967 | 5.021 | 0 | 2.018 |
| VCAM1 | A_51_P210956 | 5.696 | 0 | 1.847 |

Example 2: Identification of Expression Patterns of Oval Cell-Associated Genes

The microarray data from RNA isolated from oval and bile duct cells isolated FACS (Flow) or microdisection (LCM) and control and CDE livers were examined for the expression of putative markers of oval cells and markers of other select cell types. Albumin transcript was detected at relatively high levels in all groups (FIG. 6A-1), whereas AFP, a marker of immature hepatocytes that is upregulated during chronic liver damage, was greatly enriched in LCM oval cells, but virtually absent from the other cell types examined (FIG. 6A-1). To determine why AFP was present only in LCM oval cells, immunofluorescence was performed on 7 μm frozen CDE liver sections that had been briefly air-dried and fixed in 4% paraformaldehyde in PBS. After blocking with normal horse serum in PBS, sections were incubated with fluorescently labeled antibodies to EpCAM (BioLegend), Sca1 (BD Pharmingen), CD90 (BioLegend), or with unlabeled primary antibodies to AFP (R&D Systems) and CK19 (Santa Cruz Biotech) followed by incubation with fluorescently labeled secondary antibodies (Invitrogen). AFP was expressed in only a subset of hepatocytes, often in close proximity to $EpCAM^+$ oval cells. However, AFP expression could not be observed in oval cells themselves.

Figures 3, 6A:
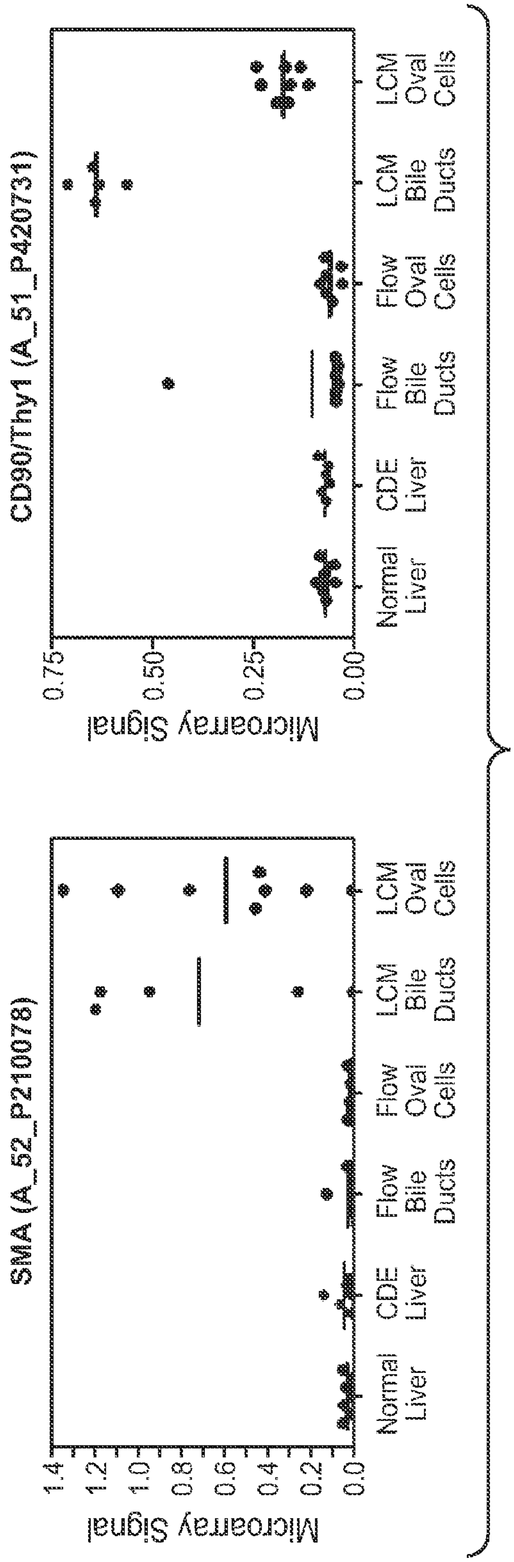
Figure 6B:
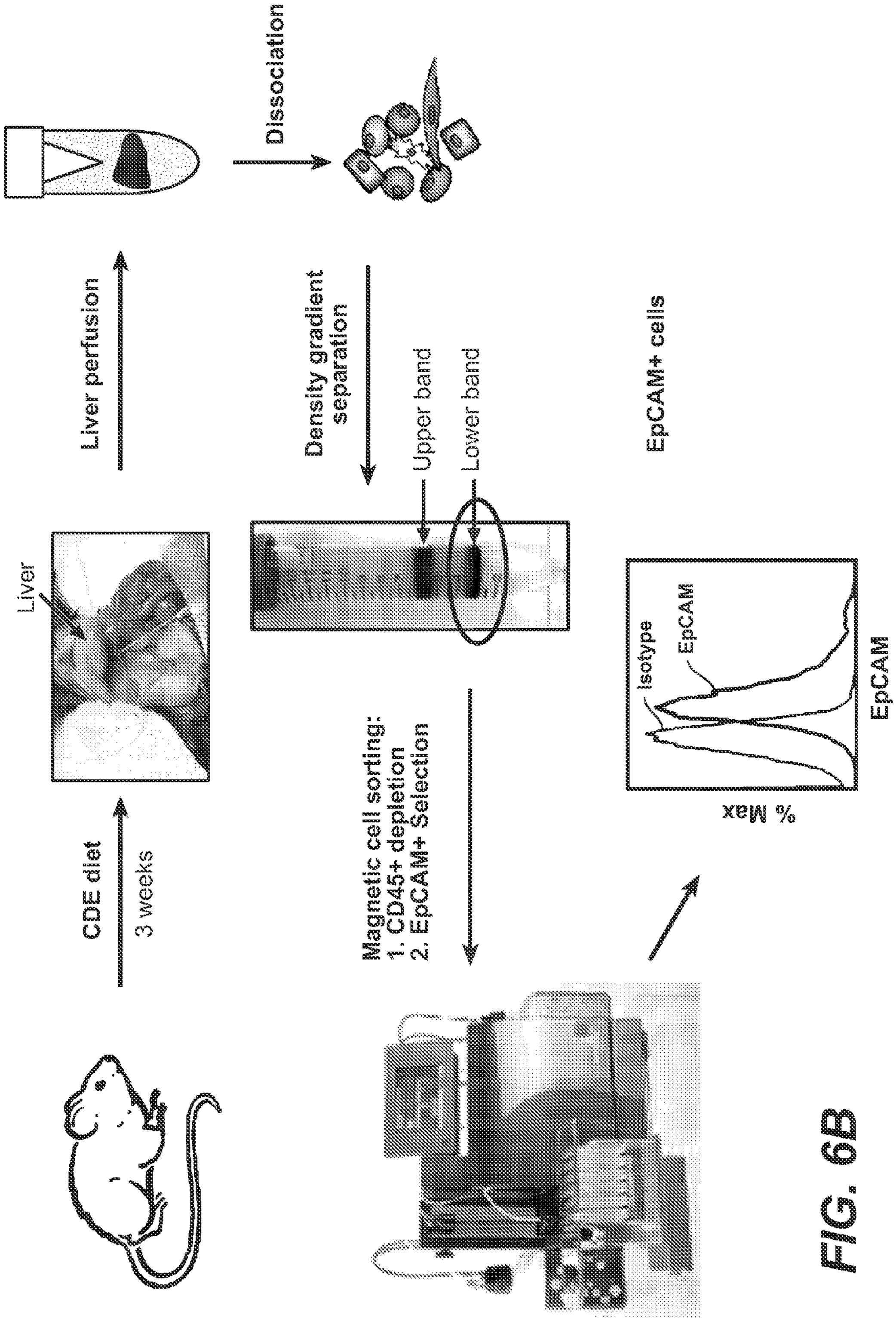
Figure 6C:
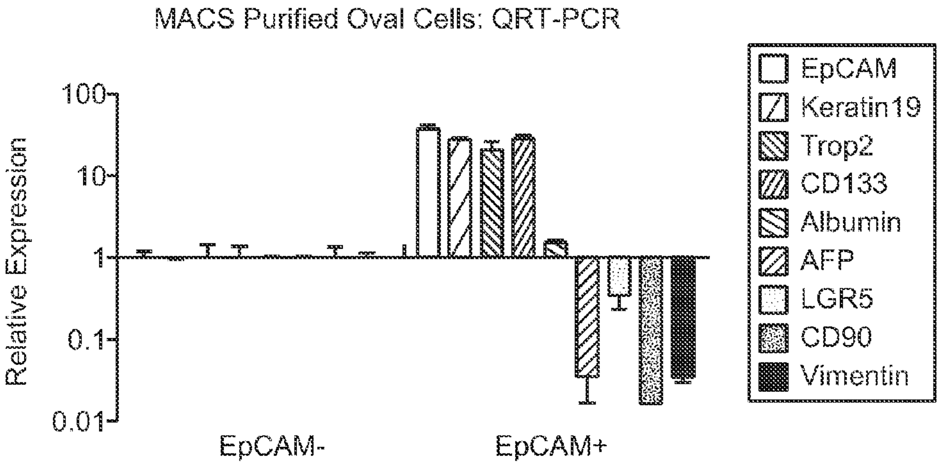
Figure 6E:
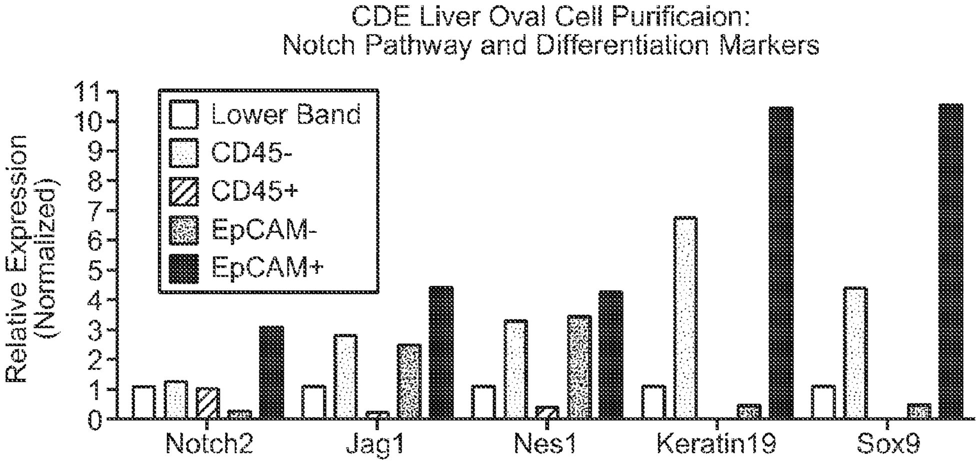
Figure 6D:
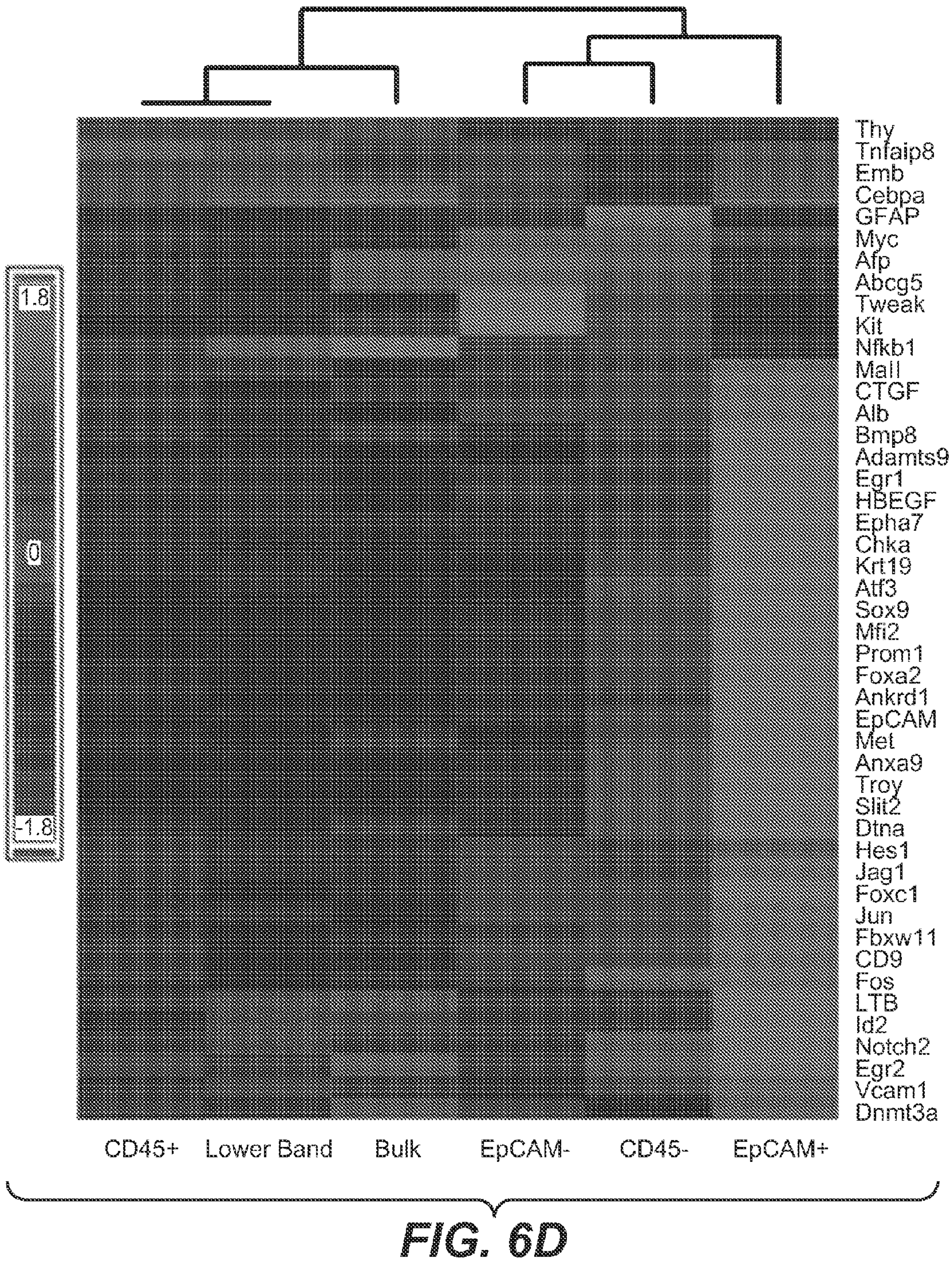

LCM isolates expressed high levels of the myofibroblast marker SMA and the mesenchymal cell marker CD90/Thy1 (FIG. 6A-3), possibly as a result of inclusion of periportal myofibroblasts, which are positive for both CD90/Thy1 and SMA. Thus, it appears that the LCM samples contain a heterogeneous mixture of cell types that at least include myofibroblasts, and in the case of LCM samples from CDE livers, AFP positive hepatocytes adjacent to cords of microdissected oval cells. Though Sca1 also marks mesenchymal cells, it also appears to be expressed in bile duct cells and oval cells themselves, as the transcript is found at high levels in both the FACS-sorted and LCM samples (FIG. 6A-2). The oval cell markers CD13, Sox9, FoxL, and FoxJ1 were also expressed in both FACS-sorted and LCM samples. Except for Sox9, which was more highly expressed in FACS oval cells, each of these markers was expressed at comparable levels in CDE oval cells and in normal bile ducts. Expression patterns of oval cell-associated genes and genes marking other hepatic cell types were confirmed in independent samples by QRT-PCR. For these experiments, CDE oval cells were enriched by Magnetically Activated Cell Sorting (MACS), first by depleting $CD45^+$ cells from the lower band of a 30%/70% Percoll gradient followed by positive selection for $EpCAM^+$ cells (FIG. 6B). Purity of the resulting cell suspensions was >95%. c, Relative to CD45−/EpCAM− cells, CD45−/EpCAM+ cells expressed high levels of EpCAM, CK19, Trop2, and CD133 and low levels of AFP, LGR5, CD90, and Vimentin (FIG. 6C). Albumin was expressed at comparable levels in $CD45^-/EpCAM^-$ and $CD45^-/EpCAM^+$ fractions.

Example 3: Notch Signaling in Liver Progenitors In Vitro

To elucidate the role of Notch signaling in liver regeneration, an in vitro culture system was developed. Cell cultures were established by culturing primary oval cells on Sw-3T3 fibroblasts (ATCC), arrested with Mitomycin C (Sigma), in High Glucose Dulbecco's Modified Eagle Medium (DMEM; Invitrogen) supplemented with 15% Fetal Calf Serum (Sigma), non-essential amino acids (Invitrogen), Glutamax (Invitrogen), and ITS (Invitrogen).

The anti-activated Notch2 antibody (clone 40-2-7) was generated against the peptide VIMAKRKRKHGSLW, corresponding to amino acids 1697-1710 of the human Notch2 protein sequence (SEQ ID NO:73), coupled to KLH (Yen-Zym Custom Antibodies, LLC). Splenocytes from a rabbit producing an antibody with the appropriate specificity were used to generate hybridomas (Epitomics, Inc.). Clone 40-2-7 was identified by screening the resulting rabbit monoclonal antibodies by immunoblotting and immunohistochemistry. This antibody recognizes both human (FIG. 7B, left panel) and mouse (FIG. 7B, right panel) active Notch2 at endogenous levels.

Figure 2A:
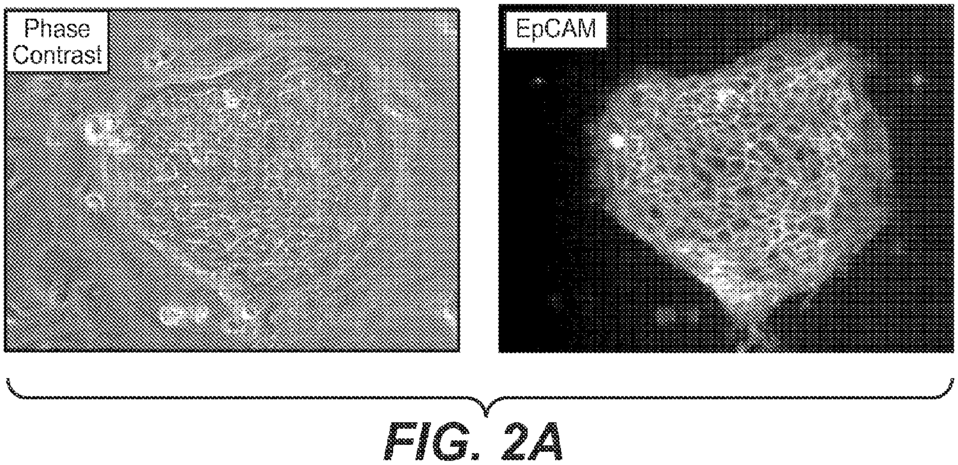
FIGS. 2A-O show that Notch signaling inhibition promotes hepatocyte differentiation of hepatic progenitors in vitro.
Figure 2B:
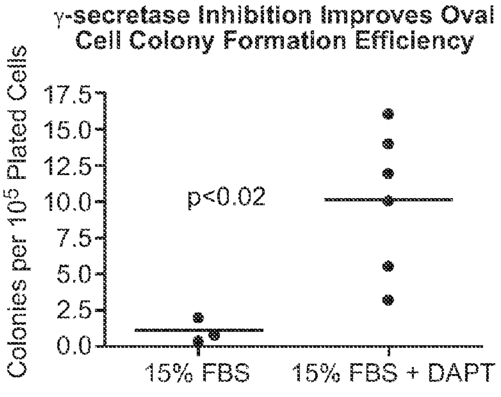
Figure 2D:
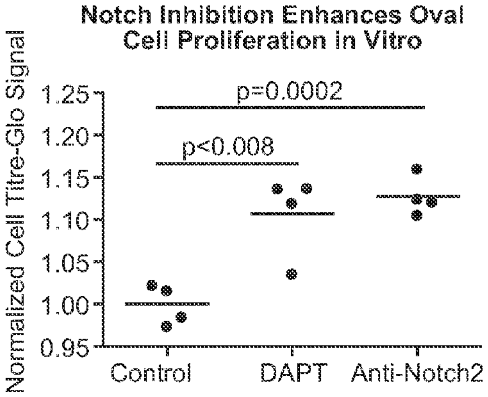
Figure 2C:
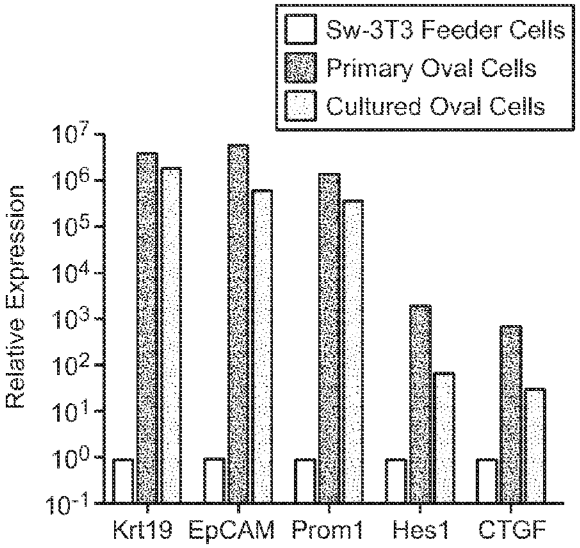

Progenitors cultured in the culture system maintained growth (FIG. 2A) and formed colonies consisting of small, tightly packed cells with a high nuclear-cytoplasmic ratio and a distinct raised edge (FIG. 2A, left panel). The cells within these colonies were uniformly EpCAM positive (FIG. 2A, right panel). Progenitor cultures also maintained the characteristic progenitor expression signature in vitro (FIG. 2C). Activated Notch2 was detected by Western blot analysis using a rabbit monoclonal antibody raised against the S3 cleaved form of the human Notch2 protein (FIG. 7B). Activated Notch2 signal was increased upon ligand stimulation (Jag) or EDTA stimulation (EDTA), and the activated form was greatly enriched in the nuclear fraction (FIG. 7B; lanes "N").

Treatment of the primary cultures with the γ-secretase and Notch pathway inhibitor N—[N-(3,5-difluorophenacetyl)-1-alanyl]-S-phenylglycine t-butyl ester (DAPT) unexpectedly enhanced colony formation approximately ten-fold, from approximately 1 colony formed per 100,000 plated CD45 negative, non-parenchymal cells to approximately 1 colony per 10,000 cells plated (FIG. 2B) suggesting that inhibition of Notch pathway activity promoted either liver progenitor cell maintenance or proliferation. Treatment with DAPT resulted in a small increase in progenitor cell proliferation (FIG. 2D).

Figure 7A:
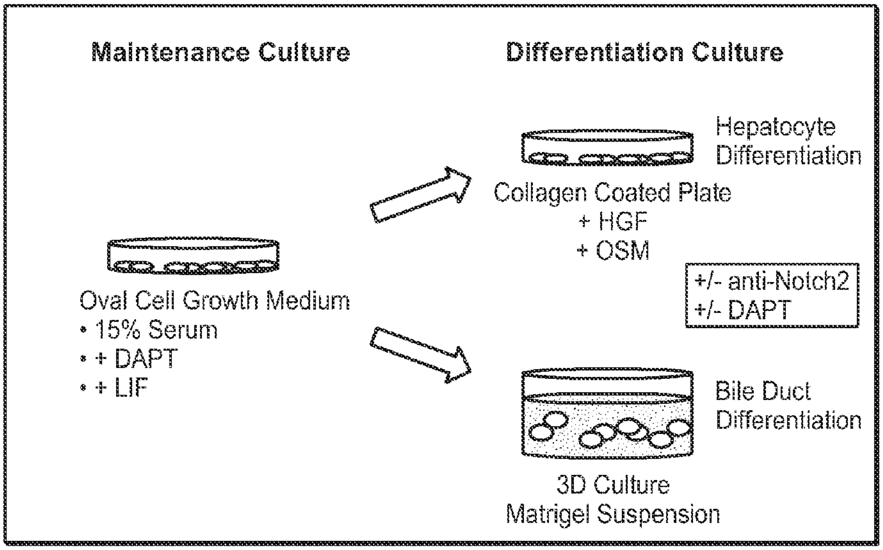
FIGS. 7A-B show a strategy for in vitro differentiation.
Figure 7B:
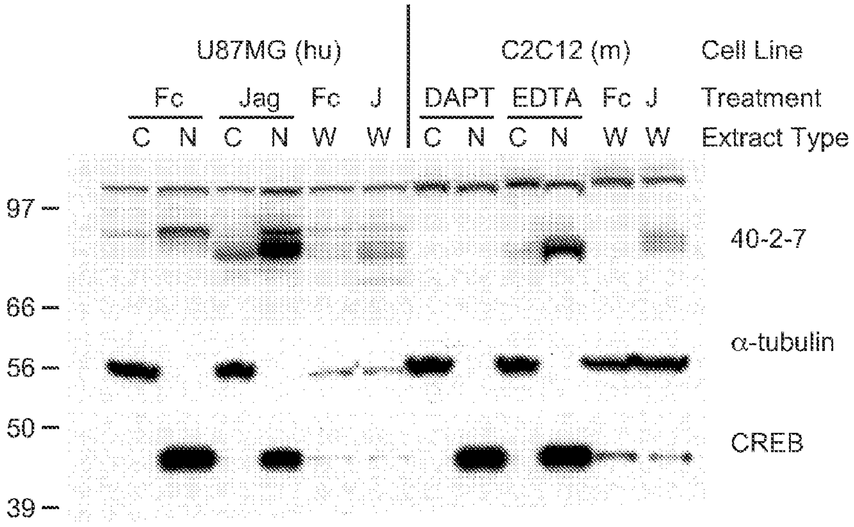

To determine if Notch signaling inhibition also suppresses the differentiation of progenitor cells, thereby allowing for long-term maintenance, the biliary and hepatic differentiation potential of these cells in vitro was analyzed (FIG. 7). Cultured oval cells were maintained on a mitomycin-C treated feeder layer of Swiss-3T3 fibroblasts by culture in the presence of 15% Fetal Bovine Serum (FBS) and the γ-secretase inhibitor DAPT.

Differentiation along the hepatocyte lineage was induced by plating oval cells without feeder cells onto tissue-culture treated plastic coated with diluted Rat Tail Collagen (BD) in the presence of 10 ng/ml Oncostatin M (R&D) and 25 ng/mL HGF (Lonza). For some experiments, DAPT or vehicle (DMSO) and/or the anti-Notch2 NRR antibody, Antibody D-3 (also referred to herein as anti-N2, anti-Notch2, or anti-NRR2) or an isotype control antibody were added to the medium at the time of cell plating and replenished every three days. Bile duct differentiation was induced by suspending oval cells in a 1:1 mixture of MATRIGEL and oval cell growth medium supplemented with 7.5% FBS and plating onto plastic tissue culture dishes. Following solidification, the MATRIGEL cultures were overlain with growth medium supplemented with 15% FBS. In some experiments, DAPT or vehicle and/or anti-Notch2 antibody or isotype control were added to the MATRIGEL as well as the overlying medium, which was replenished every three days.

Figure 2E:
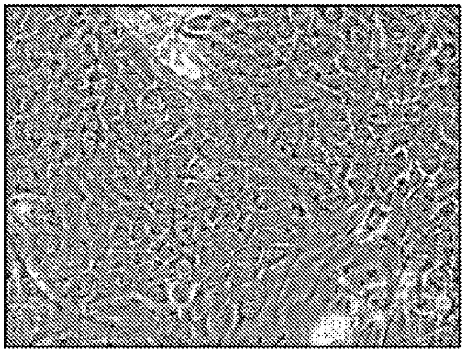
Figure 2F:
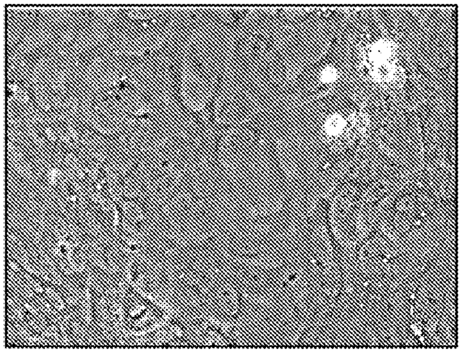
Figure 2G:
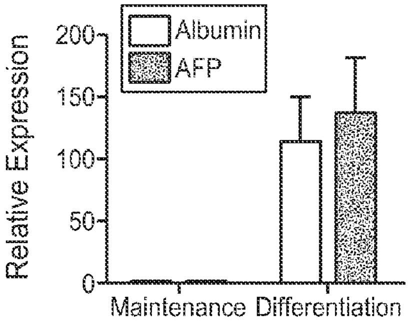
Figure 2H:
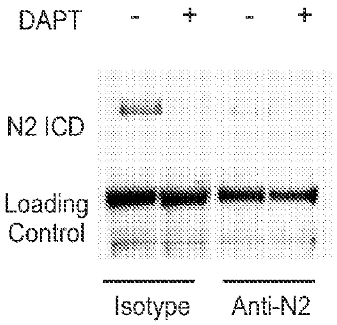
Figure 2I:
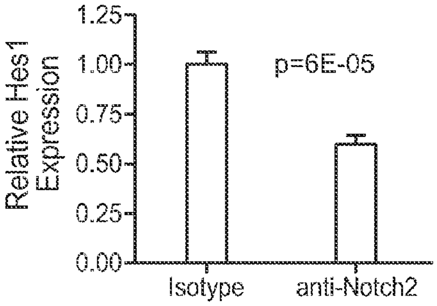
Figure 2J:
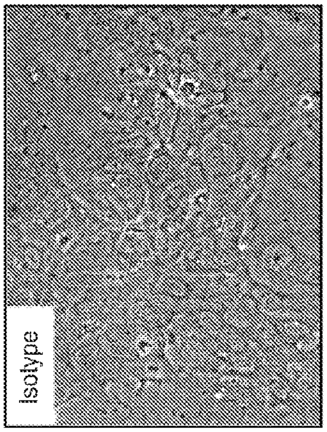
Figure 2K:
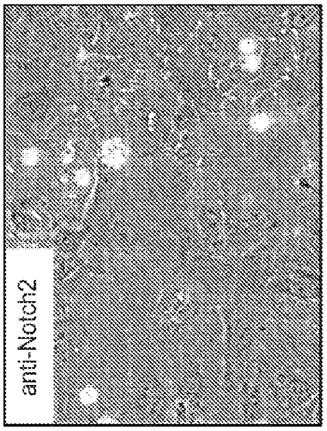
Figure 2L:
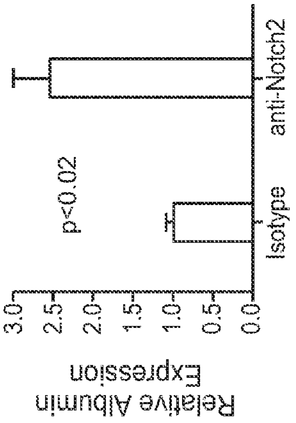

Progenitor cells that were cultured on a collagen substrate in the presence of Hepatocyte Growth Factor and Oncostatin M displayed a changed cellular morphology consistent with hepatocyte differentiation, including larger cell size, lower nuclear-cytoplasmic ratio, and two nuclei (FIG. 2E-F). Hepatocyte-associated transcripts Albumin and α-Fetoprotein (AFP; FIG. 2G) were also increased in these cells. Notch2 signaling was active in cultured oval cells, as transcriptionally active Notch2 intracellular domain (ICD) could be detected using an antibody specific to the γ-secretase cleaved form of this receptor (FIG. 2H). The appearance of the cleaved form was dependent on γ-secretase activity, as it was absent from DAPT treated cells (FIG. 2H). Specific binding of an anti-Notch2 inhibitory antibody also blocked formation of this active form of Notch2 (FIG. 2H). As expected, treatment with the Notch2 inhibitory antibody leads to a decrease in Notch target gene Hes1 (p=6E-05) (FIG. 2I). Surprisingly, progenitor cells that were cultured on a collagen substrate in the presence of Hepatocyte Growth Factor and Oncostatin M in the presence of an anti-Notch2 inhibitory antibody (Wu et al., Nature 464 (7291):1052 (2010)) (FIG. 2H-I) resulted in a more pronounced hepatocyte-like morphology (FIG. 2 K) and increased albumin expression level (FIG. 2L), compared to cells cultured with the isotype control (FIG. 2J, L).

Figure 2M:
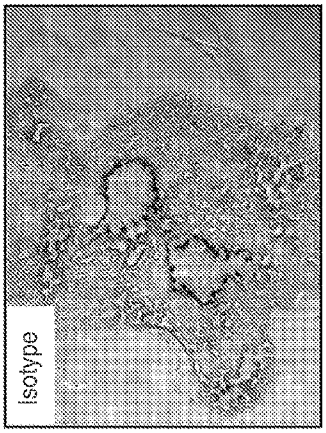
Figure 2N:
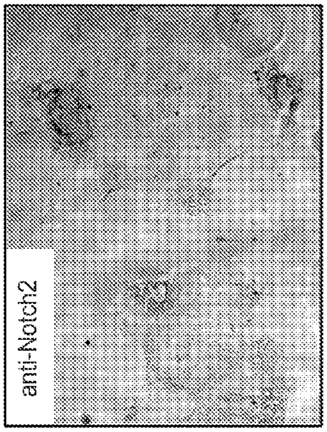
Figure 2O:
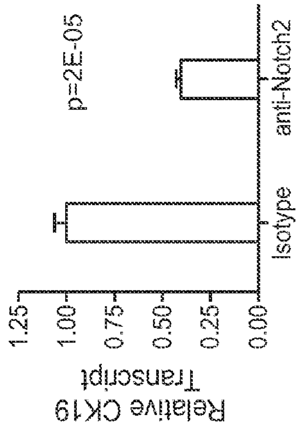

In contrast, differentiation of cultured oval cells along the biliary lineage, assessed in three dimensional culture, was decreased by inhibition of Notch2. Cells cultured in the presence of an anti-Notch2 inhibitory antibody displayed a less differentiated morphology (FIG. 2N) and a 50% decreased expression of the biliary marker Keratin 19 (CK19) (p=2E-05) (FIG. 2O) compared to cells grown in the absence of the inhibitory antibody (FIG. 2M, O). Together, these results are consistent with the notion that Notch2 inhibition biases differentiation away from the biliary lineage and toward hepatocyte formation.

Example 4: Inhibition of Notch2 Signaling In Vivo

To determine the effect of Notch2 inhibition in liver damage, a rodent model of liver damage was employed. Mice were partially hepatectomized by removal of left lateral and median lobes according to Yokoyama et al. (Yokoyama et al., Cancer Research 13(1):80-85 (1953)), which results in compensatory proliferation of hepatocytes and recovery of liver mass within 7-10 days (Higgins and Anderson, Arch. Pathol., 12:186 (1931); Yokoyama et al., Cancer Res. 13(1):80 (1953)). Mice were injected intraperitoneally with an anti-Notch2 NRR antagonist antibody (Wu et al., Nature 464(7291):1052 (2010)) or an anti-Ragweed isotype control antibody at a dose of 5 mg/kg twice per week, including twice prior to hepatectomy. Two hours prior to liver harvest, mice were injected intraperitoneally with Bromodeoxyuridine at 50 mg/kg. Immunohistochemistry was performed on 5 μm liver sections using antibodies for BrdU (DAKO), pan-Cytokeratin (WSS; DAKO), and Hes1 (MBL International). Antibody binding was detected using standard streptavidin-HRP/DAB for BrdU and pan-Cytokeratin and tyramide signal amplification (TSA)/DAB for Hes1.

Figure 8A:
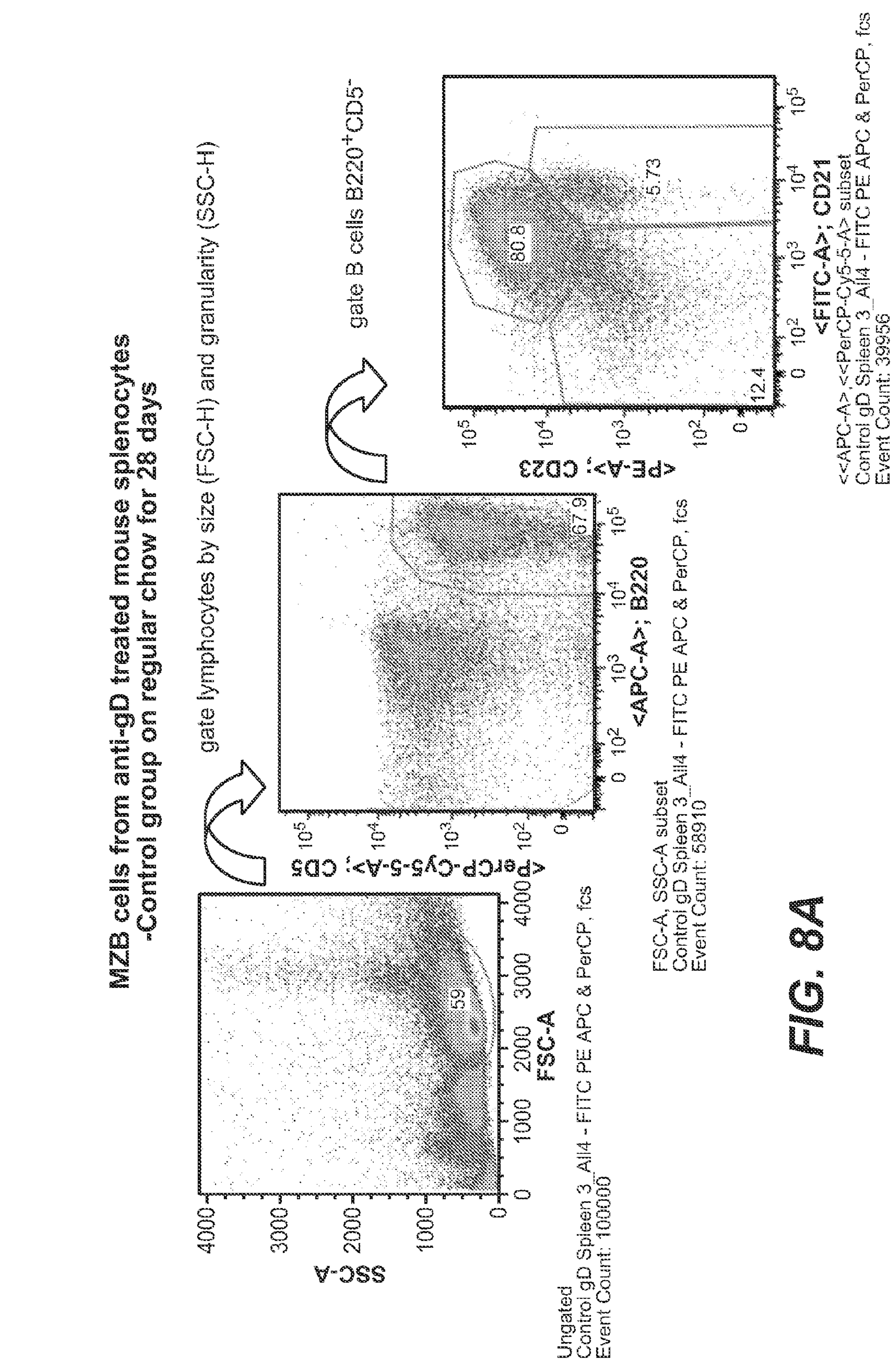
FIGS. 8A-F show the efficacy of anti-Notch2 antibody treatment in vivo and its effect on liver growth and proliferation following partial hepatectomy.
Figure 8B:
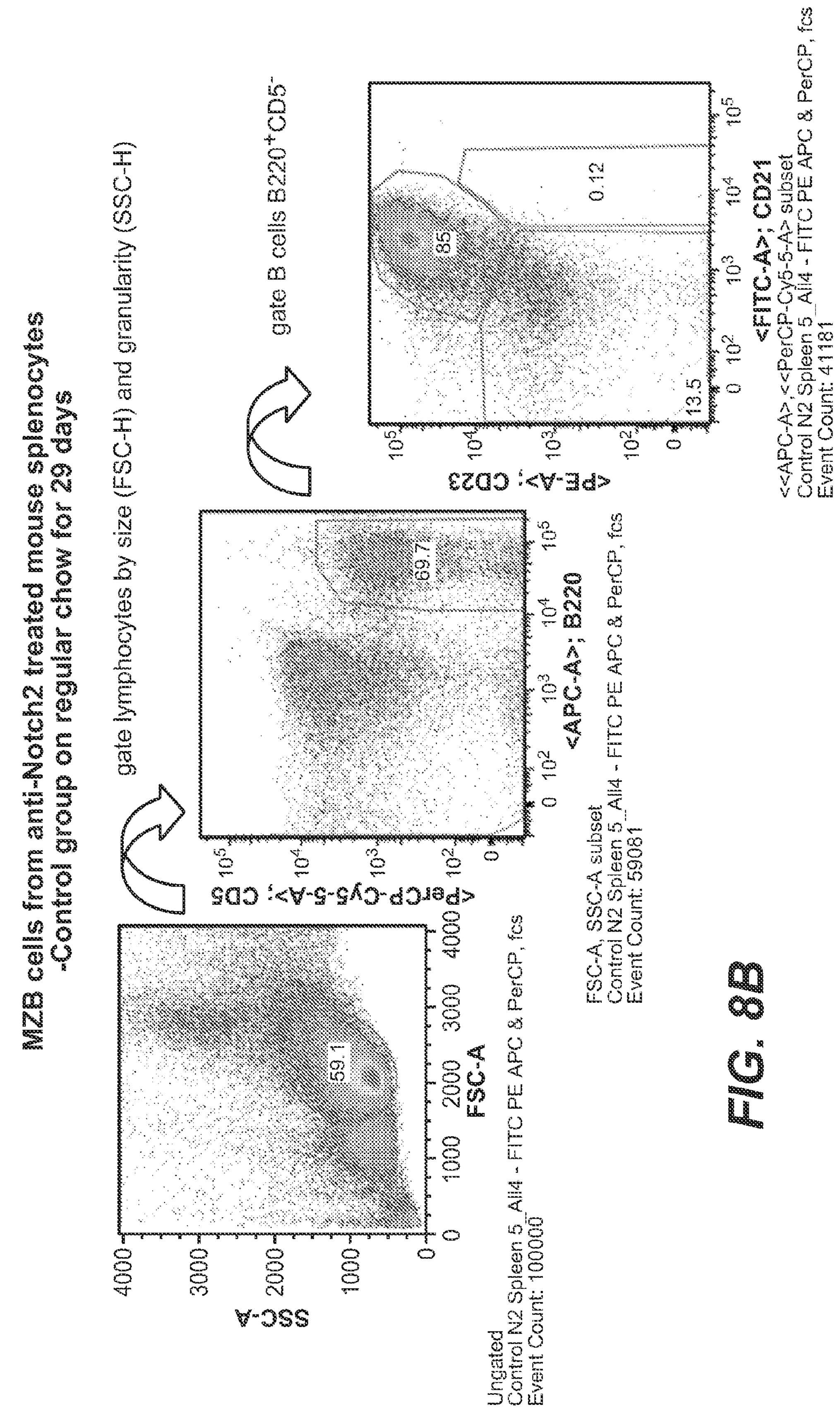
Figure 8C:
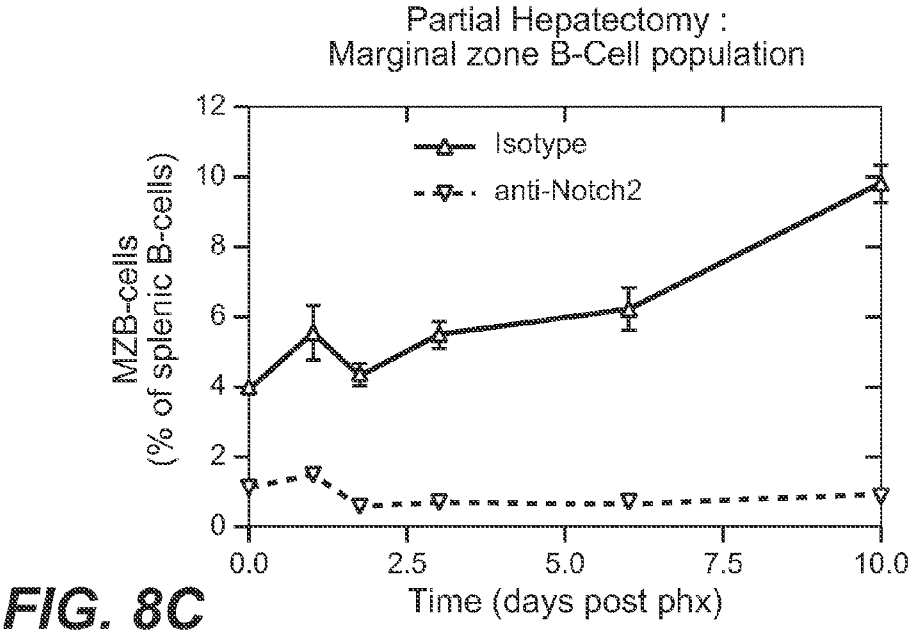
Figure 8D:
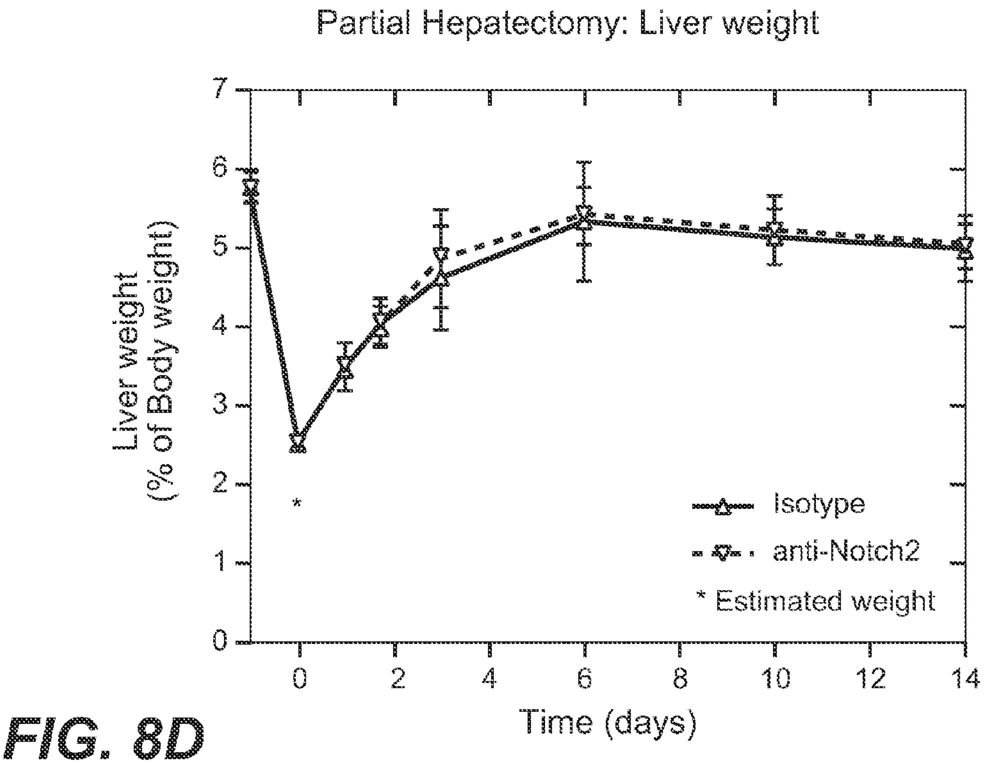
Figure 8E:
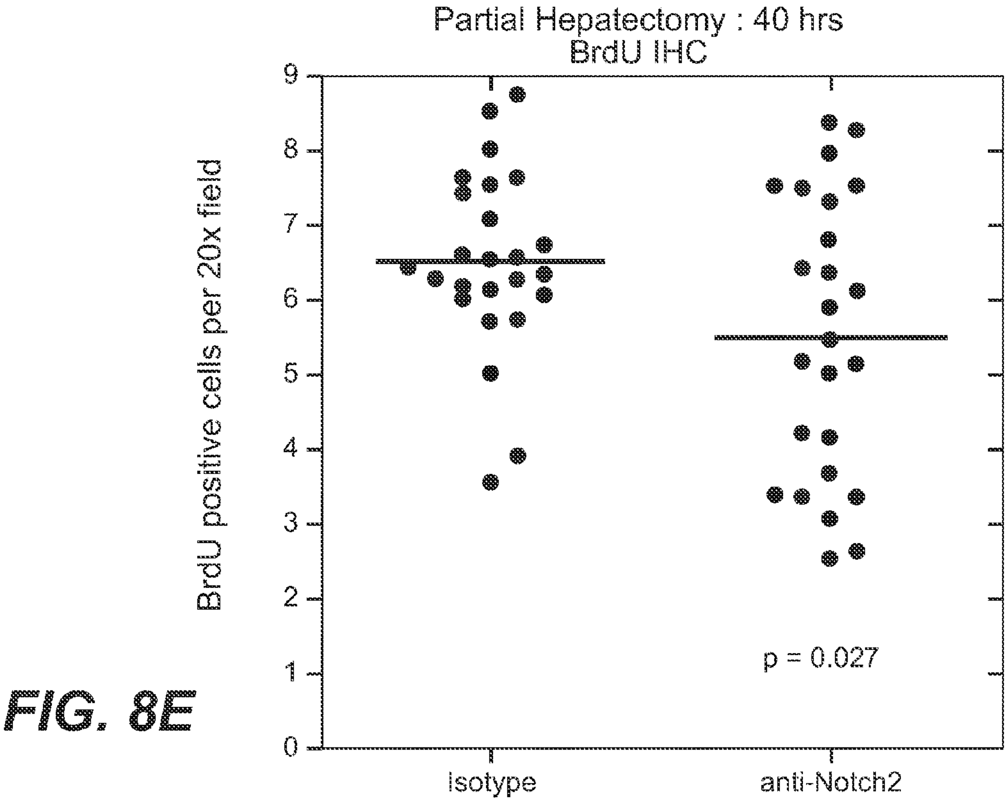
Figure 8F:
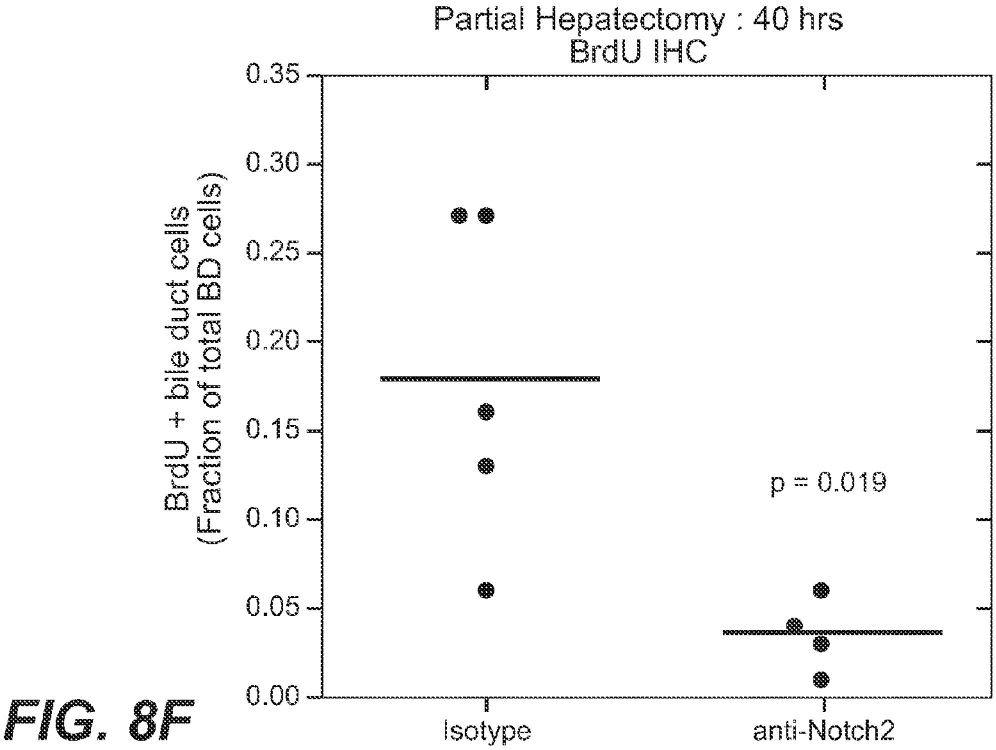
Figure 11A:
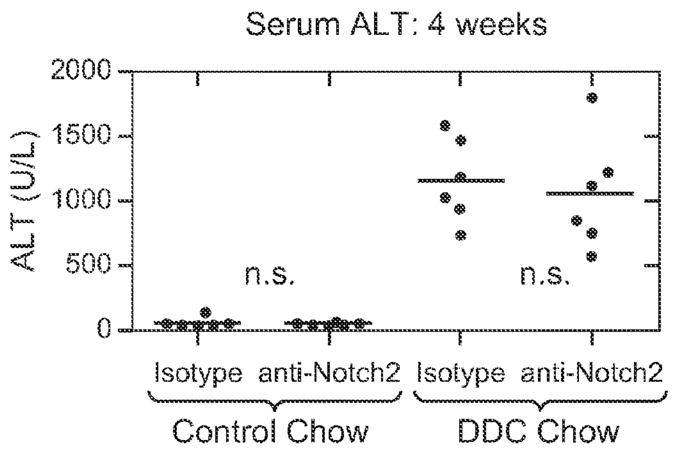
FIGS. 11A-I show serum hepatobiliary function markers following 4 weeks of antibody administration in normal and DDC-fed mice.
Figure 11B:
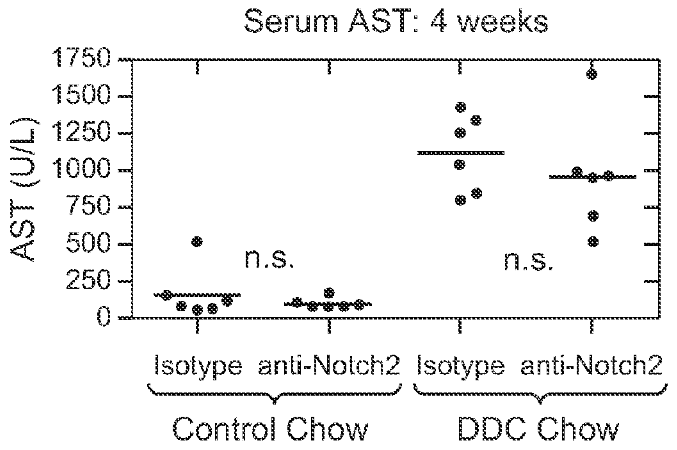
Figure 11C:
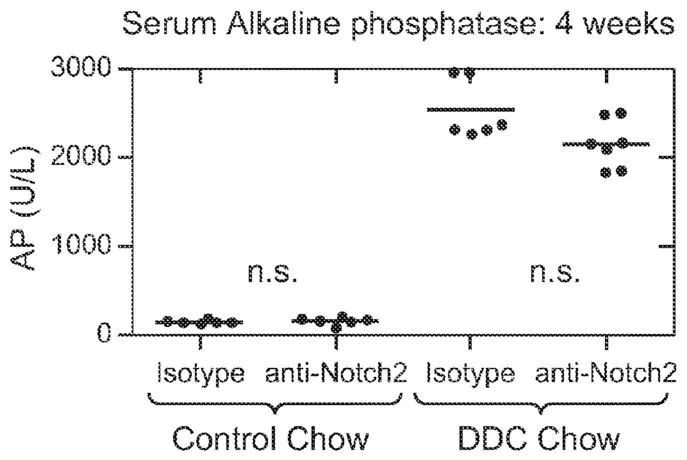
Figure 11D:
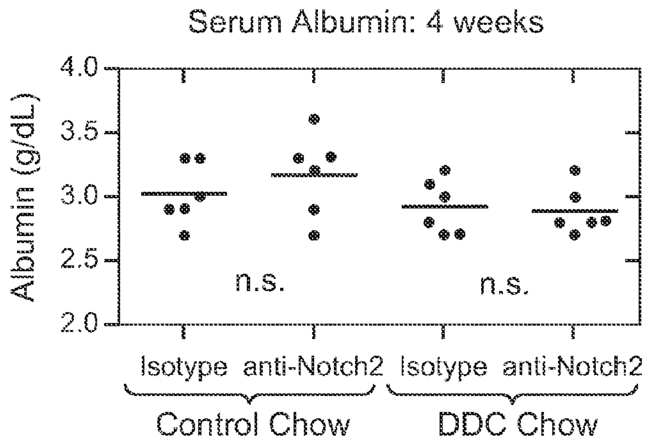
Figure 11E:
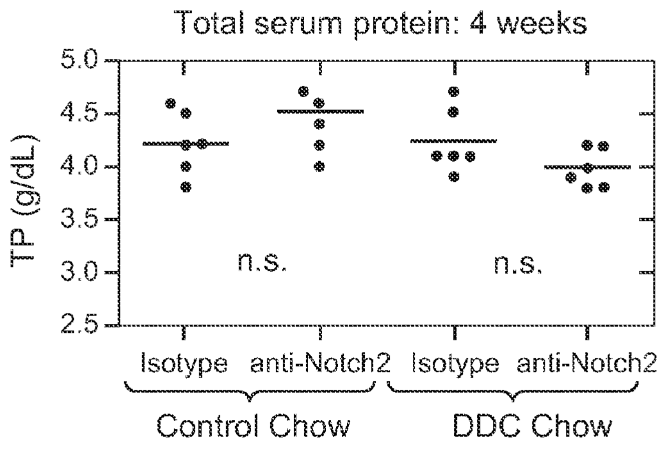
Figure 11F:
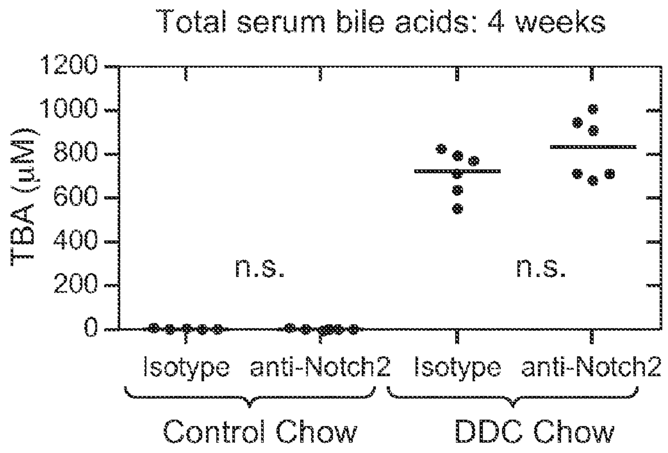
Figure 11G:
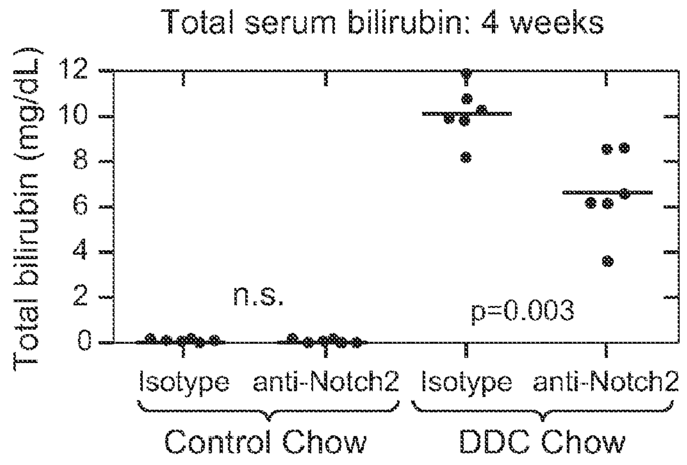
Figure 11H:
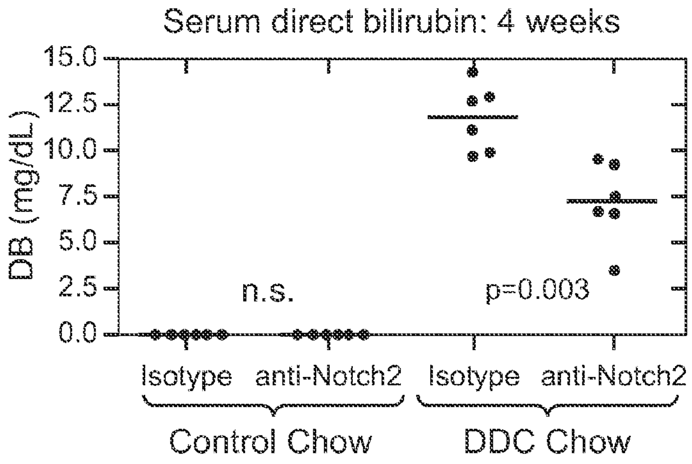
Figure 11I:
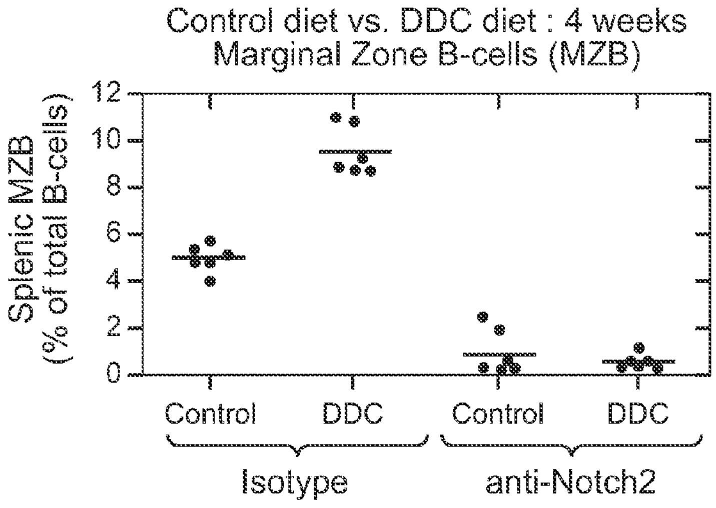

Treatment with anti-Notch2 antibody resulted in effective Notch2 inhibition as determined by significant splenic Marginal Zone B-cell (MZB) depletion ($p<0.0001$, FIG. 8A-C) (Wu et al.). MZB represent approximately 5% of the splenic B lymphocytes in normal C57Bl/6 mice. Treatment with Notch2 antagonist (5 mg/kg, 2×/week) resulted in a virtual disappearance of MZB (FIG. 8A-C). Notch2 inhibition was maintained through the course of partial hepatectomy experiments as indicated by persistent depression in MZB population (FIG. 8C). Inhibition of Notch2 did not significantly alter the rate of liver mass recovery immediately following partial hepatectomy (FIG. 8D), which in early stages is due largely to hepatocyte hypertrophy and division of pre-existing polyploid hepatocytes (St. Aubin and Bucher, The Anatomical Record 112(4):797 (1952); Higgins and Ingle, The Anatomical Record, 73(1):95 (1939)). Notch2 inhibition caused a small decrease in overall BrdU incorporation at 40 hours (FIG. 8E; (p=0.027)) and a much larger and more significant decrease in BrdU incorporation in intrahepatic bile ducts (FIG. 8F), suggesting that anti-Notch2 treatment affected liver progenitor cells within the bile ducts. Consistent with this observation, expression of the Notch target gene Hes1 was detected primarily in intra-hepatic bile duct cells (FIG. 3C-1) rather than in hepatocytes. Moreover, the percent Hes1-positive intrahepatic bile duct cells was significantly reduced in anti-Notch2 treated mice 40 hours after surgery, compared to control antibody treated mice, and in many portal areas Hes1 staining was not observed (FIG. 3C-2). Despite the reduction in Hes1-positive cells, bile duct morphology was unaffected (FIG. 3, compare panels A-1-D-1 on left (isotype) to panels A-2-D-2 on right (anti-Notch2)) and no significant elevation of markers of biliary dysfunction was observed, even after one month of ongoing Notch2 inhibition (FIG. 11F-H).

Example 5: Effects of Notch2 Inhibition on Liver Regeneration In Vivo

Figure 3E:
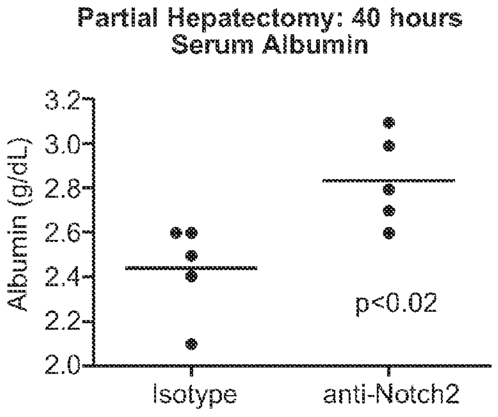
Figure 3F:
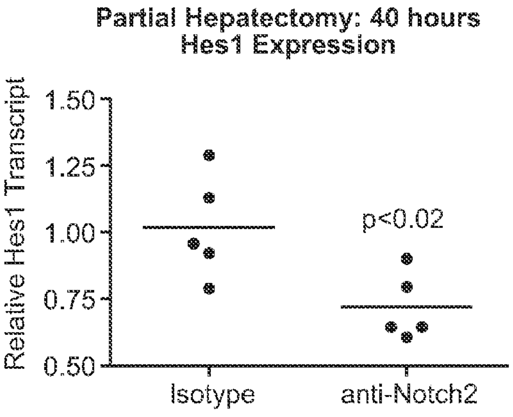
Figure 9A:
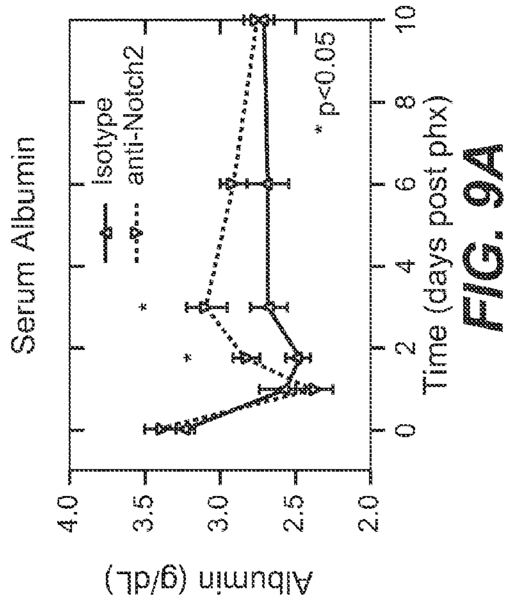
FIGS. 9A-H show the effect of anti-Notch2 antibody treatment on serum hepatobiliary function markers following partial hepatectomy.
Figure 9B:
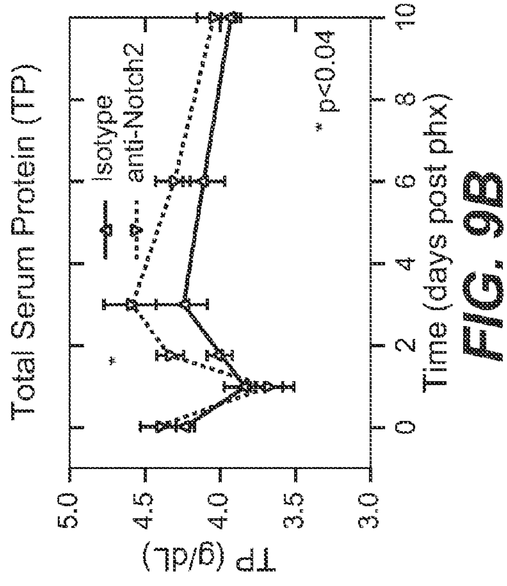
Figure 9C:
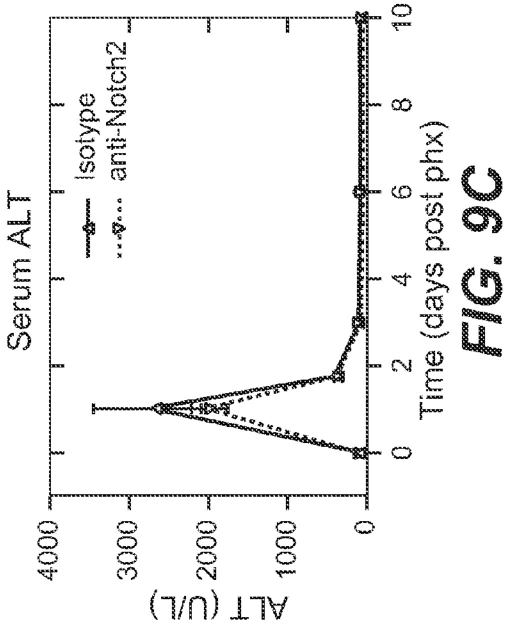
Figure 9D:
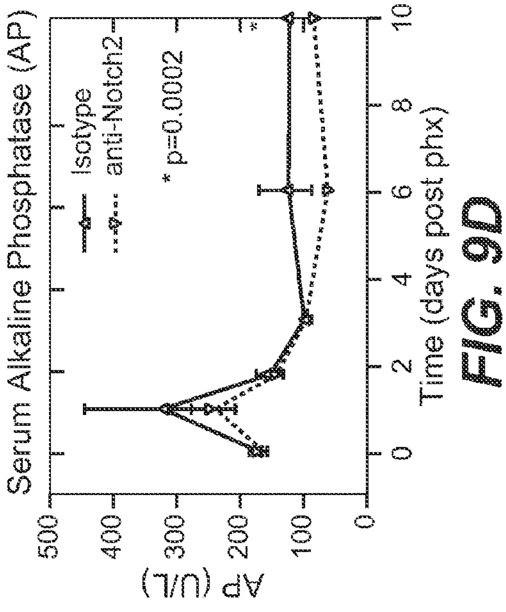
Figure 9E:
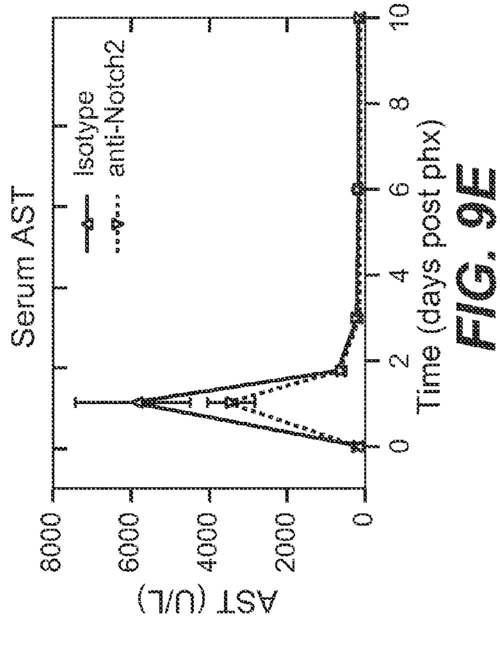
Figure 9F:
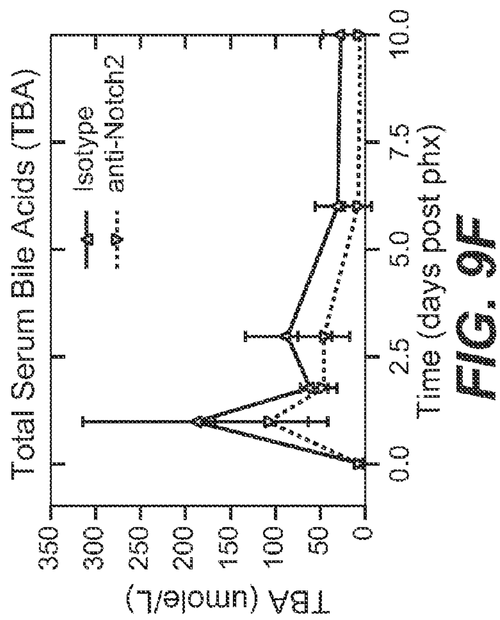
Figure 9G:
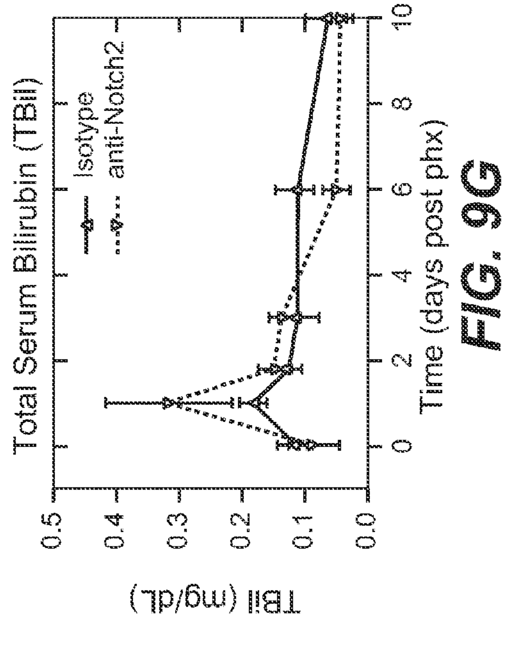
Figure 9H:
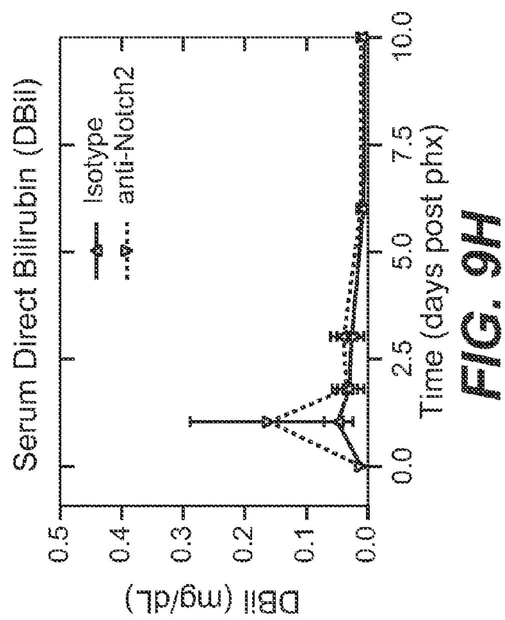
Figure 10A:
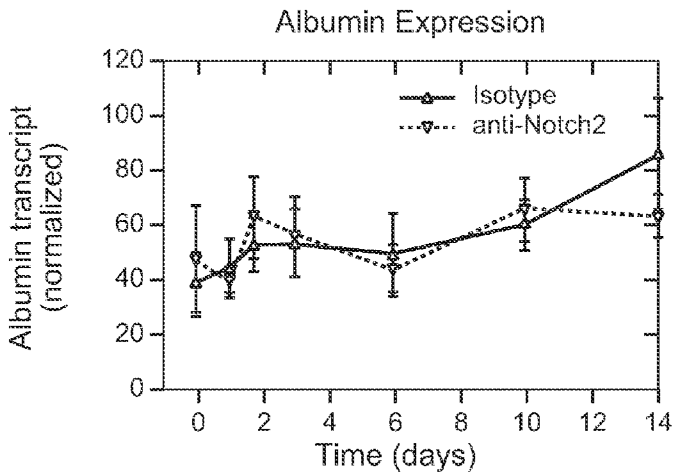
FIGS. 10A-F show the effect of anti-Notch2 antibody treatment on hepatobiliary and Notch signaling gene expression following partial hepatectomy.
Figure 10C:
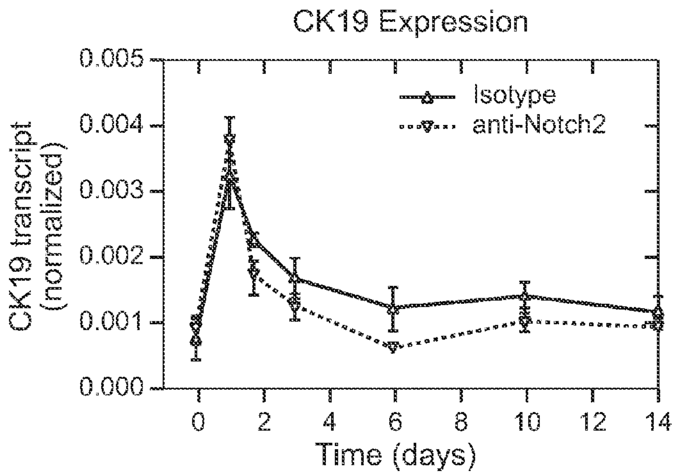
Figure 10E:
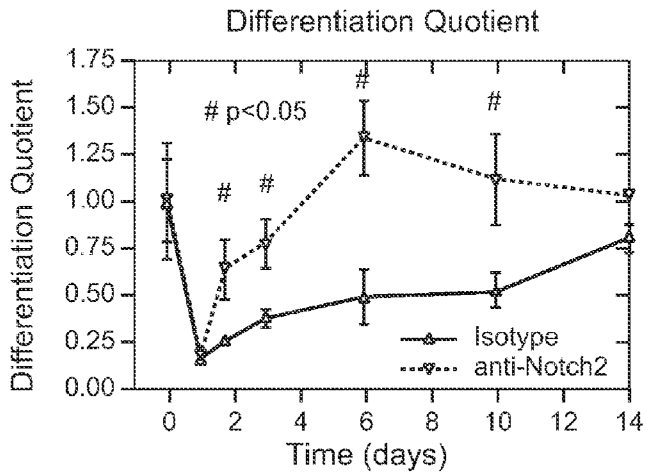
Figure 10B:
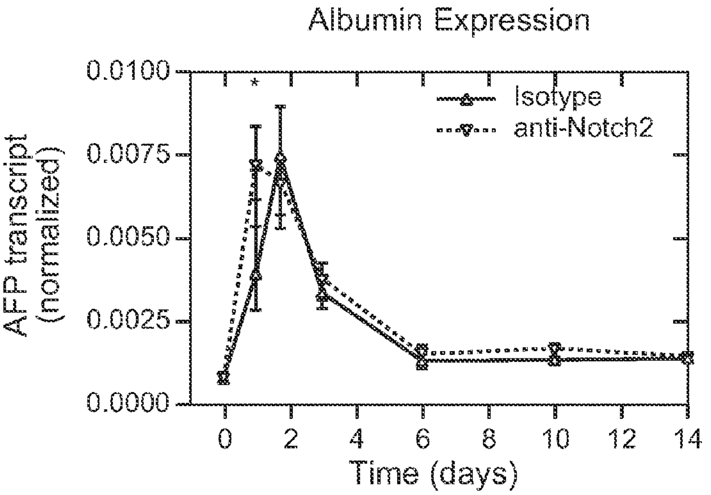
Figure 10D:
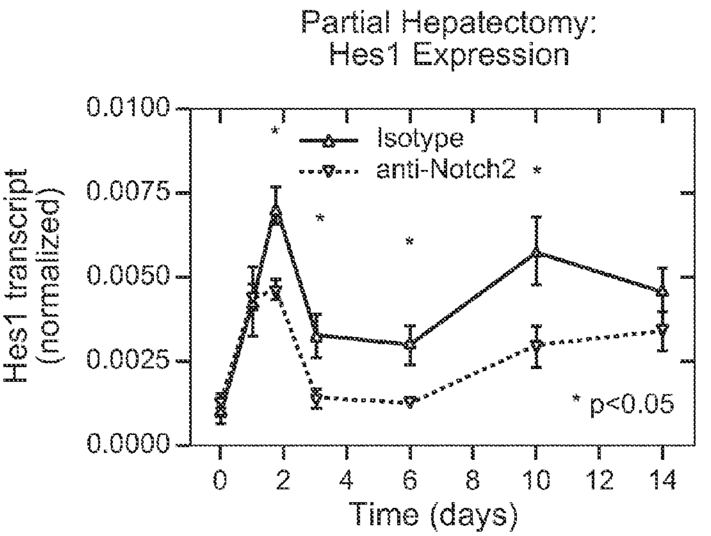
Figure 10F:
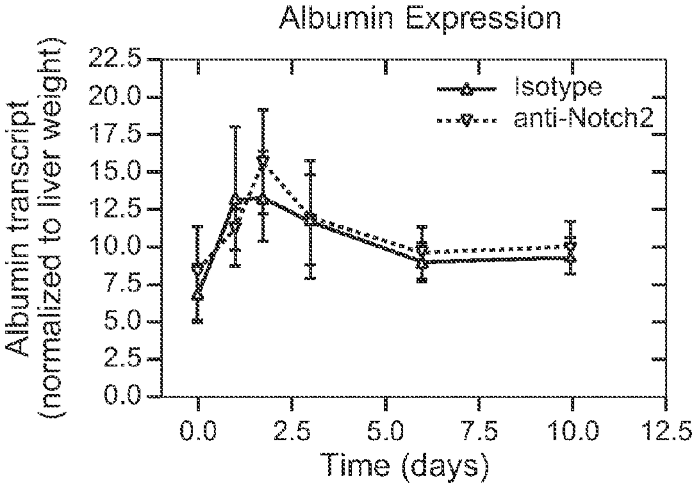

To determine whether Notch2 inhibition affects the recovery of hepatocyte function following partial hepatectomy, serum hepatobiliary function markers were assessed following ⅔ partial hepatectomy in mice treated with anti-Notch2 or control antibody. Unexpectedly, recovery in liver function began earlier in anti-Notch2-treated animals compared to controls. Serum albumin levels started increasing by 40 hours post surgery (FIG. 9A) and reached significantly ($p<0.05$) higher levels in anti-Notch2 antibody-treated mice at both the 40 hour and 72 hour time points (FIG. 3E; FIG. 9A), compared to serum levels in control animals that started to increase by 72 hours after surgery (2.8 versus 2.4 g/dL, $p<0.02$). This improvement in recovery of pre-operative serum albumin levels was accompanied by reduced expression of Hes1 ($p<0.02$; FIG. 3F). These results suggest that Notch2 inhibition results in enhanced recovery of hepatocyte function. Markers of hepatocyte damage were not significantly different between treatment and control groups (FIG. 5B-F). However, a consistent and significant increase in the ratio of albumin to K19 transcripts, referred to herein as Differentiation Quotient, was observed (FIG. 10E). The average Differentiation Quotient of anti-Notch2 antibody-treated livers, normalized to pre-surgical levels, recovered more quickly, regaining 75% of pre-surgical values 3 days after surgery and 100% of pre-surgical values between 3 and 6 days after surgery (FIG. 10E). In contrast, Differentiation Quotient values in isotype control antibody-treated animals did not recover to pre-surgical levels until 14 days after surgery (FIG. 10E). These results suggest that inhibition of Notch2 biases the differentiation of bipotent liver progenitor cells away from the biliary (K19-positive) towards the hepatic (albumin-positive) lineage. Differences between anti-Notch2 and isotype control antibody-treated livers in apparent de novo hepatocyte formation could be detected as early as 24 hours after partial hepatectomy. Transcript levels of in the form of the immature hepatocyte marker alpha-fetoprotein (AFP) were significantly elevated in anti-Notch2 antibody-treated mice (FIG. 10B). Also, morphological and functional differences between anti-Notch2 and control antibody-treated livers persisted for up to 2 weeks after surgery as the anti-Notch2 antibody-treated livers appeared more robust, with a noticeably more uniform parenchymal architecture (FIG. 3A-2) compared to control-treated livers (FIG. 3A-1).

The effects of Notch2 inhibition on liver regeneration were also studied in a 3,5-diethoxycarbonyl-1,4-dihydrocollidine (DDC) model of chronic liver disease. This DDC model is known in the art as a model of chronic liver disease. The mechanism of liver damage in response to DDC is abnormal heme metabolism with accumulation of protoporphyrin which is toxic to the hepatocytes. Thus, the DDC model can also serve as model for hereditary or acquired defects in the heme metabolic pathway.

Figure 3G:
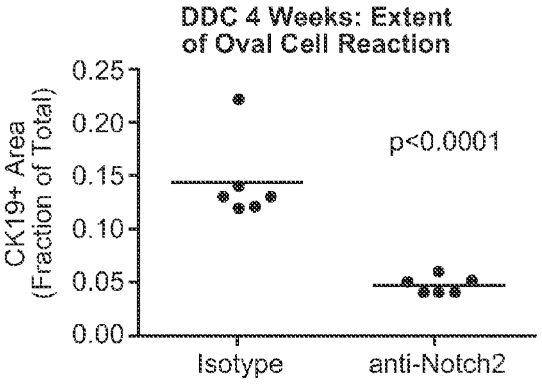
Figure 3H:
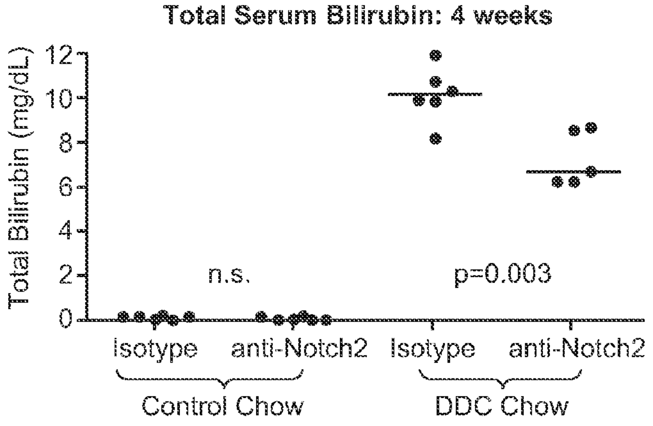
Figure 3I:
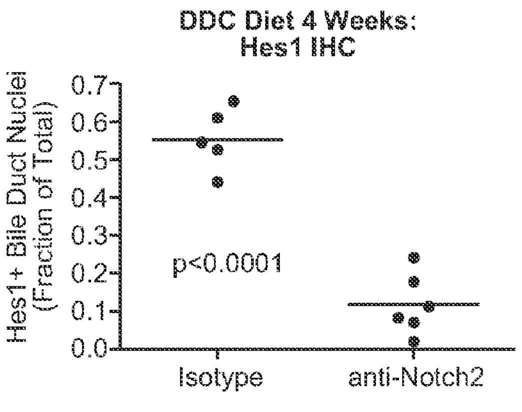
Figure 3J:
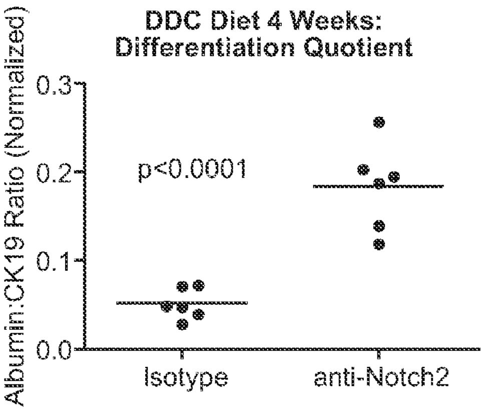

C57BL/6N female mice 8-12 weeks of age (Charles River) were fed a choline deficient diet (20% Lard; Teklad TD.04523) supplemented with 0.15% (w/v) Ethionine (supplier) in the drinking water to induce oval cells (Akhurst et al., Hepatology 34(3):519 (2001)). The prolonged hepatotoxic influence of a DDC diet led to a proliferation of cytokeratin (CK)19-positive progenitor cells (FIG. 3D-1), referred to as oval cell response, reminiscent of the ductular reaction common in human hepatobiliary disease (Farber, Cancer Research, 16(2):142 (1956)). After four weeks of DDC, the oval cell reaction had increased such that CK19-positive oval cells occupied an average of about 15% (10-20%) of the total hepatic cross sectional area (FIG. 3D-1; FIG. 3G), while serum markers of hepatobiliary injury were greatly elevated ($p<0.0001$, FIG. 3H; FIG. 11 A-H). However, treatment with the anti-Notch2 inhibitory antibody significantly impeded the oval cell reaction (FIG. 3D-2), reducing the average cross-sectional area of CK19-positive tissue from approximately 15% to only 5% of total liver cross sectional area ($p<0.0001$, FIG. 3G). Despite this striking reduction in oval cell proliferation, hepatic architecture was not adversely affected by anti-Notch2 antibody treatment and was grossly indistinguishable from control-treated tissue (FIG. 3D-2). The decrease in CK19-positive oval cells associated with Notch 2 inhibition was accompanied by improved hepatobiliary function, with significantly decreased total and direct serum bilirubin levels, a marker of cholestasis and other forms of hepatobiliary damage ($p=0.0003$, FIG. 3H). Also, the Differentiation Quotient was significantly elevated in livers from mice treated with the anti-Notch2 antibody ($p<0.0001$, FIG. 3J) suggesting improved hepatocyte function Inhibition of Notch2 signaling by treatment with an anti-Notch2 antibody was confirmed by a greater than 70% reduction in Hes1 expression in the biliary and progenitor cells in anti-Notch2 antibody-treated livers ($p<0.0001$, FIG. 3I), reflecting the central role of Notch2 signaling in governing oval cell fate choice.

Taken together, these results show that treatment with anti-Notch2 NRR antibody facilitates the recovery of liver function after two different types of liver damage, one by partial hepatectomy and one by chemical damage (choline-limiting diet). Mechanistically, anti-Notch2 NRR antibody facilitates liver recovery by favoring hepatocyte differentiation and by preventing aberrant (or pathologic) bile duct proliferation. Accordingly, treatment with anti-Notch2 NRR antibody could, e.g., prevent progression of chronic liver disease, such as liver fibrosis.

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

SEQUENCE LISTING

<160> NUMBER OF SEQ ID NOS: 74

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic HVR-H1 of Antibody D peptide"

<400> SEQUENCE: 1

Gly Tyr Ser Phe Thr Ser Tyr Gly Met Ser
1 5 10

<210> SEQ ID NO 2
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic HVR-H1 of Antibodies D-1, D-2, and D-3 peptide"

<400> SEQUENCE: 2

Gly Tyr Thr Phe Ser Ser Tyr Gly Met Ser
1 5 10

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic HVR-H1 Consensus sequence"
<220> FEATURE:
<221> NAME/KEY: VARIANT
<222> LOCATION: (3)..(3)
<223> OTHER INFORMATION: /replace="Thr"
<220> FEATURE:
<221> NAME/KEY: MISC_FEATURE
<222> LOCATION: (3)..(3)
<223> OTHER INFORMATION: /note="Residue given in the sequence has no
preference with respect to that in the annotation for said
position"
<220> FEATURE:
<221> NAME/KEY: VARIANT
<222> LOCATION: (5)..(5)
<223> OTHER INFORMATION: /replace="Thr"
<220> FEATURE:
<221> NAME/KEY: MISC_FEATURE
<222> LOCATION: (5)..(5)
<223> OTHER INFORMATION: /note="Residue given in the sequence has no
preference with respect to that in the annotation for said
position"

<400> SEQUENCE: 3

Gly Tyr Ser Phe Ser Ser Tyr Gly Met Ser
1 5 10

<210> SEQ ID NO 4
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic HVR-H2 of Antibodies D, D-1, D-2, and D-3 peptide"

<400> SEQUENCE: 4

Ser Tyr Ile Tyr Pro Tyr Ser Gly Ala Thr Tyr Tyr Ala Asp Ser Val
1 5 10 15

Lys Gly

<210> SEQ ID NO 5
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic HVR-H3 of Antibodies D, D-1, D-2, and D-3 peptide"

<400> SEQUENCE: 5

His Ser Gly Tyr Tyr Arg Ile Ser Ser Ala Met Asp Val
1 5 10

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic HVR-L1 of Antibody D peptide"

<400> SEQUENCE: 6

Arg Ala Ser Gln Ser Ile Ser Ser Tyr Leu Ala
1 5 10

<210> SEQ ID NO 7
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic HVR-L1 of Antibody D-1 peptide"

<400> SEQUENCE: 7

Arg Ala Ser Gln Ser Asn Arg Arg Phe Leu Ala
1 5 10

<210> SEQ ID NO 8
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic HVR-L1 of Antibody D-2 peptide"

<400> SEQUENCE: 8

Arg Ala Ser Gln Ser Val Arg Ser Phe Leu Ala
1 5 10

<210> SEQ ID NO 9
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic HVR-L1 of Antibody D-3 peptide"

<400> SEQUENCE: 9

Arg Ala Ser Gln Asn Ile Lys Arg Phe Leu Ala
1 5 10

```
<210> SEQ ID NO 10
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic HVR-L1 consensus sequence"
<220> FEATURE:
<221> NAME/KEY: VARIANT
<222> LOCATION: (5)..(5)
<223> OTHER INFORMATION: /replace="Asn"
<220> FEATURE:
<221> NAME/KEY: VARIANT
<222> LOCATION: (6)..(6)
<223> OTHER INFORMATION: /replace="Asn" or "Val"
<220> FEATURE:
<221> NAME/KEY: VARIANT
<222> LOCATION: (7)..(7)
<223> OTHER INFORMATION: /replace="Arg" or "Lys"
<220> FEATURE:
<221> NAME/KEY: VARIANT
<222> LOCATION: (8)..(8)
<223> OTHER INFORMATION: /replace="Arg"
<220> FEATURE:
<221> NAME/KEY: VARIANT
<222> LOCATION: (9)..(9)
<223> OTHER INFORMATION: /replace="Phe"
<220> FEATURE:
<221> NAME/KEY: MISC_FEATURE
<222> LOCATION: (5)..(9)
<223> OTHER INFORMATION: /note="Residues given in the sequence have no
      preference with respect to those in the annotations for said
      positions"

<400> SEQUENCE: 10

Arg Ala Ser Gln Ser Ile Ser Ser Tyr Leu Ala
1               5                   10


<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic HVR-L2 of Antibodies D and D-1 peptide"

<400> SEQUENCE: 11

Gly Ala Ser Ser Arg Ala Ser
1               5


<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic HVR-L2 of Antibody D-2 peptide"

<400> SEQUENCE: 12

Arg Ala Ser Ile Arg Ala Ser
1               5


<210> SEQ ID NO 13
<211> LENGTH: 7
<212> TYPE: PRT
<213> ORGANISM: Artificial Sequence
<220> FEATURE:
<221> NAME/KEY: source
```

-continued

```
<223> OTHER INFORMATION: /note="Description of Artificial Sequence:
      Synthetic HVR-L2 of Antibody D-3 peptide"

<400> SEQUENCE: 13

Gly Ala Ser Thr Arg Glu Ser
1               5


<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic HVR-L2 Consensus sequence"
<220> FEATURE:
<221> NAME/KEY: VARIANT
<222> LOCATION: (1)..(1)
<223> OTHER INFORMATION: /replace="Arg"
<220> FEATURE:
<221> NAME/KEY: MISC_FEATURE
<222> LOCATION: (1)..(1)
<223> OTHER INFORMATION: /note="Residue given in the sequence has no
      preference with respect to that in the annotation for said
      position"
<220> FEATURE:
<221> NAME/KEY: VARIANT
<222> LOCATION: (4)..(4)
<223> OTHER INFORMATION: /replace="Ile" or "Thr"
<220> FEATURE:
<221> NAME/KEY: MISC_FEATURE
<222> LOCATION: (4)..(4)
<223> OTHER INFORMATION: /note="Residue given in the sequence has no
      preference with respect to that in the annotation for said
      position"
<220> FEATURE:
<221> NAME/KEY: VARIANT
<222> LOCATION: (6)..(6)
<223> OTHER INFORMATION: /replace="Glu"
<220> FEATURE:
<221> NAME/KEY: MISC_FEATURE
<222> LOCATION: (6)..(6)
<223> OTHER INFORMATION: /note="Residue given in the sequence has no
      preference with respect to that in the annotation for said
      position"

<400> SEQUENCE: 14

Gly Ala Ser Ser Arg Ala Ser
1               5


<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic HVR-L3 of Antibody D peptide"

<400> SEQUENCE: 15

Gln Gln Tyr Tyr Ser Ser Pro Leu Thr
1               5


<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic HVR-L3 of Antibody D-1 peptide"

<400> SEQUENCE: 16
```

Gln Gln Tyr Tyr Ile Ser Pro Leu Thr
1 5

<210> SEQ ID NO 17
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic HVR-L3 of Antibody D-2 peptide"

<400> SEQUENCE: 17

Gln Gln Tyr Tyr Ile Ser Pro Trp Thr
1 5

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic HVR-L3 of Antibody D-3 peptide"

<400> SEQUENCE: 18

Gln Gln Tyr Tyr Arg Ser Pro His Thr
1 5

<210> SEQ ID NO 19
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic HVR-L3 consensus sequence"
<220> FEATURE:
<221> NAME/KEY: VARIANT
<222> LOCATION: (5)..(5)
<223> OTHER INFORMATION: /replace="Ile" or "Arg"
<220> FEATURE:
<221> NAME/KEY: MISC_FEATURE
<222> LOCATION: (5)..(5)
<223> OTHER INFORMATION: /note="Residue given in the sequence has no preference with respect to that in the annotation for said position"
<220> FEATURE:
<221> NAME/KEY: VARIANT
<222> LOCATION: (8)..(8)
<223> OTHER INFORMATION: /replace="Trp" or "His"
<220> FEATURE:
<221> NAME/KEY: MISC_FEATURE
<222> LOCATION: (8)..(8)
<223> OTHER INFORMATION: /note="Residue given in the sequence has no preference with respect to that in the annotation for said position"

<400> SEQUENCE: 19

Gln Gln Tyr Tyr Ser Ser Pro Leu Thr
1 5

<210> SEQ ID NO 20
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Heavy chain variable region of Antibody D polypeptide"

<400> SEQUENCE: 20

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Phe Thr Ser Tyr
20 25 30

Gly Met Ser Trp Val Arg Gln Ala Pro Gly Lys Gly Leu Glu Trp Val
35 40 45

Ser Tyr Ile Tyr Pro Tyr Ser Gly Ala Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg His Ser Gly Tyr Tyr Arg Ile Ser Ser Ala Met Asp Val Trp
100 105 110

Gly Gln Gly Thr Leu Val Thr Val Ser Ala
115 120

<210> SEQ ID NO 21
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Heavy chain variable region of Antibodies D-1, D-2, and D-3 polypeptide"

<400> SEQUENCE: 21

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Phe Ser Ser Tyr
20 25 30

Gly Met Ser Trp Val Arg Gln Ala Pro Gly Lys Gly Leu Glu Trp Val
35 40 45

Ser Tyr Ile Tyr Pro Tyr Ser Gly Ala Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg His Ser Gly Tyr Tyr Arg Ile Ser Ser Ala Met Asp Val Trp
100 105 110

Gly Gln Gly Thr Leu Val Thr Val Ser Ala
115 120

<210> SEQ ID NO 22
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Light chain variable region of Antibody D polypeptide"

<400> SEQUENCE: 22

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr

-continued 20 25 30

Leu Ala Trp Tyr Gln Gln Lys Pro Gly Lys Ala Pro Lys Leu Leu Ile
35 40 45

Tyr Gly Ala Ser Ser Arg Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ser Ser Pro Leu
85 90 95

Thr Phe Gly Gln Gly Thr Lys Val Glu Ile Lys Arg
100 105

<210> SEQ ID NO 23
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Light chain variable region of Antibody D-1 polypeptide"

<400> SEQUENCE: 23

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Asn Arg Arg Phe
20 25 30

Leu Ala Trp Tyr Gln Gln Lys Pro Gly Lys Ala Pro Lys Leu Leu Ile
35 40 45

Tyr Gly Ala Ser Ser Arg Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Ser Pro Leu
85 90 95

Thr Phe Gly Gln Gly Thr Lys Val Glu Ile Lys Arg
100 105

<210> SEQ ID NO 24
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Light chain variable region of Antibody D-2 polypeptide"

<400> SEQUENCE: 24

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Arg Ser Phe
20 25 30

Leu Ala Trp Tyr Gln Gln Lys Pro Gly Lys Ala Pro Lys Leu Leu Ile
35 40 45

Tyr Arg Ala Ser Ile Arg Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Ser Pro Trp
85 90 95

Thr Phe Gly Gln Gly Thr Lys Val Glu Ile Lys Arg
100 105

<210> SEQ ID NO 25
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Light chain variable region of Antibody D-3 polypeptide"

<400> SEQUENCE: 25

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asn Ile Lys Arg Phe
20 25 30

Leu Ala Trp Tyr Gln Gln Lys Pro Gly Lys Ala Pro Lys Leu Leu Ile
35 40 45

Tyr Gly Ala Ser Thr Arg Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Arg Ser Pro His
85 90 95

Thr Phe Gly Gln Gly Thr Lys Val Glu Ile Lys Arg
100 105

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

Gly Val Pro Ser Arg Phe Ser Gly Ser Arg Ser Gly Thr Asp Phe Thr
1 5 10 15

-continued

Leu Thr Ile Ser Ser Leu Gln Pro Glu Asp Phe Ala Thr Tyr Tyr Cys
20 25 30

<210> SEQ ID NO 31
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic framework region 4 peptide"

<400> SEQUENCE: 31

Phe Arg Gln Gly Thr Lys Val Glu Ile Lys
1 5 10

<210> SEQ ID NO 32
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 32

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr
20 25 30

<210> SEQ ID NO 33
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 33

Trp Val Arg Gln Ala Pro Gly Gln Gly Leu Glu Trp Met Gly
1 5 10

<210> SEQ ID NO 34
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 34

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 35
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 35

Trp Gly Gln Gly Thr Leu Val Thr Val Ser Ser
1 5 10

<210> SEQ ID NO 36
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

Gln Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 37
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 37

Trp Val Arg Gln Ala Pro Gly Gln Gly Leu Glu Trp Met
1 5 10

<210> SEQ ID NO 38
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys Ala
20 25 30

<210> SEQ ID NO 39
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys
20 25 30

<210> SEQ ID NO 40
<211> LENGTH: 30
<212> TYPE: PRT

-continued

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Val Ser
20 25 30

<210> SEQ ID NO 41
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 41

Trp Ile Arg Gln Pro Pro Gly Lys Gly Leu Glu Trp Ile Gly
1 5 10

<210> SEQ ID NO 42
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

Arg Val Thr Ile Ser Val Asp Thr Ser Lys Asn Gln Phe Ser Leu Lys
1 5 10 15

Leu Ser Ser Val Thr Ala Ala Asp Thr Ala Val Tyr Tyr Cys Ala Arg
20 25 30

<210> SEQ ID NO 43
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 43

Gln Val Gln Leu Gln Glu Ser Gly Pro Gly Leu Val Lys Pro Ser Gln
1 5 10 15

Thr Leu Ser Leu Thr Cys Thr Val Ser
20 25

<210> SEQ ID NO 44
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 44

Trp Ile Arg Gln Pro Pro Gly Lys Gly Leu Glu Trp Ile
1 5 10

<210> SEQ ID NO 45
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30
```

<210> SEQ ID NO 46
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30
```

<210> SEQ ID NO 47
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 48
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 48

```
Trp Val Arg Gln Ala Pro Gly Lys Gly Leu Glu Trp Val Ser
1               5                   10
```

<210> SEQ ID NO 49
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 50
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 51
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Trp Val Arg Gln Ala Pro Gly Lys Gly Leu Glu Trp Val
1               5                   10

<210> SEQ ID NO 52
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala
            20                  25                  30

<210> SEQ ID NO 53
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

-continued

<210> SEQ ID NO 54
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30

<210> SEQ ID NO 55
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 55

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 56
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 56

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser
            20                  25                  30

<210> SEQ ID NO 57
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 57

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 58
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 58

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 59
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 59

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 60
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 61
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 61

Trp Tyr Gln Gln Lys Pro Gly Lys Ala Pro Lys Leu Leu Ile Tyr
1               5                   10                  15

<210> SEQ ID NO 62
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 62

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

```
<210> SEQ ID NO 63
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Phe Gly Gln Gly Thr Lys Val Glu Ile Lys
1               5                   10


<210> SEQ ID NO 64
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys
            20


<210> SEQ ID NO 65
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Trp Tyr Leu Gln Lys Pro Gly Gln Ser Pro Gln Leu Leu Ile Tyr
1               5                   10                  15


<210> SEQ ID NO 66
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30


<210> SEQ ID NO 67
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Glu Ile Val Leu Thr Gln Ser Pro Gly Thr Leu Ser Leu Ser Pro Gly
```

1 5 10 15

Glu Arg Ala Thr Leu Ser Cys
20

<210> SEQ ID NO 68
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 68

Trp Tyr Gln Gln Lys Pro Gly Gln Ala Pro Arg Leu Leu Ile Tyr
1 5 10 15

<210> SEQ ID NO 69
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 69

Gly Ile Pro Asp Arg Phe Ser Gly Ser Gly Ser Gly Thr Asp Phe Thr
1 5 10 15

Leu Thr Ile Ser Arg Leu Glu Pro Glu Asp Phe Ala Val Tyr Tyr Cys
20 25 30

<210> SEQ ID NO 70
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 70

Asp Ile Val Met Thr Gln Ser Pro Asp Ser Leu Ala Val Ser Leu Gly
1 5 10 15

Glu Arg Ala Thr Ile Asn Cys
20

<210> SEQ ID NO 71
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 71

Trp Tyr Gln Gln Lys Pro Gly Gln Pro Pro Lys Leu Leu Ile Tyr
1 5 10 15

<210> SEQ ID NO 72
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 72

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 73
<211> LENGTH: 2471
<212> TYPE: PRT
<213> ORGANISM: Homo sapiens

<400> SEQUENCE: 73

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser

-continued

```
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750
```

-continued

```
Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
        835                 840                 845

Lys Glu Ser Pro Asn Phe Glu Ser Tyr Thr Cys Leu Cys Ala Pro Gly
    850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
        915                 920                 925

Gly Val Asn Thr Phe Ser Cys Leu Cys Leu Pro Gly Phe Thr Gly Asp
    930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
            980                 985                 990

Glu Ser Ser Cys Phe Asn Gly Gly  Thr Cys Val Asp Gly  Ile Asn Ser
        995                 1000                1005

Phe Ser  Cys Leu Cys Pro Val  Gly Phe Thr Gly Ser  Phe Cys Leu
    1010                1015                1020

His Glu  Ile Asn Glu Cys Ser  Ser His Pro Cys Leu  Asn Glu Gly
    1025                1030                1035

Thr Cys  Val Asp Gly Leu Gly  Thr Tyr Arg Cys Ser  Cys Pro Leu
    1040                1045                1050

Gly Tyr  Thr Gly Lys Asn Cys  Gln Thr Leu Val Asn  Leu Cys Ser
    1055                1060                1065

Arg Ser  Pro Cys Lys Asn Lys  Gly Thr Cys Val Gln  Lys Lys Ala
    1070                1075                1080

Glu Ser  Gln Cys Leu Cys Pro  Ser Gly Trp Ala Gly  Ala Tyr Cys
    1085                1090                1095

Asp Val  Pro Asn Val Ser Cys  Asp Ile Ala Ala Ser  Arg Arg Gly
    1100                1105                1110

Val Leu  Val Glu His Leu Cys  Gln His Ser Gly Val  Cys Ile Asn
    1115                1120                1125

Ala Gly  Asn Thr His Tyr Cys  Gln Cys Pro Leu Gly  Tyr Thr Gly
    1130                1135                1140

Ser Tyr  Cys Glu Glu Gln Leu  Asp Glu Cys Ala Ser  Asn Pro Cys
    1145                1150                1155
```

-continued

```
Gln His  Gly Ala Thr Cys Ser  Asp Phe Ile Gly Gly  Tyr Arg Cys
    1160                 1165                 1170

Glu Cys  Val Pro Gly Tyr Gln  Gly Val Asn Cys Glu  Tyr Glu Val
    1175                 1180                 1185

Asp Glu  Cys Gln Asn Gln Pro  Cys Gln Asn Gly Gly  Thr Cys Ile
    1190                 1195                 1200

Asp Leu  Val Asn His Phe Lys  Cys Ser Cys Pro Pro  Gly Thr Arg
    1205                 1210                 1215

Gly Leu  Leu Cys Glu Glu Asn  Ile Asp Asp Cys Ala  Arg Gly Pro
    1220                 1225                 1230

His Cys  Leu Asn Gly Gly Gln  Cys Met Asp Arg Ile  Gly Gly Tyr
    1235                 1240                 1245

Ser Cys  Arg Cys Leu Pro Gly  Phe Ala Gly Glu Arg  Cys Glu Gly
    1250                 1255                 1260

Asp Ile  Asn Glu Cys Leu Ser  Asn Pro Cys Ser Ser  Glu Gly Ser
    1265                 1270                 1275

Leu Asp  Cys Ile Gln Leu Thr  Asn Asp Tyr Leu Cys  Val Cys Arg
    1280                 1285                 1290

Ser Ala  Phe Thr Gly Arg His  Cys Glu Thr Phe Val  Asp Val Cys
    1295                 1300                 1305

Pro Gln  Met Pro Cys Leu Asn  Gly Gly Thr Cys Ala  Val Ala Ser
    1310                 1315                 1320

Asn Met  Pro Asp Gly Phe Ile  Cys Arg Cys Pro Pro  Gly Phe Ser
    1325                 1330                 1335

Gly Ala  Arg Cys Gln Ser Ser  Cys Gly Gln Val Lys  Cys Arg Lys
    1340                 1345                 1350

Gly Glu  Gln Cys Val His Thr  Ala Ser Gly Pro Arg  Cys Phe Cys
    1355                 1360                 1365

Pro Ser  Pro Arg Asp Cys Glu  Ser Gly Cys Ala Ser  Ser Pro Cys
    1370                 1375                 1380

Gln His  Gly Gly Ser Cys His  Pro Gln Arg Gln Pro  Pro Tyr Tyr
    1385                 1390                 1395

Ser Cys  Gln Cys Ala Pro Pro  Phe Ser Gly Ser Arg  Cys Glu Leu
    1400                 1405                 1410

Tyr Thr  Ala Pro Pro Ser Thr  Pro Pro Ala Thr Cys  Leu Ser Gln
    1415                 1420                 1425

Tyr Cys  Ala Asp Lys Ala Arg  Asp Gly Val Cys Asp  Glu Ala Cys
    1430                 1435                 1440

Asn Ser  His Ala Cys Gln Trp  Asp Gly Gly Asp Cys  Ser Leu Thr
    1445                 1450                 1455

Met Glu  Asn Pro Trp Ala Asn  Cys Ser Ser Pro Leu  Pro Cys Trp
    1460                 1465                 1470

Asp Tyr  Ile Asn Asn Gln Cys  Asp Glu Leu Cys Asn  Thr Val Glu
    1475                 1480                 1485

Cys Leu  Phe Asp Asn Phe Glu  Cys Gln Gly Asn Ser  Lys Thr Cys
    1490                 1495                 1500

Lys Tyr  Asp Lys Tyr Cys Ala  Asp His Phe Lys Asp  Asn His Cys
    1505                 1510                 1515

Asp Gln  Gly Cys Asn Ser Glu  Glu Cys Gly Trp Asp  Gly Leu Asp
    1520                 1525                 1530

Cys Ala  Ala Asp Gln Pro Glu  Asn Leu Ala Glu Gly  Thr Leu Val
    1535                 1540                 1545

Ile Val  Val Leu Met Pro Pro  Glu Gln Leu Leu Gln  Asp Ala Arg
```

-continued

```
    1550                1555                1560

Ser Phe  Leu Arg Ala Leu Gly  Thr Leu Leu His Thr  Asn Leu Arg
    1565                1570                1575

Ile Lys  Arg Asp Ser Gln Gly  Glu Leu Met Val Tyr  Pro Tyr Tyr
    1580                1585                1590

Gly Glu  Lys Ser Ala Ala Met  Lys Lys Gln Arg Met  Thr Arg Arg
    1595                1600                1605

Ser Leu  Pro Gly Glu Gln Glu  Gln Glu Val Ala Gly  Ser Lys Val
    1610                1615                1620

Phe Leu  Glu Ile Asp Asn Arg  Gln Cys Val Gln Asp  Ser Asp His
    1625                1630                1635

Cys Phe  Lys Asn Thr Asp Ala  Ala Ala Ala Leu Leu  Ala Ser His
    1640                1645                1650

Ala Ile  Gln Gly Thr Leu Ser  Tyr Pro Leu Val Ser  Val Val Ser
    1655                1660                1665

Glu Ser  Leu Thr Pro Glu Arg  Thr Gln Leu Leu Tyr  Leu Leu Ala
    1670                1675                1680

Val Ala  Val Val Ile Ile Leu  Phe Ile Ile Leu Leu  Gly Val Ile
    1685                1690                1695

Met Ala  Lys Arg Lys Arg Lys  His Gly Ser Leu Trp  Leu Pro Glu
    1700                1705                1710

Gly Phe  Thr Leu Arg Arg Asp  Ala Ser Asn His Lys  Arg Arg Glu
    1715                1720                1725

Pro Val  Gly Gln Asp Ala Val  Gly Leu Lys Asn Leu  Ser Val Gln
    1730                1735                1740

Val Ser  Glu Ala Asn Leu Ile  Gly Thr Gly Thr Ser  Glu His Trp
    1745                1750                1755

Val Asp  Asp Glu Gly Pro Gln  Pro Lys Lys Val Lys  Ala Glu Asp
    1760                1765                1770

Glu Ala  Leu Leu Ser Glu Glu  Asp Asp Pro Ile Asp  Arg Arg Pro
    1775                1780                1785

Trp Thr  Gln Gln His Leu Glu  Ala Ala Asp Ile Arg  Arg Thr Pro
    1790                1795                1800

Ser Leu  Ala Leu Thr Pro Pro  Gln Ala Glu Gln Glu  Val Asp Val
    1805                1810                1815

Leu Asp  Val Asn Val Arg Gly  Pro Asp Gly Cys Thr  Pro Leu Met
    1820                1825                1830

Leu Ala  Ser Leu Arg Gly Gly  Ser Ser Asp Leu Ser  Asp Glu Asp
    1835                1840                1845

Glu Asp  Ala Glu Asp Ser Ser  Ala Asn Ile Ile Thr  Asp Leu Val
    1850                1855                1860

Tyr Gln  Gly Ala Ser Leu Gln  Ala Gln Thr Asp Arg  Thr Gly Glu
    1865                1870                1875

Met Ala  Leu His Leu Ala Ala  Arg Tyr Ser Arg Ala  Asp Ala Ala
    1880                1885                1890

Lys Arg  Leu Leu Asp Ala Gly  Ala Asp Ala Asn Ala  Gln Asp Asn
    1895                1900                1905

Met Gly  Arg Cys Pro Leu His  Ala Ala Val Ala Ala  Asp Ala Gln
    1910                1915                1920

Gly Val  Phe Gln Ile Leu Ile  Arg Asn Arg Val Thr  Asp Leu Asp
    1925                1930                1935

Ala Arg  Met Asn Asp Gly Thr  Thr Pro Leu Ile Leu  Ala Ala Arg
    1940                1945                1950
```

-continued

Leu Ala Val Glu Gly Met Val Ala Glu Leu Ile Asn Cys Gln Ala
1955 1960 1965

Asp Val Asn Ala Val Asp Asp His Gly Lys Ser Ala Leu His Trp
1970 1975 1980

Ala Ala Ala Val Asn Asn Val Glu Ala Thr Leu Leu Leu Leu Lys
1985 1990 1995

Asn Gly Ala Asn Arg Asp Met Gln Asp Asn Lys Glu Glu Thr Pro
2000 2005 2010

Leu Phe Leu Ala Ala Arg Glu Gly Ser Tyr Glu Ala Ala Lys Ile
2015 2020 2025

Leu Leu Asp His Phe Ala Asn Arg Asp Ile Thr Asp His Met Asp
2030 2035 2040

Arg Leu Pro Arg Asp Val Ala Arg Asp Arg Met His His Asp Ile
2045 2050 2055

Val Arg Leu Leu Asp Glu Tyr Asn Val Thr Pro Ser Pro Pro Gly
2060 2065 2070

Thr Val Leu Thr Ser Ala Leu Ser Pro Val Ile Cys Gly Pro Asn
2075 2080 2085

Arg Ser Phe Leu Ser Leu Lys His Thr Pro Met Gly Lys Lys Ser
2090 2095 2100

Arg Arg Pro Ser Ala Lys Ser Thr Met Pro Thr Ser Leu Pro Asn
2105 2110 2115

Leu Ala Lys Glu Ala Lys Asp Ala Lys Gly Ser Arg Arg Lys Lys
2120 2125 2130

Ser Leu Ser Glu Lys Val Gln Leu Ser Glu Ser Ser Val Thr Leu
2135 2140 2145

Ser Pro Val Asp Ser Leu Glu Ser Pro His Thr Tyr Val Ser Asp
2150 2155 2160

Thr Thr Ser Ser Pro Met Ile Thr Ser Pro Gly Ile Leu Gln Ala
2165 2170 2175

Ser Pro Asn Pro Met Leu Ala Thr Ala Ala Pro Pro Ala Pro Val
2180 2185 2190

His Ala Gln His Ala Leu Ser Phe Ser Asn Leu His Glu Met Gln
2195 2200 2205

Pro Leu Ala His Gly Ala Ser Thr Val Leu Pro Ser Val Ser Gln
2210 2215 2220

Leu Leu Ser His His His Ile Val Ser Pro Gly Ser Gly Ser Ala
2225 2230 2235

Gly Ser Leu Ser Arg Leu His Pro Val Pro Val Pro Ala Asp Trp
2240 2245 2250

Met Asn Arg Met Glu Val Asn Glu Thr Gln Tyr Asn Glu Met Phe
2255 2260 2265

Gly Met Val Leu Ala Pro Ala Glu Gly Thr His Pro Gly Ile Ala
2270 2275 2280

Pro Gln Ser Arg Pro Pro Glu Gly Lys His Ile Thr Thr Pro Arg
2285 2290 2295

Glu Pro Leu Pro Pro Ile Val Thr Phe Gln Leu Ile Pro Lys Gly
2300 2305 2310

Ser Ile Ala Gln Pro Ala Gly Ala Pro Gln Pro Gln Ser Thr Cys
2315 2320 2325

Pro Pro Ala Val Ala Gly Pro Leu Pro Thr Met Tyr Gln Ile Pro
2330 2335 2340

-continued

```
Glu Met  Ala Arg Leu Pro Ser  Val Ala Phe Pro Thr  Ala Met Met
    2345                 2350                 2355

Pro Gln  Gln Asp Gly Gln Val  Ala Gln Thr Ile Leu  Pro Ala Tyr
    2360                 2365                 2370

His Pro  Phe Pro Ala Ser Val  Gly Lys Tyr Pro Thr  Pro Pro Ser
    2375                 2380                 2385

Gln His  Ser Tyr Ala Ser Ser  Asn Ala Ala Glu Arg  Thr Pro Ser
    2390                 2395                 2400

His Ser  Gly His Leu Gln Gly  Glu His Pro Tyr Leu  Thr Pro Ser
    2405                 2410                 2415

Pro Glu  Ser Pro Asp Gln Trp  Ser Ser Ser Ser Pro  His Ser Ala
    2420                 2425                 2430

Ser Asp  Trp Ser Asp Val Thr  Thr Ser Pro Thr Pro  Gly Gly Ala
    2435                 2440                 2445

Gly Gly  Gly Gln Arg Gly Pro  Gly Thr His Met Ser  Glu Pro Pro
    2450                 2455                 2460

His Asn  Asn Met Gln Val Tyr  Ala
    2465                 2470


<210> SEQ ID NO 74
<211> LENGTH: 256
<212> TYPE: PRT
<213> ORGANISM: Homo sapiens

<400> SEQUENCE: 74

Pro Ala Thr Cys Leu Ser Gln Tyr Cys Ala Asp Lys Ala Arg Asp Gly
1               5                   10                  15

Val Cys Asp Glu Ala Cys Asn Ser His Ala Cys Gln Trp Asp Gly Gly
            20                  25                  30

Asp Cys Ser Leu Thr Met Glu Asn Pro Trp Ala Asn Cys Ser Ser Pro
        35                  40                  45

Leu Pro Cys Trp Asp Tyr Ile Asn Asn Gln Cys Asp Glu Leu Cys Asn
    50                  55                  60

Thr Val Glu Cys Leu Phe Asp Asn Phe Glu Cys Gln Gly Asn Ser Lys
65                  70                  75                  80

Thr Cys Lys Tyr Asp Lys Tyr Cys Ala Asp His Phe Lys Asp Asn His
                85                  90                  95

Cys Asp Gln Gly Cys Asn Ser Glu Glu Cys Gly Trp Asp Gly Leu Asp
            100                 105                 110

Cys Ala Ala Asp Gln Pro Glu Asn Leu Ala Glu Gly Thr Leu Val Ile
        115                 120                 125

Val Val Leu Met Pro Pro Glu Gln Leu Leu Gln Asp Ala Arg Ser Phe
    130                 135                 140

Leu Arg Ala Leu Gly Thr Leu Leu His Thr Asn Leu Arg Ile Lys Arg
145                 150                 155                 160

Asp Ser Gln Gly Glu Leu Met Val Tyr Pro Tyr Tyr Gly Glu Lys Ser
                165                 170                 175

Ala Ala Met Lys Lys Gln Arg Met Thr Arg Arg Ser Leu Pro Gly Glu
            180                 185                 190

Gln Glu Gln Glu Val Ala Gly Ser Lys Val Phe Leu Glu Ile Asp Asn
        195                 200                 205
```

-continued

| | | | | | | | | | | | | | | | |
|---|---|---|---|---|---|---|---|---|---|---|---|---|---|---|---|
| Arg | Gln | Cys | Val | Gln | Asp | Ser | Asp | His | Cys | Phe | Lys | Asn | Thr | Asp | Ala |
| | 210 | | | | | 215 | | | | | 220 | | | | |
| Ala | Ala | Ala | Leu | Leu | Ala | Ser | His | Ala | Ile | Gln | Gly | Thr | Leu | Ser | Tyr |
| 225 | | | | | 230 | | | | | 235 | | | | | 240 |
| Pro | Leu | Val | Ser | Val | Val | Ser | Glu | Ser | Leu | Thr | Pro | Glu | Arg | Thr | Gln |
| | | | | 245 | | | | | 250 | | | | | 255 | |

What is claimed is:

1. A method of treating liver fibrosis, the method comprising administering to a patient having liver fibrosis an effective amount of a Notch2-specific antagonist.

2. The method of claim 1, wherein the Notch2-specific antagonist is an anti-Notch2 antagonist antibody.

3. The method of claim 2, wherein the anti-Notch2 antagonist antibody is an anti-Notch2 negative regulatory region (NRR) antibody.

4. The method of claim 3, wherein the anti-Notch2 NRR antibody binds to the Lin12/Notch Repeat (LNR-A) and heterodimerization (HD)-C domains of Notch2 NRR.

5. The method of claim 3, wherein the anti-Notch2 NRR antibody is Antibody D, Antibody D-1, Antibody D-2, or Antibody D-3.

6. The method of claim 3, wherein the anti-Notch2 NRR antibody comprises the heavy and light chain variable region complementarity determining regions (CDRs) of Antibody D, Antibody D-1, Antibody D-2, or Antibody D-3.

7. The method of claim 2, wherein the anti-Notch2 antagonist antibody is an anti-Notch2 antibody that binds to one or more epidermal growth factor (EGF)-like repeats of Notch2.

8. The method of claim 1, wherein the Notch2-specific antagonist is administered by intramuscular, intraperitoneal, intracerobrospinal, subcutaneous, intra-articular, intrasynovial, intrathecal, oral, topical, or inhalation route.

9. A method of inducing hepatic differentiation, the method comprising the step of contacting an oval cell with an effective amount of a Notch2-specific antagonist, thereby inducing hepatic differentiation of the oval cell.

10. The method of claim 9, wherein the oval cell is contacted with the Notch2-specific antagonist in vitro.

11. The method of claim 9, wherein the oval cell is contacted with the Notch2-specific antagonist in vivo.

12. A method of reducing aberrant bile duct proliferation in a patient with liver fibrosis, the method comprising the step of administering to the patient an effective amount of a Notch2-specific antagonist, thereby reducing aberrant bile duct proliferation.

* * * * *